United States Patent
Okamoto et al.

(10) Patent No.: US 9,861,264 B2
(45) Date of Patent: Jan. 9, 2018

(54) RIGID ENDOSCOPE

(75) Inventors: Yasuhiro Okamoto, Hino (JP); Kazuo Banju, Hachioji (JP); Hiroki Moriyama, Akishima (JP)

(73) Assignee: OLYMPUS CORPORATION (JP)

( * ) Notice: Subject to any disclaimer, the term of this patent is extended or adjusted under 35 U.S.C. 154(b) by 92 days.

(21) Appl. No.: 13/553,911

(22) Filed: Jul. 20, 2012

(65) Prior Publication Data

US 2013/0072754 A1    Mar. 21, 2013

Related U.S. Application Data

(63) Continuation of application No. PCT/JP2011/065608, filed on Jul. 7, 2011.

(Continued)

(51) Int. Cl.
*A61B 1/00* (2006.01)
*A61B 1/06* (2006.01)
(Continued)

(52) U.S. Cl.
CPC .......... *A61B 1/00154* (2013.01); *A61B 1/005* (2013.01); *A61B 1/00078* (2013.01);
(Continued)

(58) Field of Classification Search
CPC ................ A61B 5/0084; A61B 5/0075; A61B 17/00008; A61B 2017/00969;
(Continued)

(56) References Cited

U.S. PATENT DOCUMENTS 3,005,452 A  10/1961 Pitman ............................ 128/11
5,987,346 A  11/1999 Benaron et al. .............. 600/407
(Continued)

FOREIGN PATENT DOCUMENTS

JP  6-154152   6/1994
JP  07-184856  7/1995
(Continued)

OTHER PUBLICATIONS

Olympus Optical Co LTD, Light Source Apparatus for Endoscope, Noguchi Toshiaki et al., Publication No. JP 07-184856, date of publication Jul. 27, 1995.*
(Continued)

*Primary Examiner* — John P Leubecker
*Assistant Examiner* — Rajaa El Alami
(74) *Attorney, Agent, or Firm* — Ostrolenk Faber LLP

(57) ABSTRACT

A rigid endoscope includes a first insertion section extending along longitudinal directions, a first needle defining an outer edge of a first opening, and a first functional section provided in a vicinity of the first opening of a first lumen, and configured to perform some part of functions. The rigid endoscope includes a second insertion section extending along the longitudinal directions, and located apart from the first insertion section in directions perpendicular to the longitudinal directions, a second needle defining an outer edge of a second opening, and a second functional section provided in a vicinity of the second opening of a second lumen, and configured to perform some part of the functions different from the functions performed by the first functional section.

15 Claims, 37 Drawing Sheets

Related U.S. Application Data

(60) Provisional application No. 61/368,310, filed on Jul. 28, 2010, provisional application No. 61/378,133, filed on Aug. 30, 2010.

(51) Int. Cl.
| | |
|---|---|
| *A61B 1/005* | (2006.01) |
| *A61B 1/04* | (2006.01) |
| *A61B 1/12* | (2006.01) |
| *A61B 1/313* | (2006.01) |
| *A61B 17/34* | (2006.01) |
| *A61B 17/00* | (2006.01) |
| *A61B 90/00* | (2016.01) |

(52) U.S. Cl.
CPC ...... *A61B 1/00105* (2013.01); *A61B 1/00128* (2013.01); *A61B 1/00163* (2013.01); *A61B 1/04* (2013.01); *A61B 1/0676* (2013.01); *A61B 1/12* (2013.01); *A61B 1/126* (2013.01); *A61B 1/313* (2013.01); *A61B 1/3132* (2013.01); *A61B 17/3421* (2013.01); *A61B 17/3478* (2013.01); *A61B 17/3496* (2013.01); *A61B 1/0014* (2013.01); *A61B 1/00103* (2013.01); *A61B 1/00119* (2013.01); *A61B 17/3417* (2013.01); *A61B 2017/00477* (2013.01); *A61B 2017/00557* (2013.01); *A61B 2017/3447* (2013.01); *A61B 2017/3466* (2013.01); *A61B 2017/3486* (2013.01); *A61B 2090/062* (2016.02)

(58) Field of Classification Search
CPC ...... A61B 2017/320044; A61B 5/0078; A61B 19/5212; A61B 2017/320048; A61B 17/11; A61B 2017/00243; A61B 17/3417; A61B 5/418; A61B 17/0218
USPC ........ 606/144, 101, 104, 108, 114, 129, 132
See application file for complete search history.

(56) References Cited

U.S. PATENT DOCUMENTS

| | | | |
|---|---|---|---|
| 6,572,532 B1 | 6/2003 | Pratt et al. | ...................... 600/30 |
| 7,918,868 B2 * | 4/2011 | Marshall et al. | ............. 606/144 |

FOREIGN PATENT DOCUMENTS

| | | |
|---|---|---|
| JP | 9-192086 | 7/1997 |
| JP | 10-137184 | 5/1998 |
| JP | 10-309256 | 11/1998 |
| JP | 2000-116663 | 4/2000 |
| JP | 2001-128923 | 5/2001 |
| JP | 2005-110940 | 4/2005 |
| JP | 2005-118134 | 5/2005 |
| JP | 2005-279010 | 10/2005 |
| JP | 2005-279253 | 10/2005 |
| JP | 2006-175038 | 7/2006 |
| JP | 2007-282965 | 11/2007 |
| JP | 2008-534237 | 8/2008 |
| JP | 2009-089724 | 4/2009 |
| JP | 2012-501695 | 1/2012 |
| WO | WO 98/27865 | 7/1998 |
| WO | WO 00/51676 | 9/2000 |
| WO | WO 2010/028701 | 3/2010 |

OTHER PUBLICATIONS

Olympus CORP, Puncture Needle and Ultrasonic Endoscope System, Nishina Kenchi et al., JP 2005-118134 A, May 12, 2005.*
Office Action issued by the Japanese Patent Office dated Nov. 20, 2012 in connection with corresponding Japanese Patent Application No. 2012-526403.
Translation of Office Action issued by the Japanese Patent Office dated Nov. 20, 2012 in connection with corresponding Japanese Patent Application No. 2012-526403.
English translation of the International Preliminary Report on Patentability for corresponding International Application No. PCT/JP2011/065608 dated Apr. 25, 2013.
International Search Report dated Aug. 2, 2011 in corresponding PCT International Application No. PCT/JP2011/065608 with English translation.
Written Opinion dated Aug. 2, 2011 in corresponding PCT International Application No. PCT/JP2011/065608.
Office Action issued by the Japanese Patent Office dated Aug. 28, 2012 in connection with corresponding Japanese Patent Application No. 2012-526403.
Translation of Office Action issued by the Japanese Patent Office dated Aug. 28, 2012 in connection with corresponding Japanese Patent Application No. 2012-526403.
Extended European Search Report and Written Opinion dated Jun. 6, 2017 issued in corresponding European Application No. 11812248.0-1666 / 2599427.

* cited by examiner

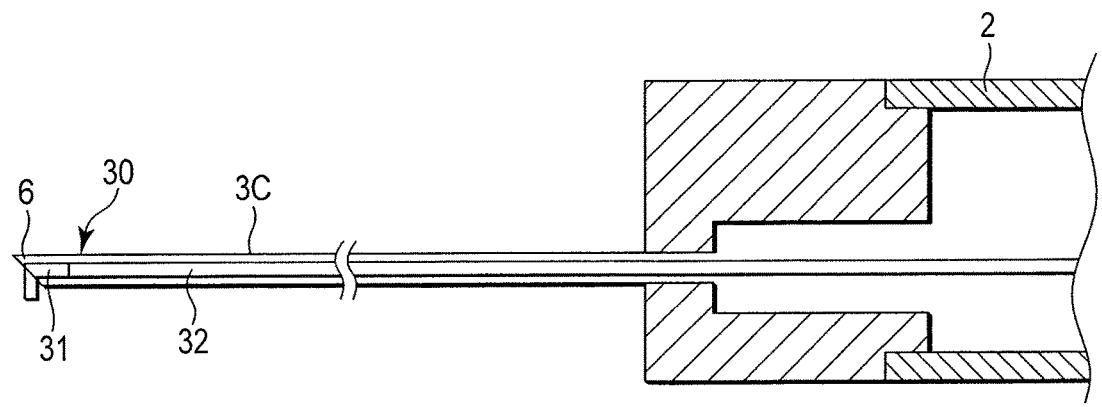
F I G. 3
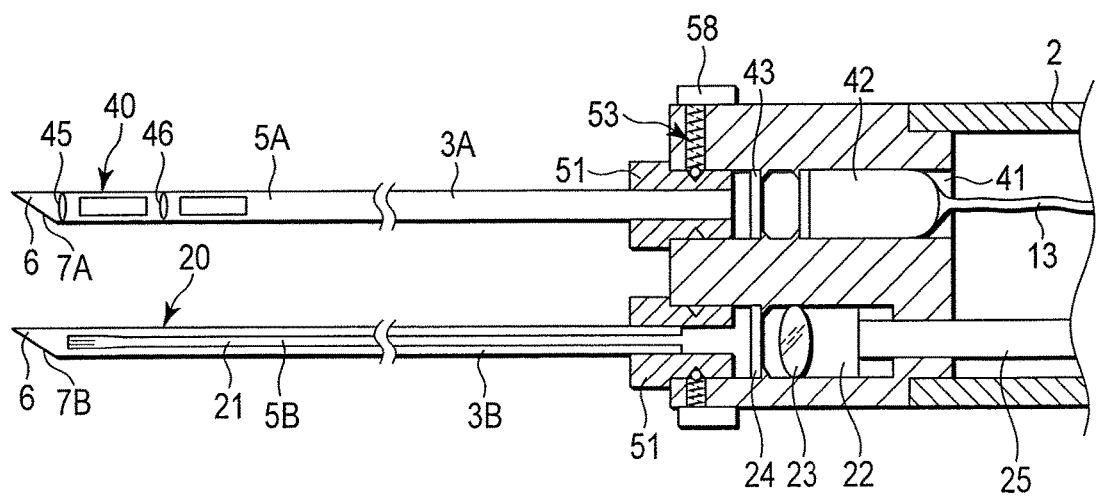
F I G. 4

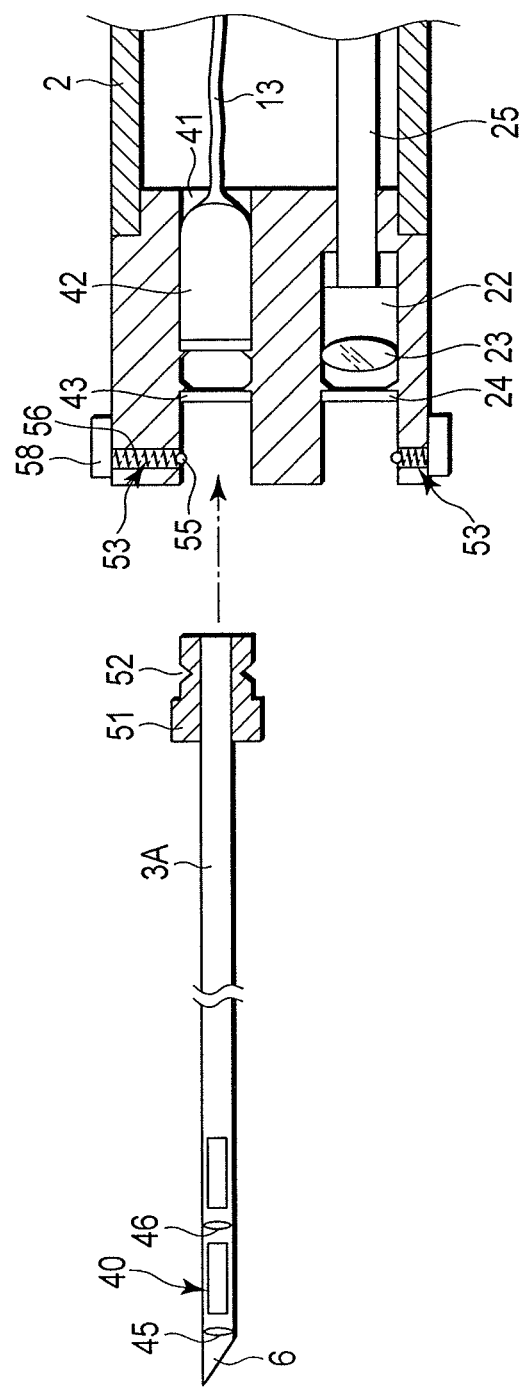
F I G. 5

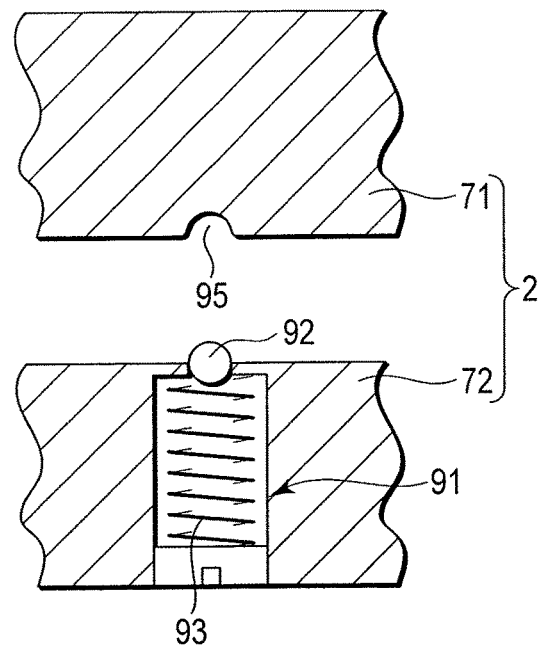
F I G. 12
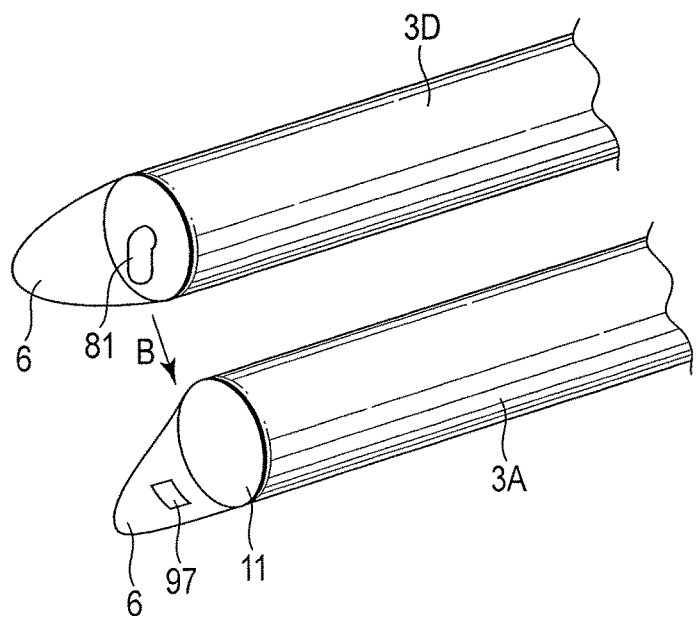
F I G. 13

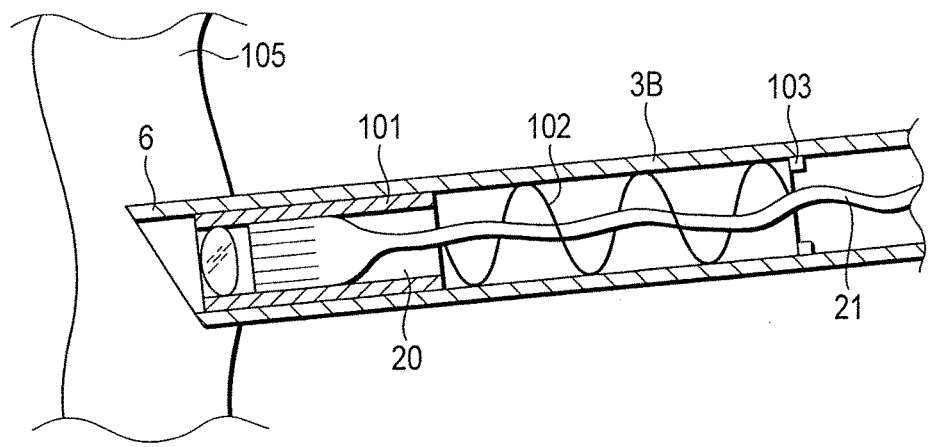
F I G. 14
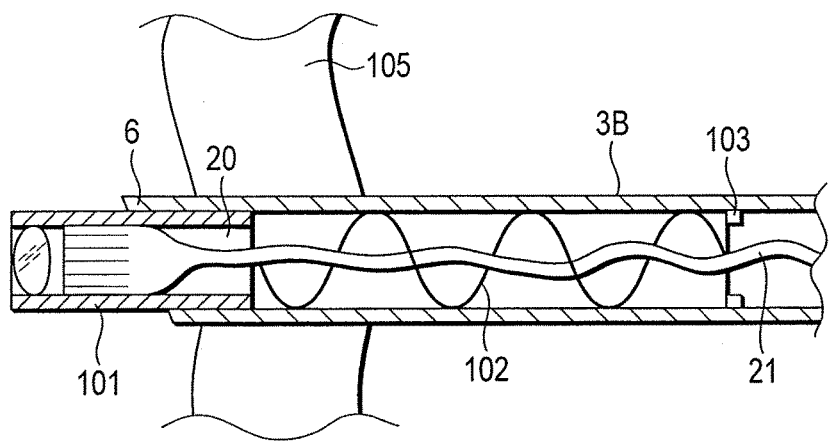
F I G. 15
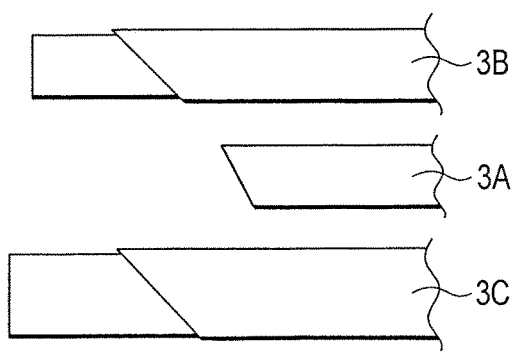
F I G. 16

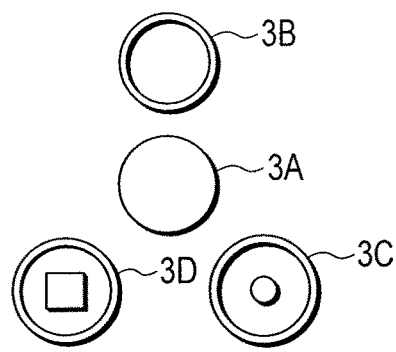
F I G. 17
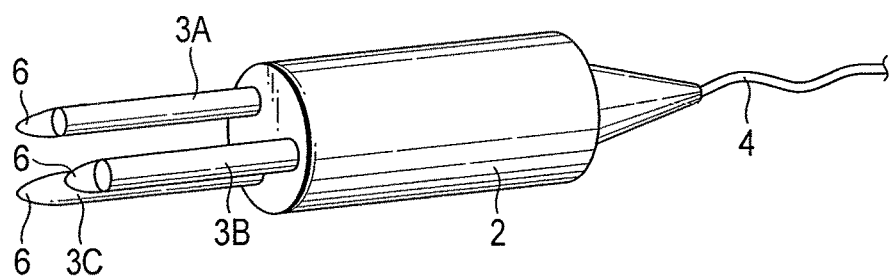
F I G. 18
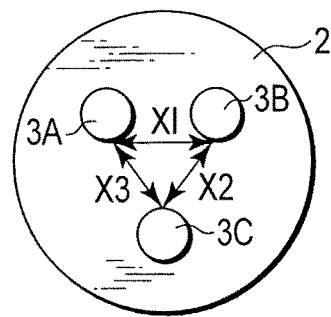
F I G. 19

| Dimensions X1, X2, X3 (X1=X2=X3) [mm] | Amount of sticking power [N] | Are Dimensions X1, X2, X3 appropriate? |
|---|---|---|
| 1 | 100 | No |
| 3 | 80 | Yes |
| 5 | 60 | Yes |
| 7 | 40 | Yes |
| 15 | 100 | No |

| Dimensions X4, X5 (X4=X5) [mm] | Amount of sticking power [N] | Are Dimensions X4, X5 appropriate? |
|---|---|---|
| 1 | 100 | No |
| 3 | 80 | Yes |
| 5 | 60 | Yes |
| 7 | 40 | Yes |
| 15 | 100 | No |

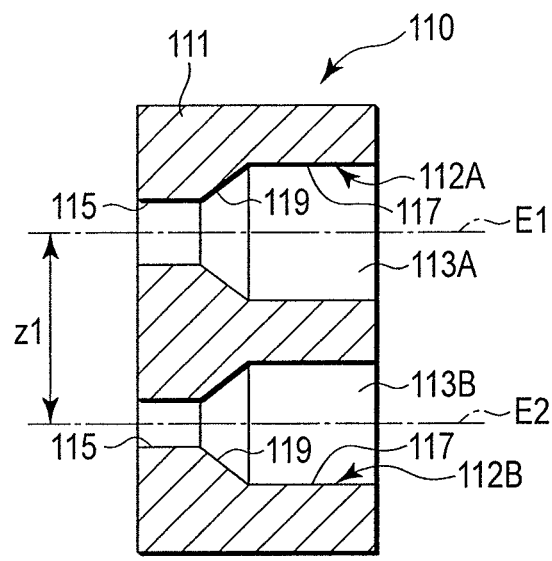
F I G. 28
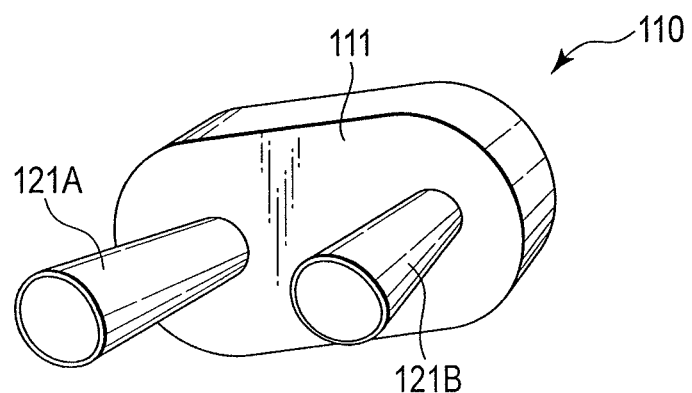
F I G. 29

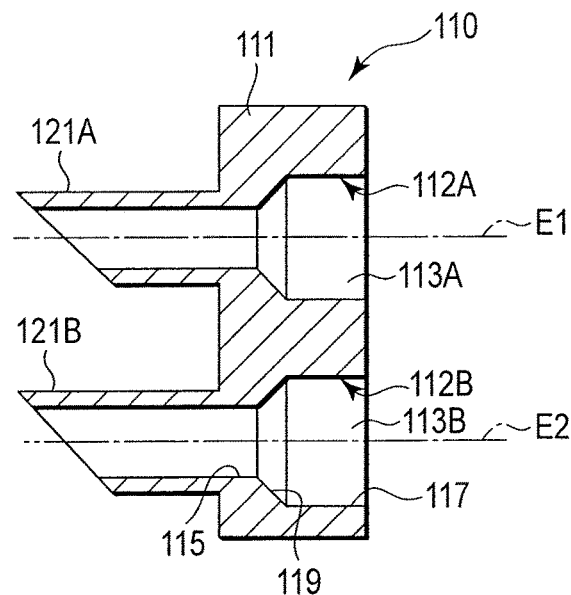
F I G. 30
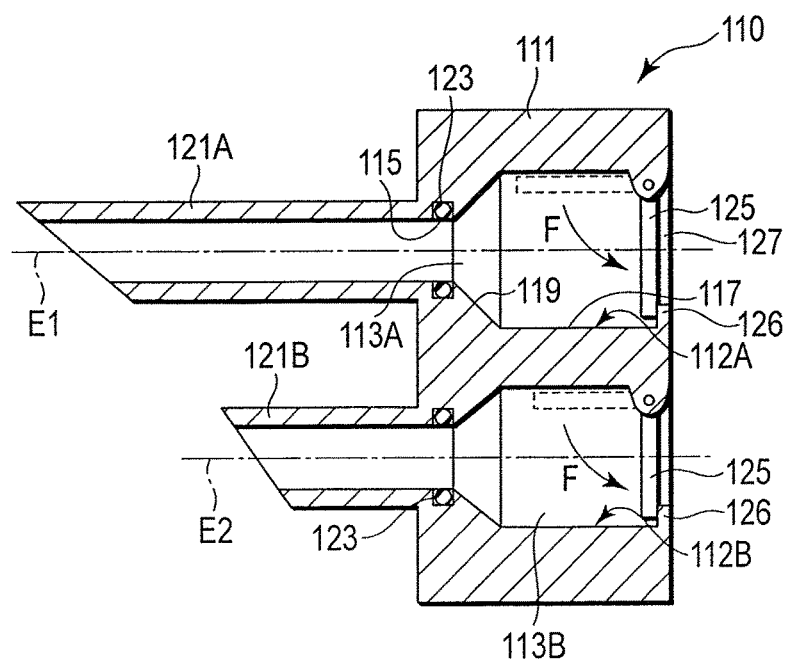
F I G. 31

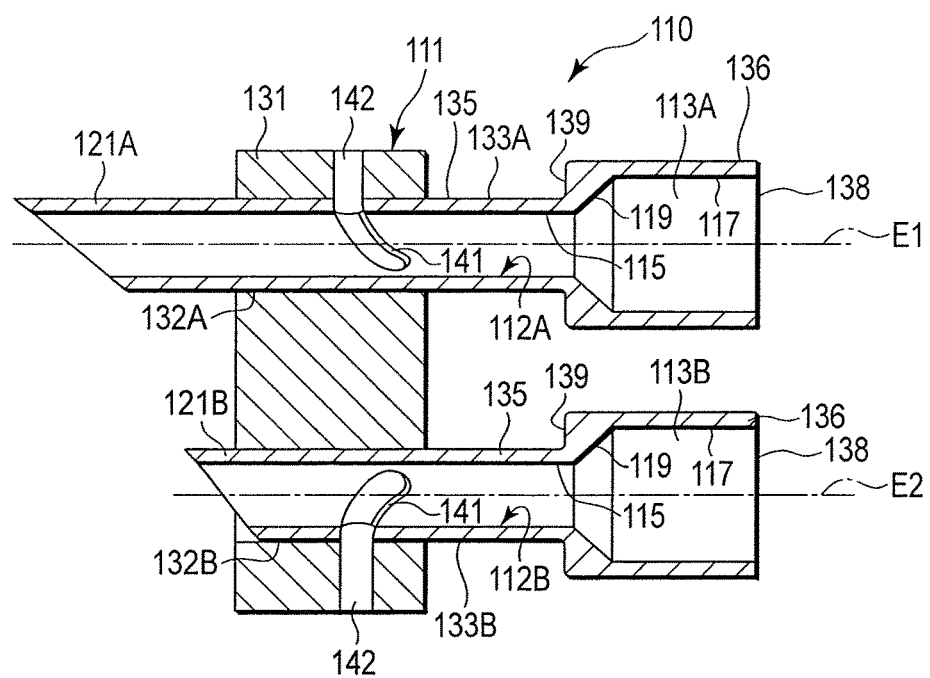
F I G. 32
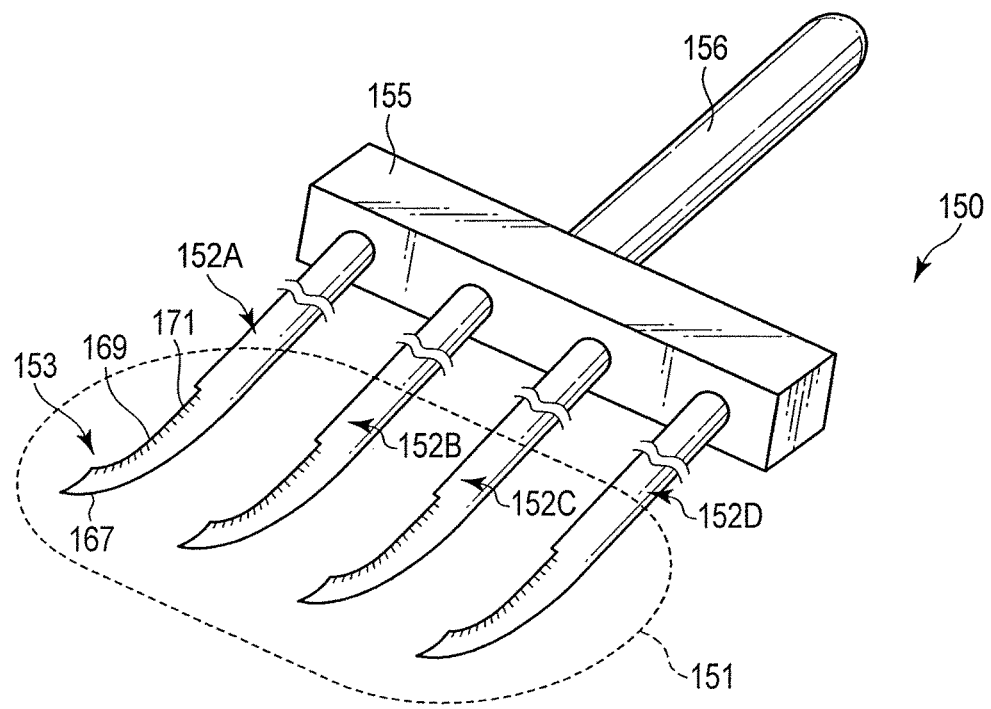
F I G. 33

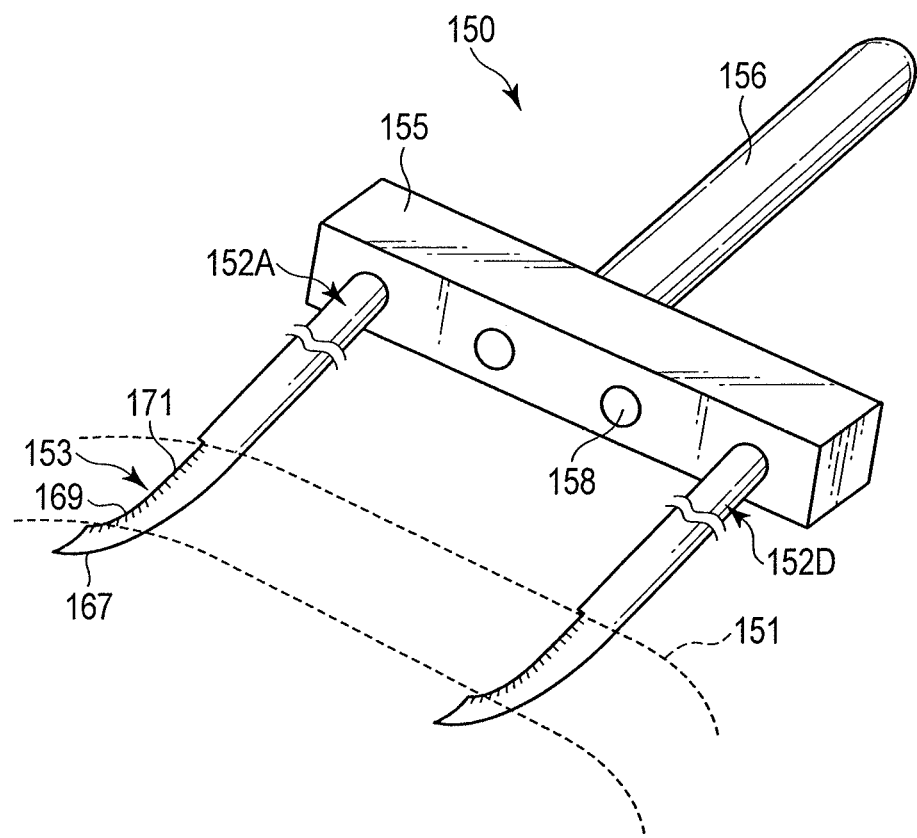
F I G. 34

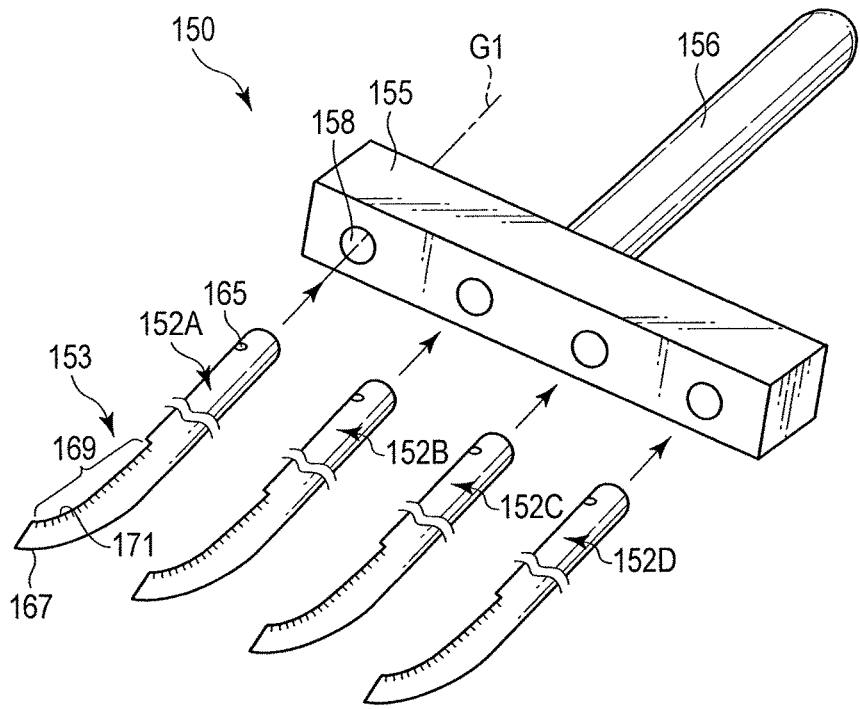
F I G. 35
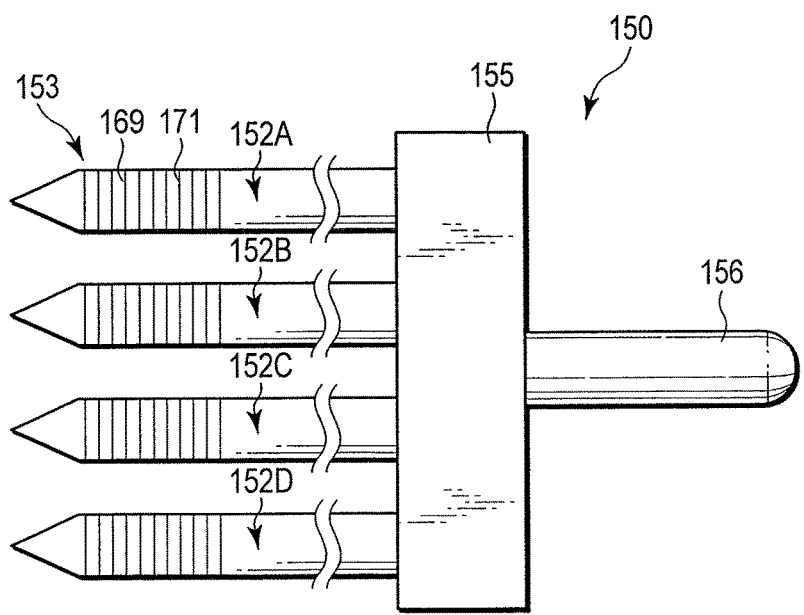
F I G. 36

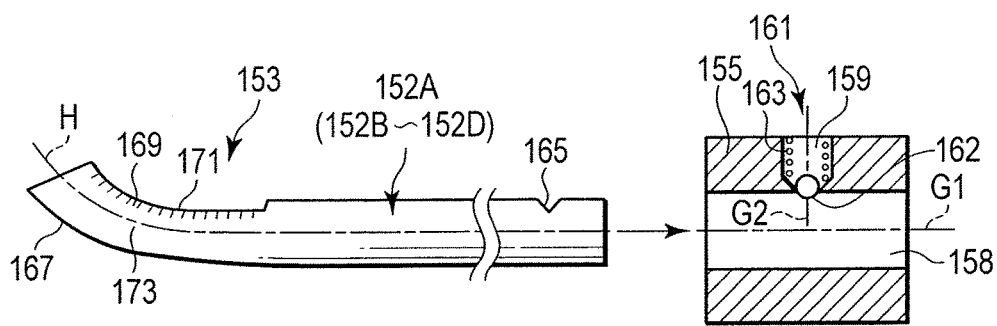
F I G. 37
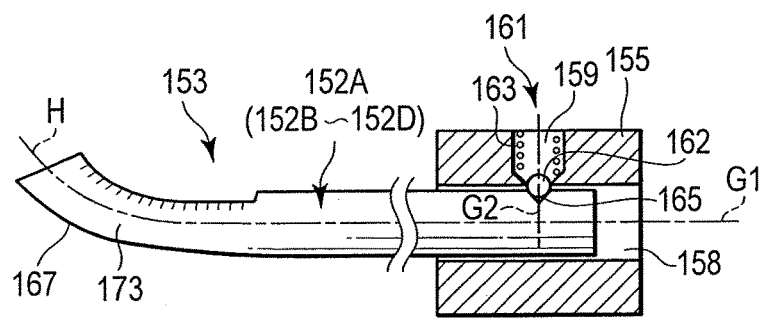
F I G. 38
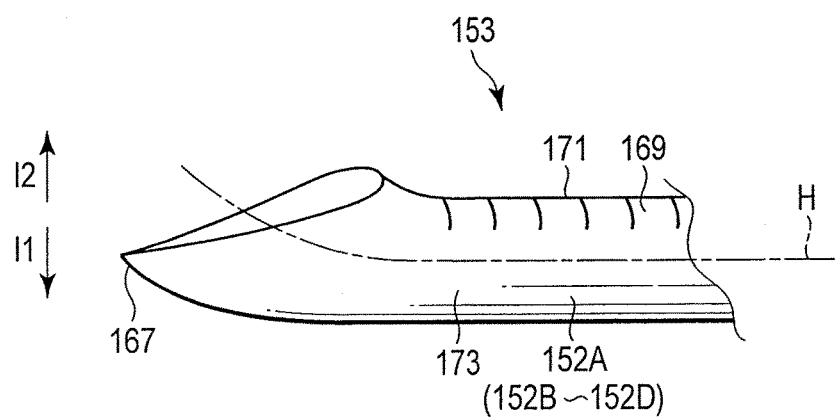
F I G. 39

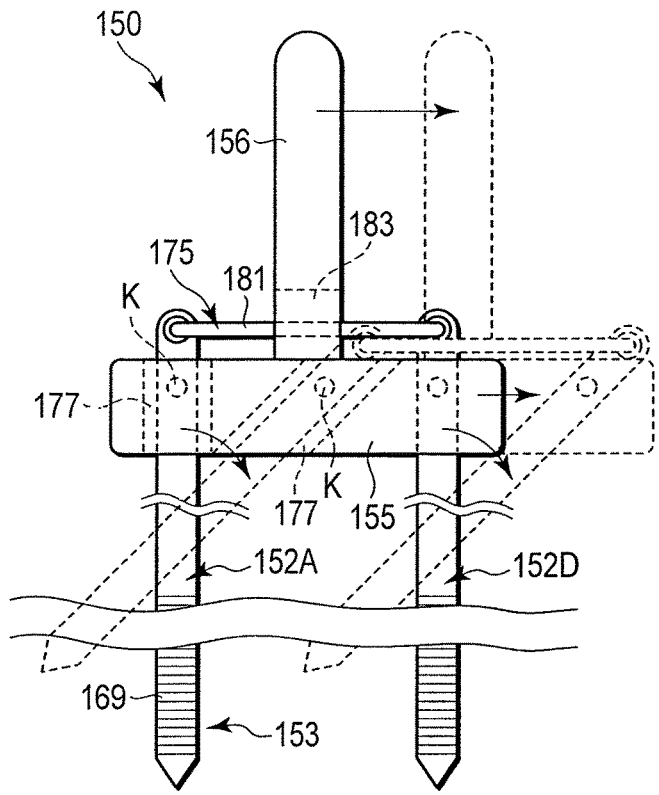
F I G. 40
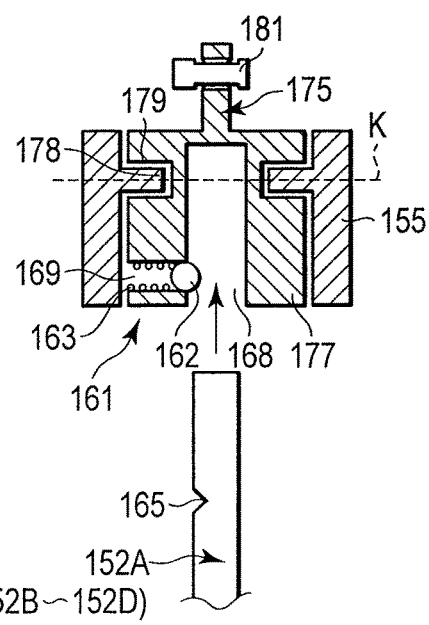
F I G. 41

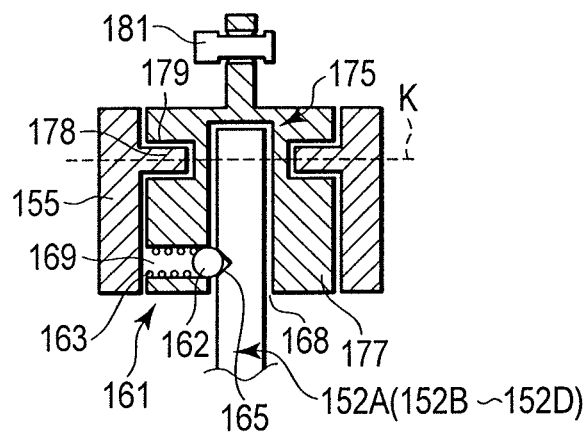
F I G. 42
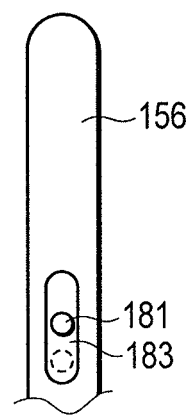
F I G. 43

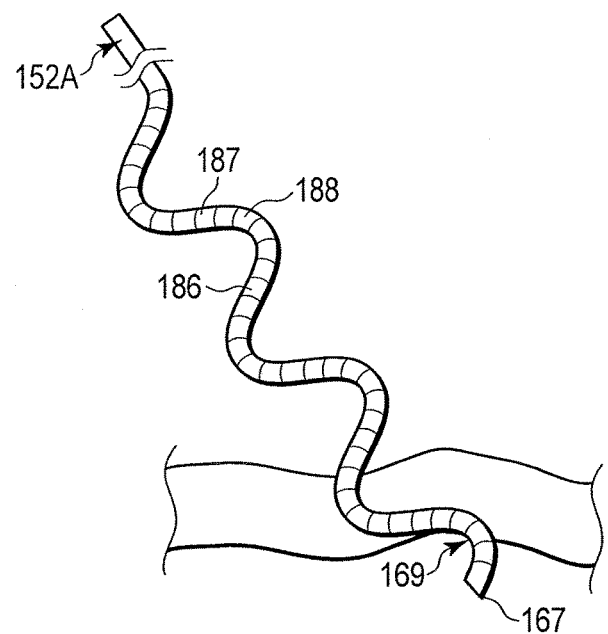
F I G. 45
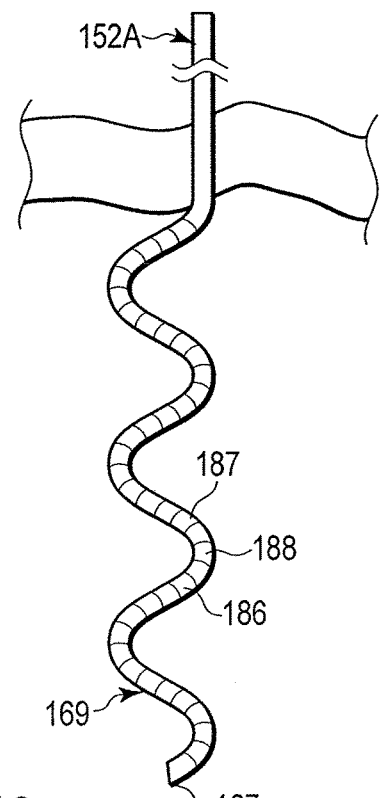
F I G. 46

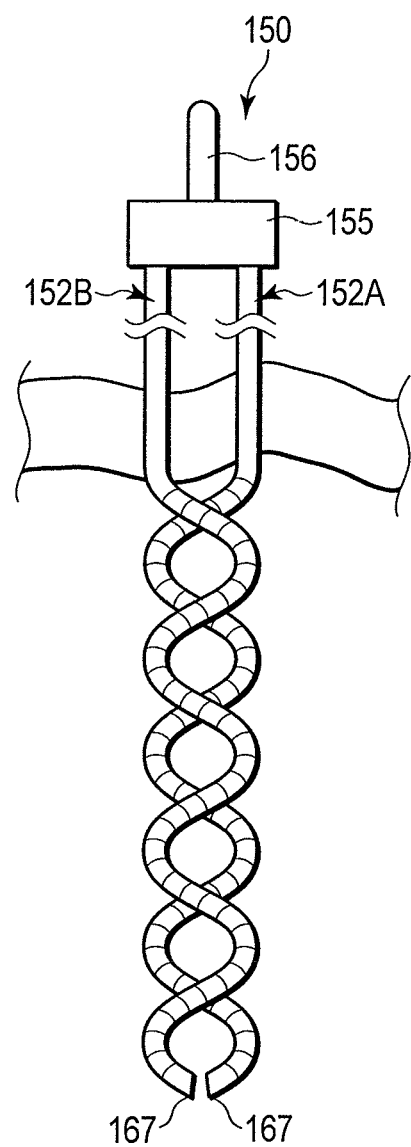
F I G. 48

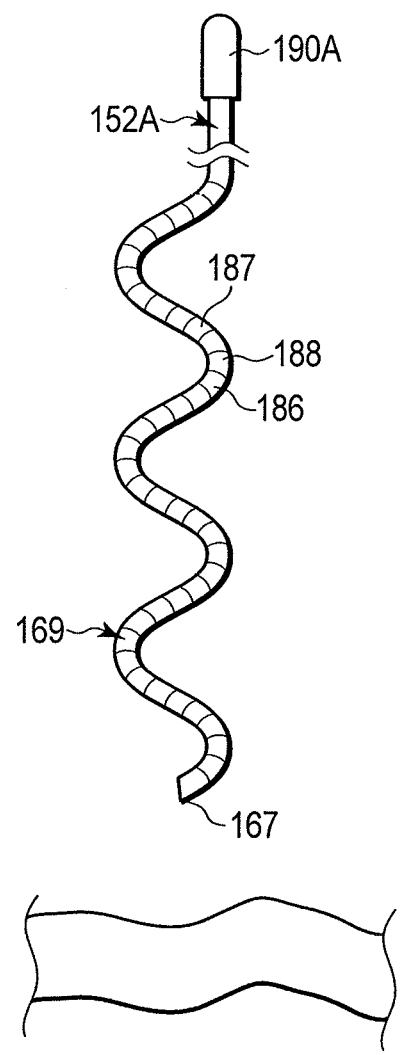
F I G. 49

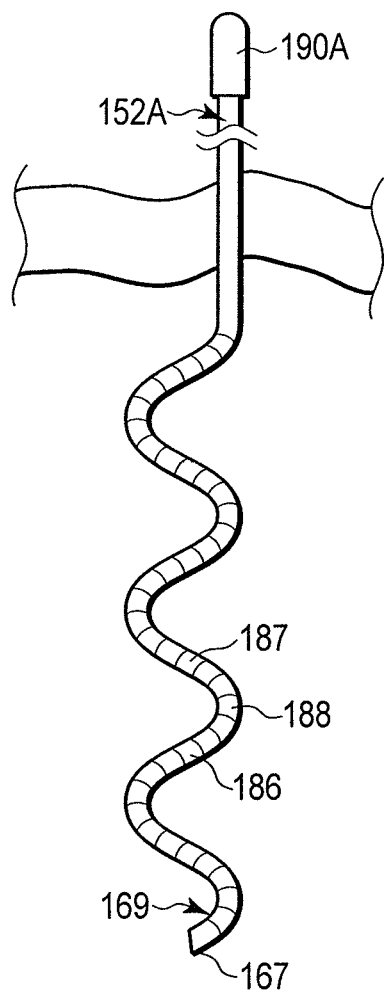
F I G. 51

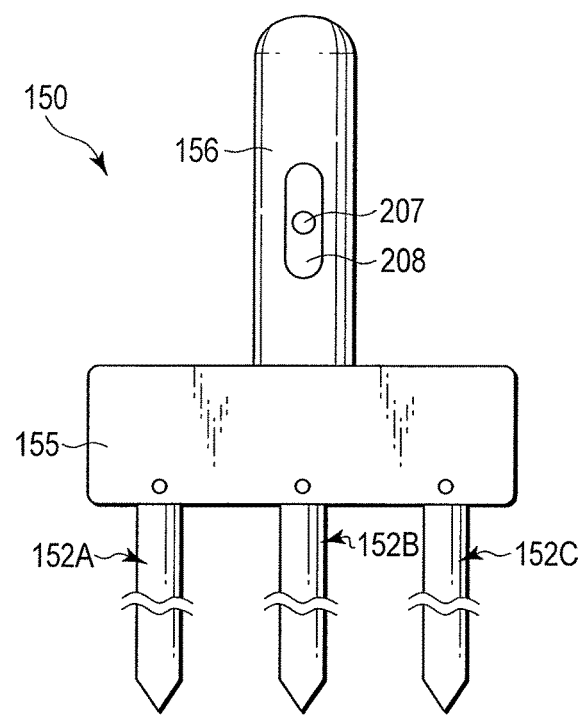
F I G. 53
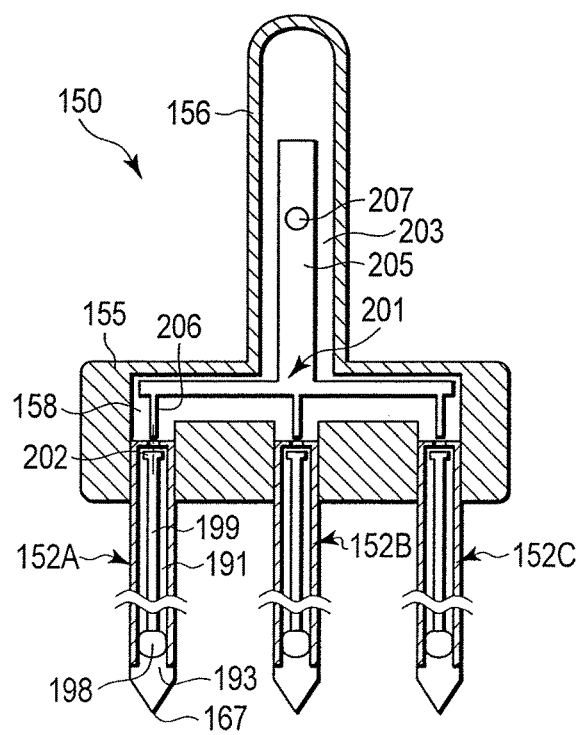
F I G. 54

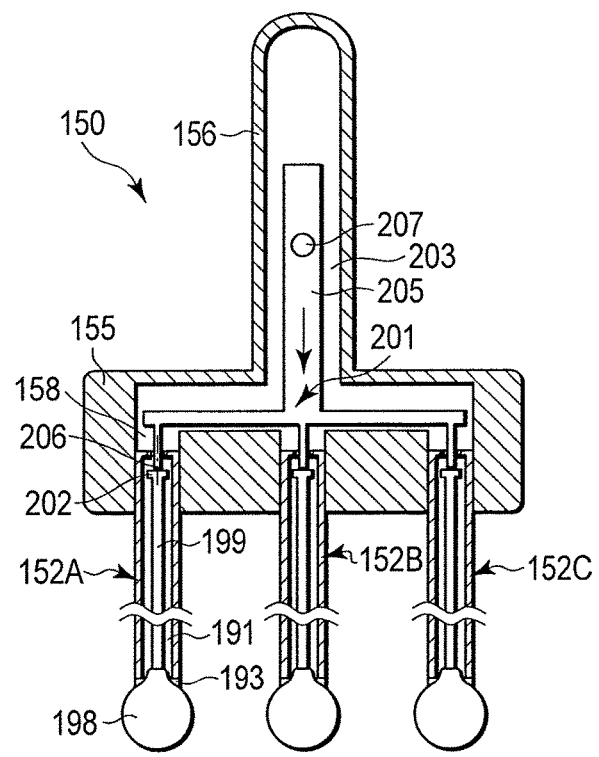
F I G. 55
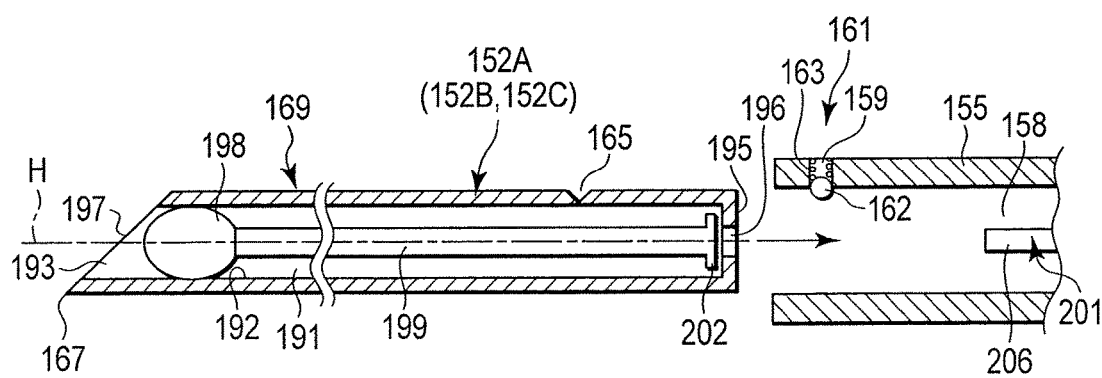
F I G. 56

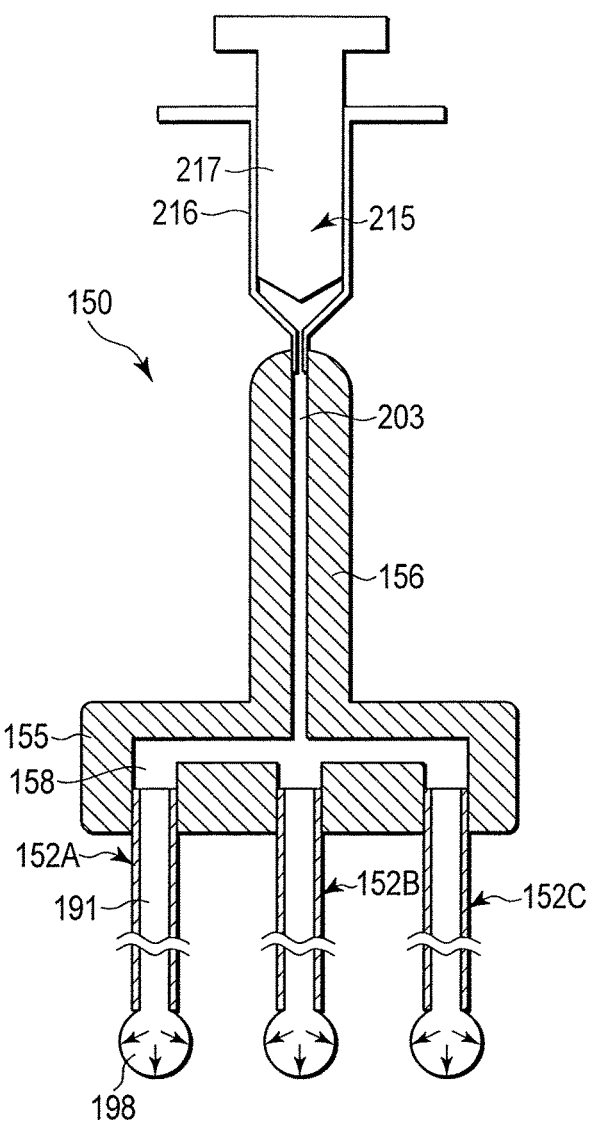
F I G. 61
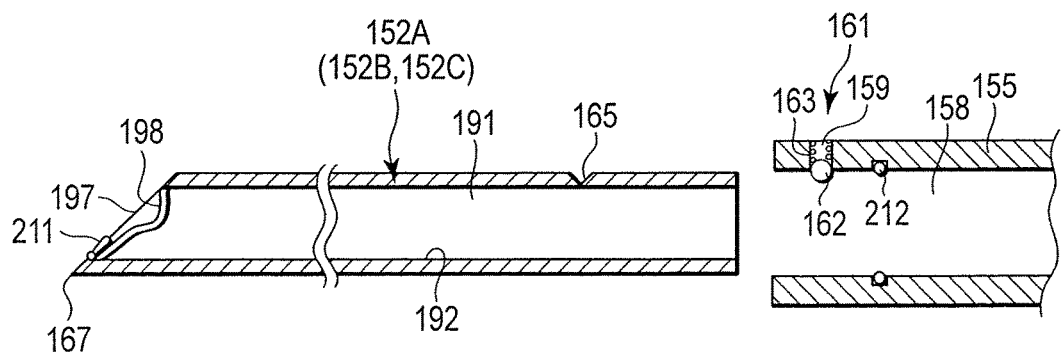
F I G. 62

RIGID ENDOSCOPE

CROSS-REFERENCE TO RELATED APPLICATIONS

This is a Continuation application of PCT Application No. PCT/JP2011/065608, filed Jul. 7, 2011 and based upon and claiming the benefit of priority from prior U.S. Provisional Applications No. 61/368,310, filed Jul. 28, 2010; and No. 61/378,133 filed Aug. 30, 2010, the entire contents of both of which are incorporated herein by reference.

BACKGROUND OF THE INVENTION

1. Field of the Invention

The present invention relates to a rigid endoscope configured to be inserted into a body cavity.

2. Description of the Related Art

In general, a rigid endoscope includes a body, and an insertion section extending from the body toward a distal direction. A needle is provided at a distal end portion of the insertion section, and is configured to be stuck into a body wall when the insertion section is inserted into a body cavity. A plurality of functional sections are provided in the insertion section, and the functional sections are such as an image pickup unit including an image pickup element, a light guide, and an air/water supply nozzle. An outside diameter of the insertion section including the functional sections therein is about 5 mm.

Jpn. Pat. Appln. KOKAI Publication No 2005-118134 discloses an endoscope in which a needle configured to be stuck into a body wall is provided at the distal end portion of an insertion section. In this endoscope, optical observation mechanism such as a CCD and illumination mechanism such as a light guide are provided in the insertion section.

BRIEF SUMMARY OF THE INVENTION

According to one aspect of the invention, a rigid endoscope having a plurality of functions, the rigid endoscope includes that a first insertion section extending along longitudinal directions; a first lumen defining portion which is formed in the first insertion section along the longitudinal directions, and which defines a first lumen that is open in a first opening at a distal end portion of the first insertion section; a first needle which defines an outer edge of the first opening, and which is sharpened from a proximal direction toward a distal direction; a first functional section which is provided in a vicinity of the first opening of the first lumen, and which is configured to perform some part of the functions; a second insertion section which extends along the longitudinal directions, and which is located apart from the first insertion section in directions perpendicular to the longitudinal directions; a second lumen defining portion which is formed in the second insertion section along the longitudinal directions, and which defines a second lumen that is open in a second opening at distal end portion of the second insertion section; second needle which defines an outer edge of the second opening, and which is sharpened from the proximal direction toward the distal direction; and a second functional section which is provided in a vicinity of the second opening of the second lumen, and which is configured to perform some part of the functions different from the functions performed by the first functional section, wherein the first insertion section includes an observation insertion section which includes, as the first functional section, an observation section configured to observe a subject.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3 is a sectional view schematically showing the internal structure of a part of the rigid endoscope according to the first embodiment different from the part shown in FIG. 2;

FIG. 4 is a sectional view schematically showing an internal structure of a rigid endoscope according to a second embodiment of the present invention;

FIG. 5 is a sectional view schematically showing coupling structure of a body and an insertion section of the rigid endoscope according to the second embodiment;

FIG. 12 is a sectional view schematically showing an attachment/detachment structure of the first formation and the second formation of the rigid endoscope according to the fifth embodiment;

FIG. 13 is a perspective view schematically showing the configurations of an observation insertion section and a cleaning insertion section of a rigid endoscope according to a sixth embodiment of the present invention;

FIG. 14 is a sectional view schematically showing a state in which a movable member of an irradiation insertion section of a rigid endoscope according to a seventh embodiment of the present invention is located at a second position;

FIG. 15 is a sectional view schematically showing a state in which the movable member of the irradiation insertion section of the rigid endoscope according to the seventh embodiment is located at a first position;

FIG. 16 is a side view schematically showing insertion sections according to an eighth embodiment of the present invention;

FIG. 17 is a schematic view showing the insertion sections according to the eighth embodiment from the distal direction;

FIG. 18 is a perspective view schematically showing a rigid endoscope according to a ninth embodiment of the present invention;

FIG. 19 is a schematic view showing the rigid endoscope according to the ninth embodiment from the distal direction;

FIG. 28 is a sectional view schematically showing the sticking assist instrument according to the eleventh embodiment;

FIG. 29 is a perspective view schematically showing a sticking assist instrument according to a twelfth embodiment of the present invention;

FIG. 30 is a sectional view schematically showing the sticking assist instrument according to the twelfth embodiment;

FIG. 31 is a sectional view schematically showing a sticking assist instrument according to a thirteenth embodiment of the present invention;

FIG. 32 is a sectional view schematically showing a sticking assist instrument according to a fourteenth embodiment of the present invention;

FIG. 33 is a perspective view schematically showing a state in which four insertion sections of an exclusion forceps according to a fifteenth embodiment of the present invention are held by a holder;

FIG. 34 is a perspective view schematically showing a state in which two insertion sections of the exclusion forceps according to the fifteenth embodiment are held by the holder;

FIG. 35 is a perspective view schematically showing a state in which the insertion sections of the exclusion forceps according to the fifteenth embodiment are removed from the holder;

FIG. 36 is a plan view schematically showing the exclusion forceps according to the fifteenth embodiment;

FIG. 37 is a sectional view schematically showing a state before the insertion section of the exclusion forceps according to the fifteenth embodiment is attached to the holder;

FIG. 38 is a sectional view schematically showing a state in which the insertion section of the exclusion forceps according to the fifteenth embodiment is attached to the holder;

FIG. 39 is a perspective view schematically showing a distal end portion of the exclusion forceps according to the fifteenth embodiment;

FIG. 40 is a plan view schematically showing an exclusion forceps according to the sixteenth embodiment of the present invention;

FIG. 41 is a sectional view schematically showing a state before an insertion section of the exclusion forceps according to the sixteenth embodiment is attached to a holder;

FIG. 42 is a sectional view schematically showing a state in which the insertion section of the exclusion forceps according to the sixteenth embodiment is attached to the holder;

FIG. 43 is a schematic view showing the configuration of a grip of the exclusion forceps according to the sixteenth embodiment;

FIG. 45 is a schematic view showing a state in needle of one insertion section of the exclusion forceps according to the seventeenth embodiment is stuck into a body wall;

FIG. 46 is a schematic view showing a state in which a zigzag portion of one insertion section of the exclusion forceps according to the seventeenth embodiment is inserted into a body cavity;

FIG. 48 is a schematic view showing a state in which the insertion sections of the exclusion forceps according to the seventeenth embodiment are held by holder;

FIG. 49 is a schematic view showing a state before one insertion section of an exclusion forceps according to a modification of the seventeenth embodiment is inserted into a body cavity;

FIG. 51 is a schematic view showing a state in which a zigzag portion of one insertion section of the exclusion forceps according to the modification of the seventeenth embodiment is inserted into a body cavity;

FIG. 53 is a plan view schematically showing an exclusion forceps according to an eighteenth embodiment of the present invention;

FIG. 54 is a sectional view schematically showing a state in which a cover member of the exclusion forceps according to the eighteenth embodiment is deflated in a bore-like portion of a corresponding insertion section;

FIG. 55 is a sectional view schematically showing a state in which the cover member of the exclusion forceps according to the eighteenth embodiment is projecting toward the distal direction from an opening of the corresponding insertion section and is inflated;

FIG. 56 is a sectional view schematically showing a state before the insertion section of the exclusion forceps according to the eighteenth embodiment is attached to a holder;

FIG. 61 is a sectional view schematically showing a state in which the cover member of the exclusion forceps according to the modification of the eighteenth embodiment is projecting toward the distal direction from an opening of the corresponding insertion section and is inflated;

FIG. 62 is a sectional view schematically showing a state before the insertion section of the exclusion forceps according to the modification of the eighteenth embodiment is attached to a holder;

DETAILED DESCRIPTION OF THE INVENTION

First Embodiment

Figure 1:
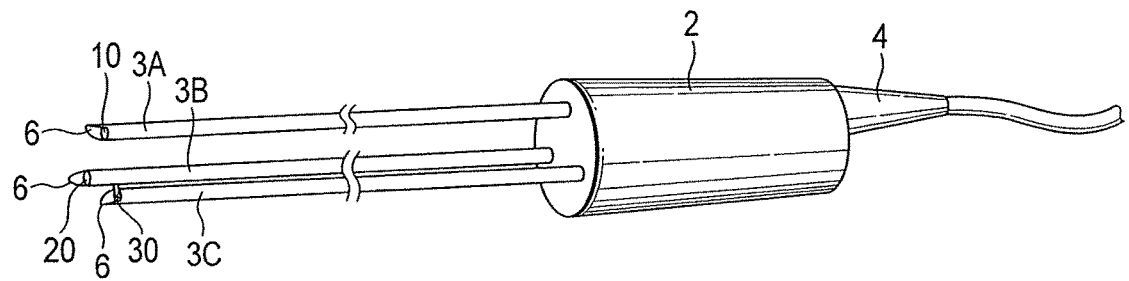
FIG. 1 is a perspective view schematically showing a rigid endoscope according to a first embodiment of the present invention.

A first embodiment of the present invention will be described with reference to FIG. 1 and FIG. 2. FIG. 1 is a diagram showing a rigid endoscope 1 according to the present embodiment. As shown in FIG. 1, the rigid endoscope 1 has a proximal end and a distal end, and extends in longitudinal directions from the proximal end to the distal end. The rigid endoscope 1 includes a body 2, and a plurality of (three in the present embodiment) insertion sections 3A to 3C which are provided to a distal direction side of the body 2, and which are configured to be inserted into a body cavity that is a void. That is, the body 2 is provided to a proximal direction side of the insertion sections 3A to 3C. One end of a universal cord 4 is connected to a proximal end of the body 2. The universal cord 4 is connected to peripheral units (not shown) of a rigid endoscope system via a scope connector (not shown) provided at the other end. The insertion sections 3A to 3C are arranged apart from one another in directions perpendicular to the longitudinal directions. The insertion sections 3A to 3C extend from the body 2 toward the distal direction. A needle 6 is provided at a distal end portion of each of the insertion sections 3A to 3C. The needles 6 are stuck into a body wall which is a wall part when the insertion sections 3A to 3C are inserted into the body cavity (void). Each of the needles 6 is sharpened from the proximal direction toward the distal direction. That is, each of the insertion sections 3A to 3C is inserted into the body cavity (void) through the body wall (wall part).

Figure 2:
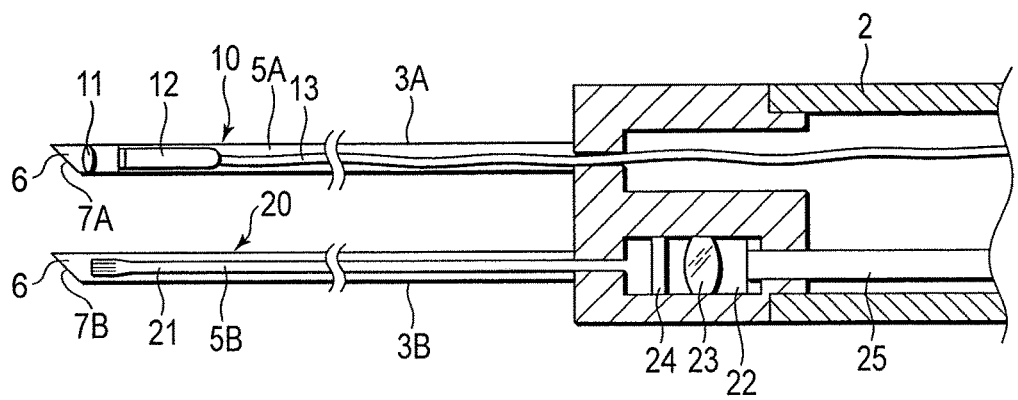
FIG. 2 is a sectional view schematically showing an internal structure of the rigid endoscope according to the first embodiment.

FIG. 2 and FIG. 3 are diagrams showing the internal structure of the rigid endoscope 1. As shown in FIG. 1 to FIG. 3, the insertion sections 3A to 3C includes an observation insertion section 3A including therein an observation section 10 as a functional section, an irradiation insertion section 3B including therein an illumination section 20 as a functional section, and an air/water supply insertion section 3C including therein an air/water supply section 30 as a functional section. The observation section 10, the illumination section 20, and the air/water supply section 30 each perform some part of all the functions (multiple functions) of the rigid endoscope 1.

The observation section (first functional section) 10 is configured to observe a subject. That is, the observation section 10 is configured to perform some part of the multiple functions. The observation section 10 includes an objective lens 11 configured to form a subject image, and an image pickup unit 12 provided to the proximal direction side of the objective lens 11. The image pickup unit 12 includes an image pickup element, and is configured to pick up the subject image formed by the objective lens 11. One end of an imaging cable 13 is connected to the image pickup unit 12. The other end of the imaging cable 13 is connected, through the observation insertion section 3A, the body 2, and the universal cord 4, to an image processing unit (not shown) which is one of the peripheral units.

Here, the observation section 10 is provided in a lumen 5A (first lumen) extending in the observation insertion section (first insertion section) 3A along the longitudinal directions. The lumen 5A is defined by a lumen defining portion (first lumen defining portion) such as an inner peripheral portion of the observation insertion section 3A. The lumen 5A is open in an opening 7A (first opening) at the distal end portion of the observation insertion section 3A. The observation section 10 is located in the vicinity of the opening 7A of the lumen 5A. An outer edge of the opening 7A is defined by the needle (first needle) 6.

The illumination section (second functional section) 20 is configured to apply light to the subject. That is, the illumination section 20 is configured to perform some part of the multiple functions different from those of the observation section (first functional section) 10. The illumination section 20 includes a light guide portion 21 configured to guide irradiating light to the subject. A lens storage portion 22 is provided at the distal end portion of the body 2. A proximal end of the light guide portion 21 is in communication with the lens storage portion 22. Disposed in the lens storage portion 22 are a condensing lens 23, and a cover glass 24 provided to the distal direction side of the condensing lens 23. One end of a light guide tube 25 is coupled to a proximal end portion of the lens storage portion 22. The other end of the light guide tube 25 is connected, through the body 2 and the universal cord 4, to an illumination power supply unit (not shown) which is one of the peripheral units. Light exiting from the illumination power supply unit is guided to the condensing lens 23 via the light guide tube 25. The light condensed by the condensing lens 23 is applied to the subject via the light guide portion 21.

Here, the illumination section 20 is provided in a lumen 5B (second lumen) extending in the illumination insertion section (second insertion section) 3B along the longitudinal directions. The lumen 5B is defined by a lumen defining portion (second lumen defining portion) such as the light guide portion 21. The lumen 5B is open in an opening 7B (second opening) at the distal end portion of the illumination insertion section 3B. The illumination section 20 is located in the vicinity of the opening 7B of the lumen 5B. An outer edge of the opening 7B is defined by the needle (second needle) 6.

The air/water supply insertion section 3C is provided with the air/water supply section 30 which is one of a plurality of the functional sections of the rigid endoscope 1. The air/water supply section 30 is configured to supply air/water to the objective lens 11. The air/water supply section 30 includes an air/water supply nozzle 31 provided at a distal end of the air/water supply insertion section 3C. One end of an air/water supply tube 32 is connected to a proximal end of the air/water supply nozzle 31. The other end of the air/water supply tube 32 is connected, through the air/water supply insertion section 3C, the body 2, and the universal cord 4, to an air/water supply unit (not shown) which is one of the peripheral units.

Now, the action of the rigid endoscope 1 according to the present embodiment is described. When the rigid endoscope 1 is used, the needle 6 of each of the insertion sections 3A to 3C is stuck into the body wall, and each of the insertion sections 3A to 3C is thereby inserted into the body cavity. The functional sections 10, 20, and 30 of the rigid endoscope 1 are arranged in a dispersed manner in the insertion sections 3A to 3C. Therefore, the insertion sections 3A to 3C can be reduced in outside diameter. Diameters of bores to be formed in the body wall are reduced by the reduction of the outside diameters of the insertion sections 3A to 3C. This leads to a low invasive degree during insertion into the body cavity. In the rigid endoscope 1, the functional sections 10, 20, and 30 are only arranged in the dispersed manner, and the number of the functional sections 10, 20, and 30 is reduced. Therefore, the function of the rigid endoscope 1 does not deteriorate.

Accordingly, the rigid endoscope 1 having the configuration described above provides the following advantageous effects. That is, a plurality of (three in the present embodiment) insertion sections 3A to 3C are provided in the rigid endoscope 1 according to the present embodiment. The multiple functional sections 10, 20, and 30 of the rigid endoscope 1 are arranged in dispersed manner in the insertion sections 3A to respectively. This allows the reduction of the outside diameters of the insertion sections 3A to 3C. The diameters of a bores to be formed in the body wall are reduced by the reduction of the outside diameters of the insertion sections 3A to 3C. This permits a low invasive degree during insertion into the body cavity. As the number of the functional sections 10, 20, and 30 is not reduced, the deterioration of the function of the rigid endoscope 1 can be prevented.

Modification of First Embodiment

The configuration according to the first embodiment includes the three insertion sections 3A to 3C including the observation insertion section 3A provided with the observation section 10, the irradiation insertion section 3B provided with the illumination section 20, and the air/water supply insertion section 3C provided with the air/water supply section 30. However, the present invention is not limited thereto. For example, as a modification, suction insertion section provided with a suction section configured to perform suction may be further provided. That is, it is only necessary to provide a plurality of insertion sections (the insertion sections 3A to 3C in the first embodiment) which are arranged apart from one another in directions perpendicular to the longitudinal directions, and which extend from the body 2 toward the distal direction. A needle 6 is provided at the distal end portion of each of the insertion sections, and a functional section provided in each of the insertion sections has only to perform some part of the multiple functions.

The second insertion section (e.g. 3B) has only to be disposed apart from the first insertion section (e.g. 3A) in directions perpendicular to the longitudinal directions. The first functional section (e.g. 10) has only to perform some part of the multiple functions, and the second functional section (e.g. 20) has only to perform some part of the multiple functions different from those of the first functional section. For example, the first insertion section may be the illumination insertion section 3B, and the second insertion section may be the air/water supply insertion section 3C. In this case, the illumination section 20 is the first functional section, and the air/water supply section 30 is the second functional section.

Although the condensing lens 23 is disposed in the lens storage portion 22 provided in the body 2 in the first embodiment, the present invention is not limited thereto. For example, as a modification, the condensing lens 23 may be disposed midway of the light guide portion 21 of the irradiation insertion section 3B. In this case, light exiting from the illumination power supply unit is guided to the condensing lens 23 via the light guide tube 25 and a part of the light guide portion 21 to the proximal direction side of the condensing lens 23. The light condensed by the condensing lens 23 is applied to the subject via a part of the light guide portion 21 to the distal direction side of the condensing lens 23.

Second Embodiment

Now, a second embodiment of the present invention will be described with reference to FIG. 4 and FIG. 5. In the second embodiment, the configuration according to the first embodiment is modified as follows. The same components as those in the first embodiment are provided with the same reference signs and are not described.

FIG. 4 is a diagram showing an internal structure of a rigid endoscope 1 according to the present embodiment. As shown in FIG. 4, the rigid endoscope includes an observation insertion section 3A and an irradiation insertion section 3B as in the first embodiment. An illumination section 20 is provided in the irradiation insertion section 3B as in the first embodiment, and is configured to apply light to a subject as in the first embodiment.

An image pickup unit storage portion 41 is provided at a distal end portion of a body 2. Disposed in the image pickup unit storage portion 41 are an image pickup unit 42, and a cover glass 43 provided to the distal direction side of the image pickup unit 42. An observation section 40 is provided in the observation insertion section 3A as a functional section. The observation section 40 includes an objective lens 45 configured to form a subject image, and a relay lens unit 46 provided to the proximal direction side of the objective lens 45. The subject image formed by the objective lens 45 is guided to the image pickup unit 42 by the relay lens unit 46. The image pickup unit 42 includes an image pickup element (not shown), and is configured to pick up the subject image guided by the relay lens unit 46. One end of an imaging cable 13 is connected to the image pickup unit 42, in the same manner as the image pickup unit 12 according to the first embodiment.

The observation insertion section 3A and the irradiation insertion section 3B are removably coupled to the body 2. Here, a coupling structure of the insertion sections 3A and 3B and the body 2 is described. It should be noted that the coupling structure of the observation insertion section 3A and the body 2 is described below. The coupling structure of the irradiation insertion section 3B and the body 2 is similar to the coupling structure of the observation insertion section 3A and the body 2, and is therefore not described.

FIG. 5 is a diagram illustrating the coupling structure of the observation insertion section 3A and the body 2. As shown in FIG. 4 and FIG. 5, a cylindrical connection portion 51 is provided at the proximal end portion of the observation insertion section 3A. The observation insertion section 3A is coupled to the body 2 by an insertion of the connection portion 51 into the image pickup unit storage portion 41 of the body 2. A recess 52 is provided in an outer peripheral surface of the connection portion 51.

A click ball 53 is provided in the body 2. The click ball 53 includes a ball portion 55 and a spring portion 56. If the connection portion 51 of the observation insertion section 3A is inserted into the image pickup unit storage portion 41, the ball portion 55 of the click ball 53 is locked to the recess 52 of the connection portion 51. This regulates the movement of the observation insertion section 3A in the longitudinal directions relative to the body 2. An click release dial 58 is provided in the body 2. By an operation in the click release dial 58, the elastic force of the spring portion 56 of the click ball 53 is diminished, and the ball portion 55 is unlocked from the recess 52 of the connection portion 51. If the connection portion 51 is removed from the image pickup unit storage portion 41 in this condition, the observation insertion section 3A is separated from the body 2. As described above, the connection portion 51, the click ball 53, and the click release dial 58 serve as a coupling unit configured to removably couple the observation insertion section 3A to the body 2.

Accordingly, the rigid endoscope 1 having the configuration described above provides the following advantageous effects in addition to the advantageous effects similar to those according to the first embodiment. That is, in the rigid endoscope 1 according to the present embodiment, the image pickup unit 42 is provided in the image pickup unit storage portion 41 of the body 2. The observation section 40 provided in the observation insertion section 3A includes the relay lens unit 46 configured to guide the subject image formed by the objective lens 45 to the image pickup unit 42. The image pickup unit 42 having a high image quality is increased in size, and therefore cannot be stored in the observation insertion section 3A having a small outside diameter. Therefore, the image pickup unit 42 is provided in the body 2, and the relay lens unit 46 is provided in the observation insertion section 3A, so that the image pickup unit 42 having a high image quality can be applied to the rigid endoscope 1.

Furthermore, in the rigid endoscope 1, the coupling unit configured to removably couple the insertion portions 3A and 3B to the body 2 is provided. The insertion sections 3A and 3B are removable from the body 2, so that the insertion sections 3A and 3B can be inexpensively and easily exchanged when the insertion sections 3A and 3B are damaged. Moreover, each of the insertion sections 3A and 3B can be easily used according to the situation. For example, the insertion sections 3A and 3B can be easily exchanged between direct view observation and oblique view observation.

Modification of Second Embodiment

Figure 6:
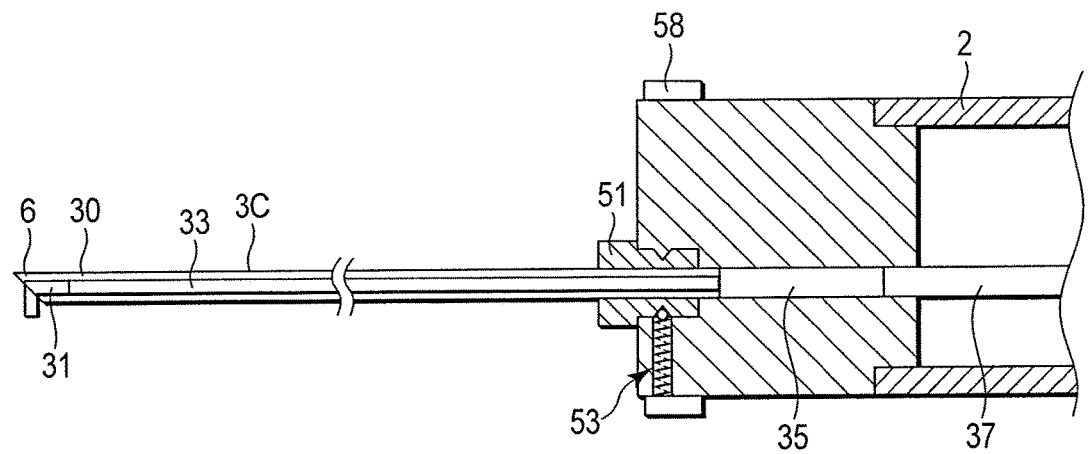
FIG. 6 is a sectional view schematically showing an internal structure of a rigid endoscope according to a modification of the second embodiment.

Although the two insertion sections 3A and 3B are removably coupled to the body 2 in the second embodiment, the present invention is not limited thereto. That is, it is only necessary to provide a configuration including a coupling unit configured to removably couple at least one insertion section (the insertion sections 3A and 3B in the second embodiment) to the body 2. For example, as a modification, an air/water supply insertion section 3C including an air/water supply section 30 may be removably coupled to the body 2. In this case, as shown in FIG. 6, an air/water supply passage 33 having one end in communication with an air/water supply nozzle 31 is provided in the air/water supply insertion section 3C. When the air/water supply insertion section 3C is coupled to the body 2, the other end of the air/water supply passage 33 is in communication with an intermediary passage 35 provided at the distal end portion of the body 2. One end of an air/water supply tube 37 is coupled to the intermediary passage 35. The other end of the air/water supply tube 37 is connected to an air/water supply unit (not shown). As described above, at least one of the first insertion section (e.g. 3A) and the second insertion section (e.g. 3B or 3C) has only to be removable from the body 2.

Although the connection portion 51, the click ball 53, and the click release dial 58 serve as the coupling unit configured to removably couple the insertion sections 3A and 3B to the body 2 in the second embodiment, the configuration of the coupling unit is not limited thereto.

Third Embodiment

Now, a third embodiment of the present invention will be described with reference to FIG. 7. In the third embodiment, the configuration according to the second embodiment is modified as follows. The same components as those in the second embodiment are provided with the same reference signs and are not described.

Figure 7:
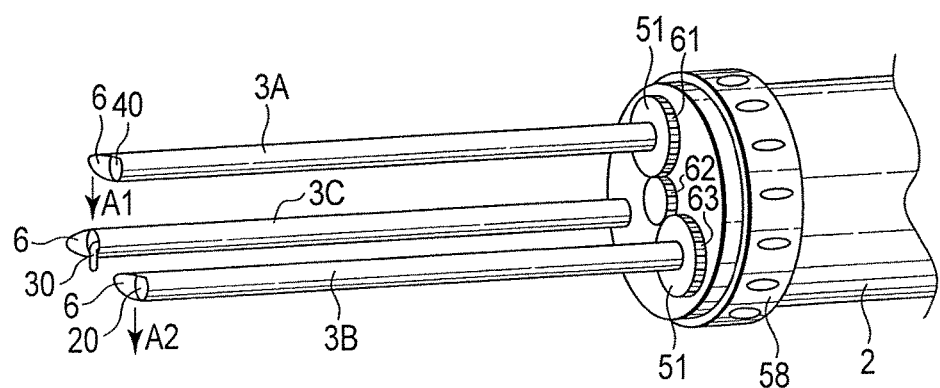
FIG. 7 is a perspective view schematically showing a rigid endoscope according to a third embodiment of the present invention.

FIG. 7 is a diagram showing a rigid endoscope according to the present embodiment. As shown in FIG. 7, in the rigid endoscope 1, insertion sections 3A and 3B are coupled to a body 2 by a coupling unit similar to that according to the second embodiment. The insertion sections 3A and 3B are coupled to the body 2 rotatably in directions around the axis. That is, the observation insertion section 3A and the irradiation insertion section 3B serve as rotary insertion sections rotatable in directions around the axis relative to the body 2. Here, an observation section 40 of the observation insertion section 3A is configured to perform oblique view observation.

A first gear portion 61 is provided in an outer peripheral surface of a connection portion 51 of the observation insertion section 3A (first insertion section). An idle gear portion 62 is provided in a distal surface body 2. The idle gear portion engages with the first gear portion 61, and rotates in a direction opposite to the first gear portion 61. A second gear portion 63 is provided in an outer peripheral surface of the connection portion 51 of the irradiation insertion section 3B (second insertion section). The second gear portion 63 engages with the idle gear portion 62, and rotates at the same rotation rate and in the same direction as the first gear portion 61.

In such a configuration, the first gear portion 61 rotates in directions around the axis integrally with the observation insertion section 3A when the observation insertion section 3A is rotated in the directions around the axis relative to the body 2. In response to the rotation of the first gear portion 61, the idle gear portion 62 rotates in a direction opposite to the first gear portion 61, and the second gear portion 63 rotates in the same direction and in the same amount as the first gear portion 61. As a result, the irradiation insertion section 3B rotates in the directions around the axis in the same direction and in the same amount as the observation insertion section 3A. Therefore, an adjustment is made so that an observation direction (a direction of an arrow A1 in FIG. 7) of the observation section 40 of the observation insertion section 3A corresponds to a illumination direction (a direction of an arrow A2 in FIG. 7) of the illumination section 20 of the irradiation insertion section 3B. That is, the first gear portion 61, the idle gear portion 62, and the second gear portion 63 serve as direction adjustment portion configured to rotate the irradiation insertion section 3B in directions around the axis in the same direction and in the same amount as the observation insertion section 3A so that the observation direction of the observation section 40 corresponds to the illumination direction of the illumination section 20.

Accordingly, the rigid endoscope 1 having the configuration described above provides the following advantageous effects in addition to the advantageous effects similar to those according to the second embodiment. That is, the rigid endoscope 1 according to the present embodiment is provided with the direction adjustment portion configured to rotate the irradiation insertion section 3B in the directions around the axis in the same direction and in the same amount as the observation insertion section 3A in response to the rotation of the observation insertion section 3A in the directions around the axis. Therefore, an adjustment is made so that the observation direction of the observation section 40 corresponds to the illumination direction of the illumination section 20. That is, the illumination direction of the illumination section 20 can be easily changed in accordance with the observation direction of the observation section 40.

Modification of Third Embodiment

In the third embodiment, the first gear portion 61, the idle gear portion 62, and the second gear portion 63 serve as the direction adjustment portion configured to rotate the irradiation insertion section 3B in the directions around the axis in the same direction and in the same amount as the observation insertion section 3A in response to the rotation of the observation insertion section 3A in the directions around the axis, and configured to make an adjustment so that the observation direction of the observation section 40 corresponds to the illumination direction of the illumination section 20. However, the direction adjustment portion is not limited to this configuration.

Although the insertion sections 3A and 3B are formed removably from the body 2 in the third embodiment, the present invention is not limited thereto. For example, as a modification, it is possible to provide a configuration provided with no coupling unit configured to removably couple the insertion sections 3A and 3B to the body 2. In this case as well, as in the third embodiment, each of the insertion sections 3A and 3B is rotatable in the directions around the axis relative to the body 2.

Furthermore, although each of the insertion sections 3A and 3B is rotatable in the directions around the axis relative to the body 2 in the third embodiment, the present invention is not limited thereto. For example, as a modification, an air/water supply insertion section 3C including an air/water supply section 30 may be rotatable in the directions around the axis relative to the body 2. Therefore, at least one insertion section (the insertion sections 3A and 3B in the third embodiment) has only to be the rotary insertion section rotatable in the directions around the axis relative to the body 2. That is, at least one of the first insertion section (e.g. 3A) and the second insertion section (e.g. 3B) has only to be the rotary insertion sections rotatable in the directions around the axis relative to the body 2.

Fourth Embodiment

Now, a fourth embodiment of the present invention will be described with reference to FIG. 7. In the fourth embodiment, the configuration according to the first embodiment is modified as follows. The same components as those in the first embodiment are provided with the same reference signs and are not described.

Figure 8:
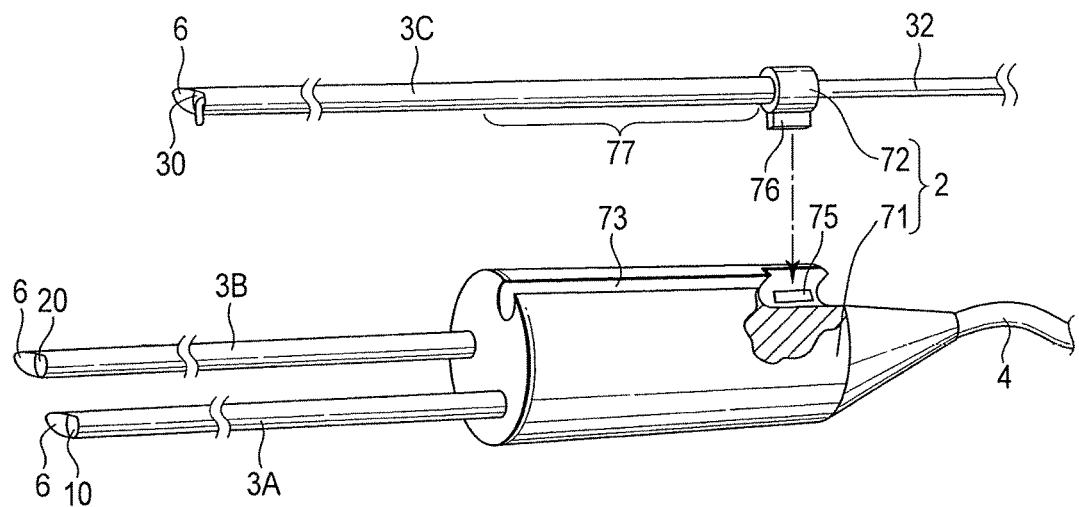
FIG. 8 is a perspective view schematically showing, partially in section, the separated condition of a first formation and a second formation of a body of a rigid endoscope according to a fourth embodiment of the present invention.
Figure 9:
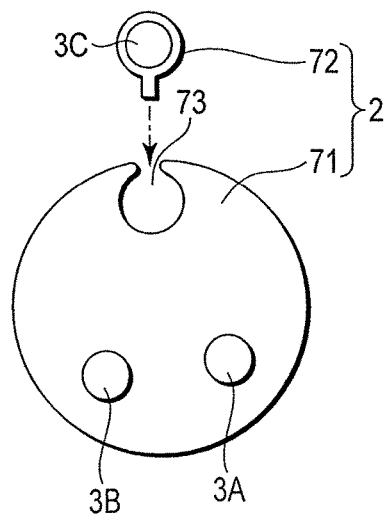
FIG. 9 is a schematic view showing, from a distal direction, the separated condition of the first formation and the second formation of the body of the rigid endoscope according to the fourth embodiment.

FIG. 8 and FIG. 9 are diagrams showing the configuration of a rigid endoscope 1 according to the present embodiment. As shown in FIG. 8 and FIG. 9, a body 2 includes a first formation 71, and a second formation 72 removably attached to the first formation 71. One end of a universal cord 4 is connected to a proximal end portion of the first formation 71. An observation insertion section 3A provided with an observation section 10 and an irradiation insertion section 3B provided with an illumination section 20 extend toward the distal direction from the first formation 71. The first formation is provided with a groove 73 along the longitudinal directions. A recess 75 is provided in a bottom surface of the groove 73.

The second formation 72 includes a projection 76 which engages with the recess 75 of the first formation 71. When the projection 76 engages with the recess 75, the second formation 72 is attached to the first formation 71 so that the second formation 72 is positioned in the longitudinal directions. That is, the recess 75 and the projection 76 serve as positioning portion configured to attach the second formation 72 to the first formation 71 so that the second formation 72 is positioned in the longitudinal directions. An air/water supply insertion section 3C provided with an air/water supply section 30 extends toward the distal direction from the second formation 72. A stored portion 77, to be stored in the groove 73 of the first formation 71 in a state that the second formation 72 is attached to the first formation 71, is provided at a proximal end portion of the air/water supply insertion section 3C. As in the first embodiment, the air/water supply section 30 includes an air/water supply nozzle 31 provided at the distal end supply insertion section 3C. One end of an air/water supply tube 32 is connected to the proximal end of the air/water supply nozzle 31. The air/water supply tube 32 extends to an outside from a proximal end portion of the second formation 72 through the air/water supply insertion section 3C and the second formation 72. As in the first embodiment, the other end of the air/water supply tube 32 is connected to an air/water supply unit (not shown) which is one of peripheral units.

Accordingly, the rigid endoscope 1 having the configuration described above provides the following advantageous effects in addition to the advantageous effects similar to those according to the first embodiment. That is, in the rigid endoscope 1 according to the present embodiment, the body 2 includes the first formation 71, and the second formation 72 removably attached to the first formation 71. The air/water supply insertion section 3C provided with the air/water supply section 30 extends toward the distal direction from the second formation 72. As the air/water supply insertion section 3C is provided with air/water supply conduits such as the air/water supply nozzle 31 and the air/water supply tube 32, cleaning and sterilization are difficult after the use of the rigid endoscope 1. Therefore, the second formation 72 is removable from the first formation 71 so that the insertion sections 3A and 3B extending toward the distal direction from the first formation 71 are cleaned and sterilized after the use of the rigid endoscope 1 and are reused. That is, the insertion sections 3A and 3B serve as reuse insertion sections (first insertion sections) configured to be cleaned and sterilized after use and configured to be reused. On the other hand, the air/water supply insertion section 3C and the second formation 72, which are difficult to clean and sterilize, are disposed of after use. That is, the insertion section 3C serves as a disposable insertion section (second insertion section) configured to be disposed of after use. Consequently, the insertion section 3C which is difficult to clean and sterilize is disposed of, and the other insertion sections 3A and 3B can be effectively reused.

Fifth Embodiment

Now, a fifth embodiment of the present invention will be described with reference to FIG. 10 to FIG. 12. In the fifth embodiment, the configuration according to the fourth embodiment is modified as follows. The same components as those in the fourth embodiment are provided with the same reference signs and are described.

Figure 10:
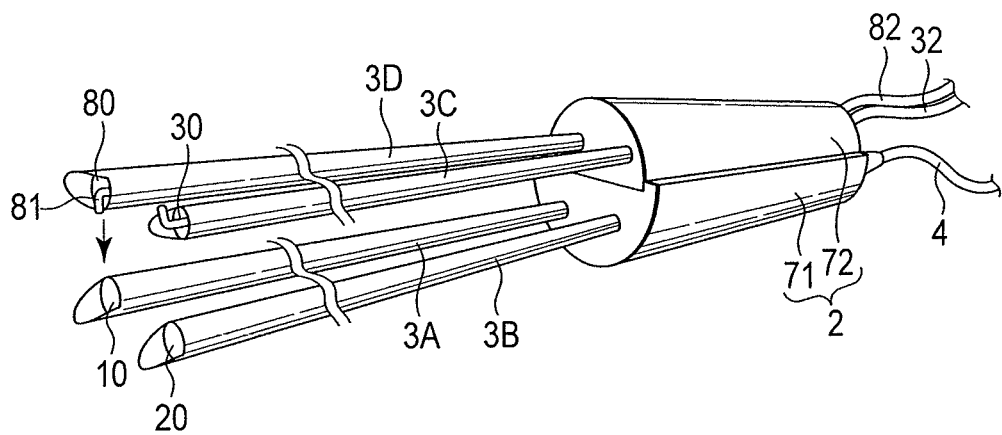
FIG. 10 is a perspective view schematically showing the coupled condition of a first formation and a second formation of a rigid endoscope according to a fifth embodiment of the present invention.

FIG. 10 is a diagram showing a rigid endoscope 1 according to the present embodiment. As shown in FIG. 10, a body 2 includes a first formation 71 and second formation 72 as in the fourth embodiment. As in the fourth embodiment, an observation insertion section 3A provided with an observation section 10 and an irradiation insertion section 3B provided with an illumination section 20 extend toward the distal direction from the first formation 71, and an air/water supply insertion section 3C provided with an air/water supply section 30 extends toward the distal direction from the second formation 72.

In the present embodiment, a cleaning insertion section 3D extends in the longitudinal directions toward the distal direction from the second formation 72. The cleaning insertion section 3D is provided with a cleaning section 80 as a functional section. The cleaning section 80 is configured to clean an objective lens 11 of the observation section 10. The cleaning section 80 includes a cleaning water nozzle 81 provided at a distal end portion of the cleaning insertion section 3D. A direction of the cleaning water nozzle 81 is adjusted to blow cleaning water toward the objective lens 11 (the observation section 10). One end of a cleaning water tube 82 is connected to a proximal end of the cleaning water nozzle 81. The cleaning water tube 82 extends to the outside from a proximal end portion of the second formation 72 through the cleaning insertion section 3D and the second formation 72. The other end of the cleaning water tube 82 is connected to a water supply unit (not shown) which is one of peripheral units.

Figure 11:
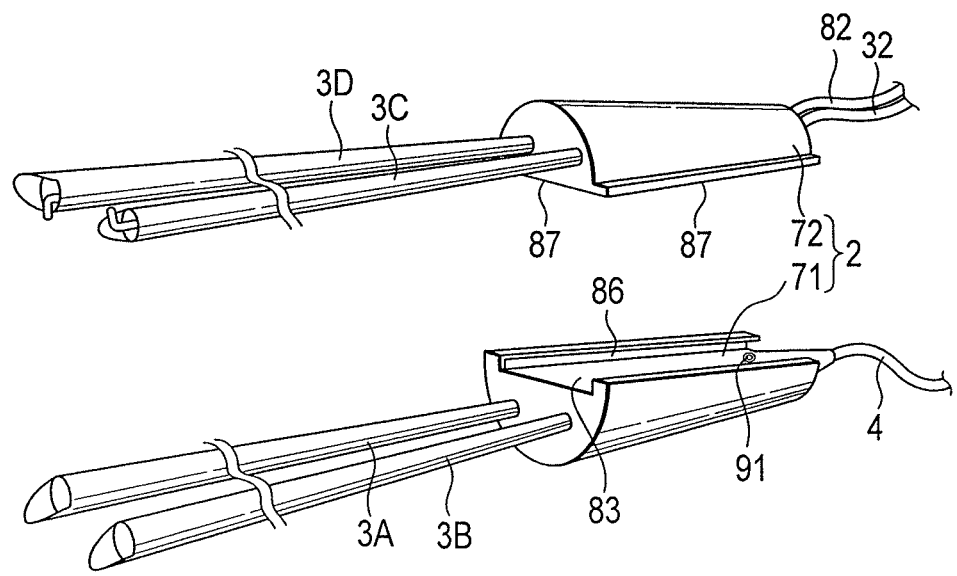
FIG. 11 is a perspective view schematically showing the separated condition of the first formation and the second formation of the rigid endoscope according to the fifth embodiment.

FIG. 11 and FIG. 12 are diagrams showing an attachment/detachment structure of the first formation 71 and the second formation 72. As shown in FIG. 11 and FIG. 12, the first formation 71 is provided with groove 83 along the longitudinal directions. Rail guides 86 are provided on both sides of the groove 83 along the longitudinal directions. Rails 87 are provided on both sides of the second formation 72 along the longitudinal directions. Each of the rails 87 can engage with the corresponding rail guide 86. The second formation 72 moves in the longitudinal directions relative to the first formation 71 while each of the rails 87 is engaged with the corresponding rail guide 86.

A click ball 91 is provided in a bottom surface of the groove 83. The click ball 91 includes a ball portion 92 and a spring portion 93. A depression 95 is provided in s lower surface of the second formation 72. If the second formation 72 is moved from a proximal end of the first formation 71 toward the distal direction, the ball portion 92 of the click ball 91 is locked to the depression 95 of the second formation 72. This regulates the movement of the second formation 72 in the longitudinal directions relative to the first formation 71, and the second formation 72 is attached to the first formation 71 so that the second formation 72 is positioned in the longitudinal directions. That is, the click ball 91 and the depression 95 serve as positioning portion configured to attach the second formation 72 to the first formation 71 so that the second formation 72 is positioned in the longitudinal directions.

Accordingly, the rigid endoscope 1 having the configuration described above provides the following advantageous effects in addition to the advantageous effects similar to those according to the fourth embodiment. That is, in the rigid endoscope 1 according to the present embodiment, the air/water supply insertion section 3C provided with the air/water supply section 30 and the cleaning insertion section 3D provided with the cleaning section 80 extend toward the distal direction from the second formation 72. As the cleaning insertion section 3D is provided with water supply conduits such as the cleaning water nozzle 81 and the cleaning water tube 82, cleaning and sterilization are difficult after the use of the rigid endoscope 1 as in the case of the air/water supply insertion section 3C. Therefore, the second formation 72 is removable from the first formation 71 so that the insertion sections 3A and 3B extending toward the distal direction from the first formation 71 are cleaned and sterilized after the use of the rigid endoscope 1 and are reused. On the other hand, the insertion sections 3C and 3D and the second formation 72, which are difficult to clean and sterilize, are disposed of as one unit after use. Consequently, even if there are a plurality of insertion sections 3C and 3D configured to be disposed of after use, these insertion sections can be separated as one unit from the insertion sections 3A and 3B configured to be reused after use.

Modification of Fourth Embodiment and Fifth Embodiment

Although the observation insertion section 3A provided with the observation section 10 and the irradiation insertion section 3B provided with the illumination section 20 extend toward the distal direction from the first formation in the fourth embodiment and the fifth embodiment, the present invention is not limited thereto. Moreover, in the fourth embodiment, the air/water supply insertion section 3C provided with the air/water supply section 30 extend toward the distal direction from the second formation 72. In the fifth embodiment, the air/water supply insertion section 3C, and the cleaning insertion section 3D provided with the cleaning section 80 extend toward the distal direction from the second formation 72. However, the present invention is not limited thereto. That is, at least one reuse insertion section (the insertion sections 3A and 3B in the fifth embodiment) configured to be reused by cleaning and sterilization among a plurality of insertion sections (the insertion sections 3A to 3D in the fifth embodiment) has only to extend toward the distal direction from the first formation 71. Moreover, at least one disposable insertion section (the insertion sections 3C and 3D in the fifth embodiment) configured to be disposed of after use among a plurality of insertion sections (the insertion sections 3A to 3D in the fifth embodiment) has only to extend toward the distal direction from the second formation 72.

The recess 75 and the projection 76 in the fourth embodiment and the click ball 91 and the depression 95 in the fifth embodiment serve as the positioning portion configured to attach the second formation 72 to the first formation 71 so that the second formation 72 is positioned in the longitudinal directions. However, the present invention is not limited thereto. That is, the positioning portion has only to be provided to attach the second formation 72 to the first formation 71 so that the second formation 72 is positioned in the longitudinal directions.

Sixth Embodiment

Now, a sixth embodiment of the present invention will be described with reference to FIG. 13. In the sixth embodiment, the configuration according to the first embodiment is modified as follows. The same components as those in the first embodiment are provided with the same reference signs and are not described.

A rigid endoscope 1 according to the present embodiment includes an observation insertion section 3A (first insertion section), and a cleaning insertion section 3D (second insertion section) described above in the fifth embodiment. The cleaning insertion section 3D is provided with a cleaning section 80 configured to clean an objective lens 11 of an observation section 10. The configuration of the cleaning insertion section 3D and the function of the cleaning section 80 are similar to those according to the fifth embodiment.

FIG. 13 is a diagram showing the configuration of the distal end portions of the observation insertion section 3A and the cleaning insertion section 3D. As shown in FIG. 13, needles 6 are provided at the distal end portions of the observation insertion section 3A and the cleaning insertion section 3D. The objective lens 11 is provided in the needle 6 of the observation insertion section 3A. As has been described above in the fifth embodiment, cleaning water is blown to the objective lens 11 from a cleaning water nozzle 81 provided at the distal end portion of the cleaning insertion section 3D (an arrow B in FIG. 13).

The inner peripheral surface of a part to the distal direction side of the objective lens 11 (the observation section 10) in the needle 6 of the observation insertion section 3A is substantially cylindrically shaped. Therefore, the cleaning water blown to the objective lens 11 from the cleaning water nozzle 81 tends to be collected in the inner peripheral surface of the part to the distal direction side of the observation section 10 in the needle 6 of the observation insertion section 3A. Thus, the needle 6 of the observation insertion section 3A includes a bore-like drain portion 97 provided in the part to the distal direction side of the observation section 10.

Accordingly, the rigid endoscope 1 having the configuration described above provides the following advantageous effects in addition to the advantageous effects similar to those according to the first embodiment. That is, in the rigid endoscope 1 according to the present embodiment, the needle 6 of the observation insertion section 3A includes the bore-like drain portion 97 provided in the part to the distal direction side of the observation section 10. The cleaning water blown to the objective lens 11 from the cleaning water nozzle 81 of the cleaning section 80 tends to be collected in the inner peripheral surface of the needle 6 of the observation insertion section 3A located to the distal direction side of the observation section 10. Thus, the drain portion 97 is provided to prevent the cleaning water from being collected in the inner peripheral surface of the observation insertion section 3A located to the distal direction side of the objective lens 11 (the observation section 10). Consequently, a subject can be observed by the observation section 10 with a good field of view.

Seventh Embodiment

Now, a seventh embodiment of the present invention will be described with reference to FIG. 14 and FIG. 15. In the seventh embodiment, the configuration according to the first embodiment is modified as follows. The same components as those in the first embodiment are provided with the same reference signs and are not described.

FIG. 14 and FIG. 15 are diagrams showing the configuration of a distal end portion of an irradiation insertion section 3B of a rigid endoscope 1 according to the present embodiment. As shown in FIG. 14 and FIG. 15, the irradiation insertion section 3B is provided with a movable member 101 movable in the longitudinal directions relative to a needle 6. An illumination section 20 which is a functional section is stored in the movable member 101. The illumination section 20 moves in the longitudinal directions relative to the needle 6 integrally with the movable member 101. An outside diameter of the movable member 101 is smaller than an inside diameter of the needle 6. One end of an urging member 102 such as a compression spring is connected to s proximal end of the movable member 101. The other end of the urging member 102 is connected to a protrusion 103 protruding from the inner peripheral surface of the irradiation insertion section 3B toward the inner peripheral side.

In such a configuration, the movable member 101 moves in the longitudinal directions between a first position (see FIG. 15) where a distal end of the movable member 101 is located to the distal direction side of a distal end of the needle 6 and a second position (see FIG. 14) where the distal end of the movable member 101 is located to the proximal direction side of the distal end of the needle 6. When no force is applied from the distal side, the movable member 101 is urged toward the distal direction by the urging member 102 to be located at the first position. When the force is applied to the movable member 101 from the distal direction, the movable member 101 moves toward the proximal direction against the urging by the urging member 102. As a result, the movable member 101 is stored in the needle 6, and moves to the second position. The movable member 101 moves between the first position and the second position and the shape of the distal end of the irradiation insertion section 3B changes accordingly. That is, the irradiation insertion section 3B serves as a shape changeable insertion section configured to change the shape of its distal end when force is applied thereto from the distal direction.

When the irradiation insertion section 3B is inserted into a body cavity, the distal end of the movable member 101 bumps into a body wall 105 in a state that the movable member 101 is located at the first position. As the movable member 101 bumps into the body wall 105, force is applied to the irradiation insertion section 3B from the distal direction as shown in FIG. 14, and the movable member 101 moves toward the proximal direction against the urging by the urging member 102. As a result, the movable member 101 is stored in the needle 6, and moves to the second position where the distal end of the movable member 101 is located to the proximal direction side of the distal end of the needle 6. Further, as shown in FIG. 15, when the needle 6 is inserted into the body cavity through the sticking point of the body wall 105, no force is applied to the irradiation insertion section 3B from the distal direction. As a result, the movable member 101 is urged by the urging member 102 to move to the first position where the distal end of the movable member 101 is located to the distal direction side of the distal end of the needle 6.

Accordingly, the rigid endoscope 1 having the configuration described above provides the following advantageous effects in addition to the advantageous effects similar to those according to the first embodiment. That is, the rigid endoscope 1 according to the present embodiment includes the movable member 101 which moves in the longitudinal directions between the first position where the distal end of the movable member 101 is located to the distal direction side of the distal end of the needle 6 and the second position where the distal end of the movable member 101 is located to the proximal direction side of the distal end of the needle 6. When no force is applied from the distal direction, the movable member 101 is urged toward the distal direction by the urging member 102 to be located at the first position. Therefore, no force is applied to the irradiation insertion section 3B from the distal direction except when the needle 6 passes through the sticking point of the body wall 105, so that the movable member 101 is located at the first position. This can prevent a living tissue from being damaged by the needle 6 in parts other than the sticking point of the body wall 105.

Modification of Seventh Embodiment

Although the irradiation insertion section 3B is provided with the movable member 101 and the urging member 102 in the seventh embodiment, the present invention is not limited thereto. For example, as a modification, an air/water supply insertion section 3C may be provided with the movable member 101 storing an air/water supply section 30, and the urging member 102. Therefore, at least one insertion section (the insertion section 3B in the present embodiment) has only to be the shape changeable insertion section which is configured to change the shape of its distal end when force is applied thereto from the distal direction, and has only to includes the movable member 101 and the urging member 102. That is, at least one of the first insertion section (e.g. 3B) and the second insertion section (e.g. 3A) has only to be the shape changeable insertion section which is configured to change the shape of its distal end when force is applied thereto from the distal direction.

Eighth Embodiment

Now, an eighth embodiment of the present invention will be described with reference to FIG. 16 and FIG. 17. In the eighth embodiment, the configuration according to the seventh embodiment is modified as follows. The same components as those in the seventh embodiment are provided with the same reference signs and are not described.

FIG. 16 and FIG. 17 are diagrams showing the configurations of the distal end portions of insertion sections 3A to 3D according to the present embodiment. As shown in FIG. 16 and FIG. 17, a rigid endoscope 1 is provided with an observation insertion section 3A including an observation section 10, an irradiation insertion section 3B including an illumination section 20, an air/water supply insertion section 3C including an air/water supply section 30, and a cleaning insertion section 3D including a cleaning section 80. In the rigid endoscope 1, each of the insertion sections 3B to 3D other than the observation insertion section 3A includes a movable member 101 and an urging member 102 similar to those in the seventh embodiment. That is, each of the insertion sections 3B to 3D serves as a shape changeable insertion section which is configured to change the shape of its distal end when force is applied thereto from the distal direction. The observation insertion section 3A (first insertion section) including an image pickup unit 12 in the observation section 10 which is a functional section is neither provided with a movable member 101 nor an urging member 102.

The image pickup unit 12 of the observation section 10 is larger in size than members provided in other functional sections (20, 30, and 80) such as a light guide portion 21. Accordingly, the observation insertion section 3A is larger in outside diameter than the other insertion sections 3B to 3D. Therefore, if the observation insertion section 3A is provided with the movable member 101 storing the observation section 10, the outside diameter of a needle 6 storing the movable member 101 is further increased by the thickness of the movable member 101. Thus, from the viewpoint of the invasive degree during the insertion of the observation insertion section 3A into a body cavity, it is preferable that the observation insertion section 3A is not provided with the movable member 101 and the urging member 102.

Accordingly, in the present embodiment, the insertion sections 3B to 3D provided with the movable members 101 and the urging members 102 are arrayed around the observation insertion section 3A in directions around the axis of the observation insertion section 3A. That is, the insertion sections 3B to 3D serve as array insertion sections (second insertion sections) arrayed around the observation insertion section 3A in the directions around the axis of the observation insertion section 3A. When no force is applied to each of the insertion sections 3B to 3D from the distal direction, the distal end of the movable member 101 of each of the insertion sections 3B to 3D is located to the distal direction side of the distal end of the needle 6 of the observation insertion section 3A. The four insertion sections 3A to 3D are end of the movable member 101 of one of the insertion sections 3B to 3D bumps into, example, a living tissue before the distal end of the needle 6 of the observation insertion section 3A bumps into, for example, the living tissue.

Accordingly, the rigid endoscope 1 having the configuration described above provides the following advantageous effects in addition to the advantageous effects similar to those according to the seventh embodiment. That is, in the rigid endoscope 1 according to the present embodiment, the insertion sections 3B to 3D provided with the movable members 101 and the urging members 102 are arrayed around the observation insertion section 3A in the directions around the axis of the observation insertion section 3A. When no force is applied to each of the insertion sections 3B to 3D from the distal direction, the distal end of the movable member 101 of each of the insertion sections 3B to 3D is located to the distal directions side of the distal end of the needle 6 of the observation insertion section 3A. The four insertion sections 3A to 3D are thus arranged so that when no force is applied thereto from the distal direction, the distal end of the movable member 101 of one of the insertion sections 3B to 3D bumps into, for example, a living tissue before the distal end of the needle 6 of the observation insertion section 3A bumps into, for example the living tissue. This can prevent the living tissue from being damaged by the needle 6 of the observation insertion section 3A in parts other than a sticking point of a body wall. As the observation insertion section 3A is not provided with the movable member 101 and the urging member 102, it is possible to prevent the increase in the outside diameter of the needle 6 of the observation insertion section 3A.

Modification of Eighth Embodiment

Although the insertion sections 3B to 3D are provided with the movable members 101 and the urging members 102 in the eighth embodiment, the present invention is not limited thereto. That is, the observation insertion section 3A has only to be provided with the image pickup unit 12, and a plurality of insertion sections (the insertion sections 3B to 3D in the eighth embodiment) other than the observation insertion section 3A (first insertion section) have only to be shape changeable insertion sections (second insertion sections) which are provided with the movable members 101 and the urging members 102. In this case, the shape changeable insertion sections includes a plurality of array insertion sections (the insertion sections 3B to 3D in the eighth embodiment) arrayed around the observation insertion section 3A in the directions around the axis of the observation insertion section 3A. When no force is applied from the distal direction, the distal end of the movable member 101 of each of the array insertion sections is located to the distal direction side of the distal end of the needle 6 of the observation insertion section 3A.

Ninth Embodiment

Now, a ninth embodiment of the present invention will be described with reference to FIG. 18 to FIG. 20. In the ninth embodiment, the configuration according to the first embodiment is modified as follows. The same components as those in the first embodiment are provided with the same reference signs and are not described.

FIG. 18 and FIG. 19 are diagrams showing a rigid endoscope 1 according to the present embodiment. As in FIG. 18 and FIG. 19, endoscope 1 includes a body 2, and three insertion sections 3A to 3C as in the first embodiment. The insertion sections 3A to 3C are located substantially 120° apart from one another in the circumferential directions of the body 2 when viewed from the distal side in the longitudinal directions. That is, the insertion sections 3A to 3C are arrayed in the circumferential directions of the body 2. If the observation insertion section 3A (first insertion section) is a standard, the insertion sections 3B and 3C (second insertion sections) serve as adjacent insertion sections adjacent to the observation insertion sections 3A in the circumferential directions of the body 2.

Here, a dimension of a space between the distal end of a needle 6 of the observation insertion section 3A and the distal end of a needle 6 of the irradiation insertion section 3B in directions perpendicular to the longitudinal directions is x1. A dimension of a space between the distal end of the needle 6 of the irradiation insertion section 3B and the distal end of a needle 6 of the air/water supply insertion section 3C in the directions perpendicular to the longitudinal directions is x2. A dimension of a space between the distal end of the needle 6 of the air/water supply insertion section 3C and the distal end of the needle 6 of the observation insertion section 3A in the directions perpendicular to the longitudinal directions is x3. In the rigid endoscope 1, all of the dimensions x1, x2, and x3 are 2 mm or more and 10 mm or less. That is, the insertion sections 3A to 3C only consists of the single standard observation insertion section 3A (first insertion section), and at least one insertion section 3B and 3C (second insertion section) having the distal end of the needle 6 located a dimension of 2 mm or more and 10 mm or less apart from the distal end of the needle 6 of the observation insertion section 3A in the directions perpendicular to the longitudinal directions.

Figures 20, 21:
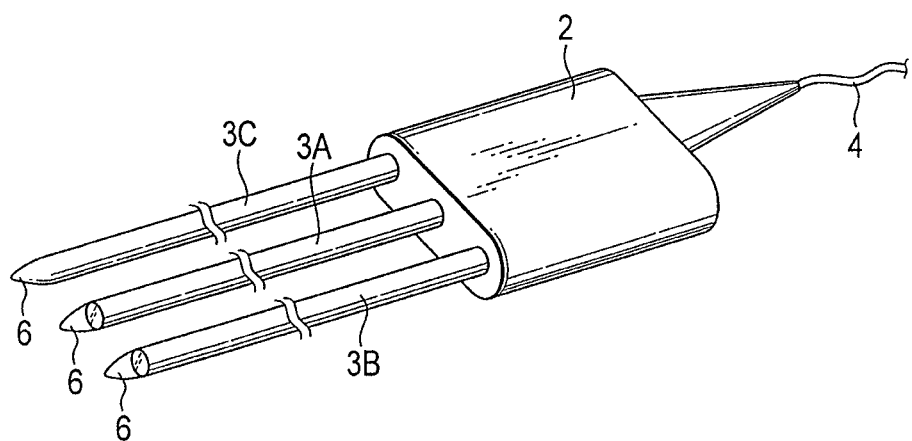
FIG. 20 is a schematic diagram showing experimental data regarding the relationship between dimensions of each of spaces between distal ends of needles of insertion sections in the rigid endoscope according to the ninth embodiment and an amount of sticking power.
FIG. 21 is a perspective view schematically showing a rigid endoscope according to a tenth embodiment of the present invention.

FIG. 20 is a table showing experimental data regarding the relationship between the dimensions x1, x2, and x3 and an amount of sticking power to stick the insertion sections 3A to 3C into a body wall. Here on the condition that x1=x2=x3, the dimensions x1, x2, and x3 are changed, and the amount of sticking power is then measured. As shown in FIG. 20, the amount of sticking power is 100 N when the dimensions x1, x2, and x3 are 1 mm, whereas the amount of sticking power is 80 N and is reduced when the dimensions x1, x2, and x3 are 3 mm. When the dimensions x1, x2, and x3 are 5 mm, the amount of sticking power is 60 N and is further reduced. When the dimensions x1, x2, and x3 are small (when the dimensions x1, x2, and x3 are 1 mm), a bore made at the sticking point where the needle 6 of the observation insertion section 3A is stuck into the body wall is not separated by the body wall from bores made at the sticking points where the needles 6 of the other insertion sections 3B and 3C are stuck into the body wall. That is, the bore made at the sticking point where the needle 6 of the observation insertion section 3A is stuck into the body wall, the bore made at the sticking point where the needle 6 of the irradiation insertion section 3B is stuck into the body wall, and the bore made at the sticking point where the needle 6 of the air/water supply insertion section 3C is stuck into the body wall are formed to be in communication with one another. Therefore, when the dimensions x1, x2, and x3 are 1 mm, the amount of sticking power is increased. As the three bores made in the body wall are in communication with one another, the invasive degree is higher.

As shown in FIG. 20, the amount of sticking power is 40 N when the dimensions x1, x2 and x3 are 7 mm, whereas the amount of sticking power is 100 N and is increased when the dimensions x1, x2, and x3 are 15 mm. When the dimensions x1, x2, and x3 are large (when the dimensions x1, x2, and x3 are 15 mm), the inclinations of the insertion sections 3A to 3C in directions perpendicular to the body wall are increased. As the needles 6 of the insertion sections 3A to 3C considerably inclined in the directions perpendicular to the body wall are stuck into the body wall, the amount of sticking power is increased.

The experimental results described above show that it is proper to set all of the dimensions x1, x2, and x3 to a range of 2 mm or more to 10 mm or less. When all of the dimensions x1, x2, and x3 are set to a range of 2 mm or more to 10 mm or less, a user can stick the needles 6 of the insertion sections 3A to 3C into the body wall with a sufficiently small amount of sticking power.

Accordingly, the rigid endoscope 1 having the configuration described above provides the following advantageous effects in addition to the advantageous effects similar to those according to the first embodiment. That is, in the rigid endoscope 1 according to the present embodiment, all of the dimensions x1, x2, and x3 are 2 mm or more and 10 mm or less. Therefore, in contrast with the case where the dimensions x1, x2, and x3 are small (the dimensions x1, x2, and x3 are 1 mm), the needles 6 of the insertion sections 3A to 3C are stuck into the body wall so that the three bores made in the body wall are separated by the body wall. Moreover, in contrast with the case where the dimensions x1, x2, and x3 are large (the dimensions x1, x2, and x3 are 15 mm), the inclinations of the insertion sections 3A to 3C in the directions perpendicular to the body wall are not increased. Thus, the user can stick the needles 6 of the insertion sections 3A to 3C into the body wall with a sufficiently small amount of sticking power.

Tenth Embodiment

Now, a tenth embodiment of the present invention will be described with reference to FIG. 21 to FIG. 23. In the tenth embodiment, the configuration according to the ninth embodiment is modified as follows. The same components as those in the ninth embodiment are provided with the same reference signs and are not described.

Figures 22, 23:
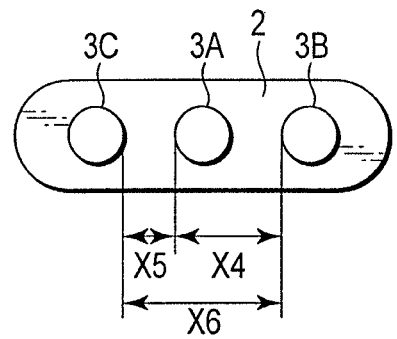
FIG. 22 is a schematic view showing the rigid endoscope according to the tenth embodiment from the distal direction.
FIG. 23 is a schematic diagram showing experimental data regarding the relationship between dimensions of each of spaces between the distal ends of needles of insertion sections in the rigid endoscope according to the tenth embodiment and the amount of sticking power.

FIG. 21 and FIG. 22 are diagrams showing a rigid endoscope 1 according to the present embodiment. As shown in FIG. 21 and FIG. 22, the rigid endoscope 1 includes a body 2, and three insertion sections 3A to 3C as in the ninth embodiment. The insertion sections 3A to 3C are arrayed in array directions which are specified directions perpendicular to the longitudinal directions. If the observation insertion section 3A (first insertion section) is a standard, the insertion sections 3B and 3C (second insertion sections) serve as adjacent insertion sections adjacent to the observation insertion section 3A in the array directions. If the irradiation insertion section 3B (first insertion section) is a standard, the insertion section 3A (near position insertion section) serves as an adjacent insertion section adjacent to the irradiation insertion section 3B in the array directions.

Here, a dimension of a space between the distal end of a needle 6 of the observation insertion section 3A and the distal end of a needle 6 of the irradiation insertion section 3B in the array directions is x4. A dimension of a space between the distal end of the needle 6 of the observation insertion section 3A and the distal end of a needle 6 of the air/water supply insertion section 3C in the array directions is x5. In the rigid endoscope 1, both of the dimensions x4 and x5 are 2 mm or more and 10 mm or less. That is, the insertion section only consist of the single standard observation insertion section 3A (first insertion section), and at least one insertion section 3B and 3C (second insertion section) having the distal end of the needle 6 located a dimension of 2 mm or more and 10 mm or less apart from the distal end of the needle 6 of the observation insertion section 3A in the array directions.

A dimension x6 of a space between the distal end of the needle 6 of the irradiation insertion section 3B and the distal end of the needle 6 of the air/water supply insertion section 3C in the array directions is more than 10 mm. That is, the insertion section 3A to 3C only consist of the standard irradiation insertion section 3B (first insertion section), and a plurality of insertion sections 3A and 3C (second insertion sections) located apart from the irradiation insertion section 3B in the directions perpendicular to the longitudinal directions. The insertion sections 3A and 3C only consist of the insertion section 3A (near position insertion section) having the distal end of the needle 6 located a dimension of 2 mm or more and 10 mm or less apart from the distal end of the needle of the irradiation insertion section 3B in the array directions, and the insertion section 3C (far position insertion section) having the distal end of the needle 6 located a dimension of more than 10 mm apart from the distal end of the needle 6 of the irradiation insertion section 33 in the array directions. The distal end of the needle 6 of the insertion section 3C (far position insertion section) is located a dimension of 2 mm or more and 10 mm or less apart from the distal end of the needle 6 of the insertion section 3A (near position insertion section) in the array directions.

FIG. 23 is a table showing experimental data regarding the relationship between the dimensions x4 and x5 and an amount of sticking power to stick the insertion sections 3A to 3C into a body wall. Here, on the condition that x4=x5, the dimensions x4 and x5 are changed, and the amount of sticking power is then measured. As shown in FIG. 23, in this experiment, the results similar to those in FIG. 20 in the ninth embodiment are obtained. This shows that it is proper to set both of the dimensions x4 and x5 to a range of 2 mm or more to 10 mm or less. When both of the dimensions x4 and x5 are in a range of 2 mm or more to 10 mm or less, the user can stick the needles 6 of the insertion sections 3A to 3C into the body wall with sufficiently small amount of sticking power.

Accordingly, the rigid endoscope 1 according to the present embodiment provides the advantageous effects similar to those according to the ninth embodiment because both of the dimensions x4 and x5 are 2 mm or more to 10 mm or less. That is, the user can stick the needles 6 of the insertion sections 3A to 3C into the body wall with a sufficiently small amount of sticking power.

Modification of Ninth Embodiment and Tenth Embodiment

Figure 24:
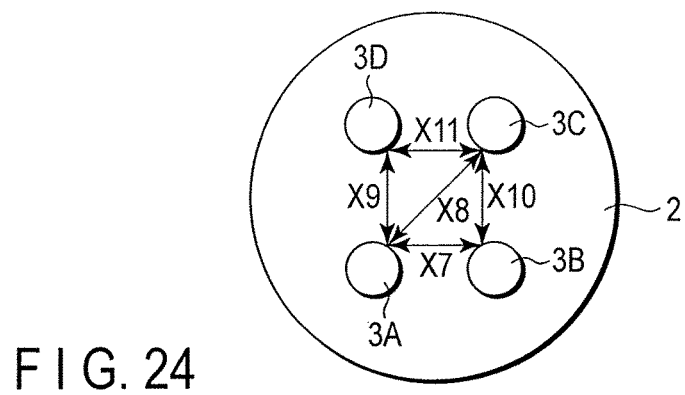
FIG. 24 is a schematic view showing a rigid endoscope according to a modification of the ninth embodiment from the distal direction.

Although the three insertion sections 3A to 3C are provided in the ninth embodiment, the present invention is as a not limited thereto. For example, modification, four insertion sections 3A to 3D may be arrayed in the circumferential directions of the body 2 as shown in FIG. 24. In the present modification, a dimension x7 of a space between the distal end of the needle 6 of the observation insertion section 3A and the distal end of the needle 6 of the irradiation insertion section 3B in the directions perpendicular to the longitudinal directions is 2 mm or more to 10 mm or less. A dimension x8 of a space between the distal end of the needle 6 of the observation insertion section 3A and the distal end of the needle 6 of the air/water supply insertion section 3C in the directions perpendicular to the longitudinal directions is more than 10 mm. A dimension x9 of a space between the distal end of the needle 6 of the observation insertion section 3A and the distal end of the needle 6 of the cleaning insertion section 3D in the directions perpendicular to the longitudinal directions is 2 mm or more to 10 mm or less. A dimension x10 of a space between the distal end of the needle 6 of the irradiation insertion section 3B and the distal end of the needle 6 of the air/water supply insertion section 3C in the directions perpendicular to the longitudinal directions is 2 mm or more to 10 mm or less. A dimension x11 of a space between the distal end of the needle 6 of the air/water supply insertion section 3C and the distal end of the needle 6 of the cleaning insertion section 3D in the directions perpendicular to the longitudinal directions is 2 mm or more to 10 mm or less. That is, the insertion sections 3A to 3D only consists of the single standard observation insertion section 3A (first insertion section); and a plurality of insertion sections 3B to 3D (second insertion sections). The insertion sections 3B to 3D (second insertion sections) only consist of the insertion sections 3B and 3D (near position insertion sections) each of which has the distal end of the needle 6 located a dimension of 2 mm or more and 10 mm or less apart from the distal end of the needle 6 of the observation insertion section 3A in the directions perpendicular to the longitudinal directions, and the insertion section 3C (far position insertion section) having the distal end of the needle 6 located a dimension of more than 10 mm apart from the distal end of the needle 6 of the observation insertion section 3A in the directions perpendicular to the longitudinal directions. The distal end of the needle 6 of the insertion section 3C (far position insertion portion) is located a dimension of 2 mm or more and 10 mm or less apart from the distal ends of the needles 6 of the insertion sections 3B and 3D (near position insertion sections) in the directions perpendicular to the longitudinal directions. Here, the insertion sections 3B and 3D serve as adjacent insertion sections adjacent to the standard insertion sections 3A in the circumferential directions of the body 2.

Figure 25:
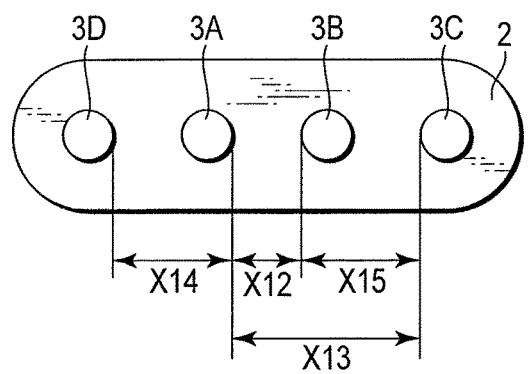
FIG. 25 is a schematic view showing a rigid endoscope according to a modification of the tenth embodiment from the distal direction.

Although the three insertion sections 3A to 3C are provided in the tenth embodiment, the present invention is not limited thereto. For example, as a modification, four insertion sections 3A to 3D may be arrayed in array directions which are specified directions perpendicular to the longitudinal directions as shown in FIG. 25. In the present modification, a dimension x12 of a space between the distal end of the needle 6 of the observation insertion section 3A and the distal end of the needle 6 of the irradiation insertion section 3B in the array directions is 2 mm or more to 10 mm or less. A dimension x13 of a space between the distal end of the needle 6 of the observation insertion section 3A and the distal end of the needle 6 of the air/water supply insertion section 3C in the array directions is more than 10 mm. A dimension x14 of a space between the distal end of the needle 6 of the observation insertion section 3A and the distal end of the needle 6 of the cleaning insertion section 3D in the array directions is 2 mm or more to 10 mm or less. A dimension x15 of a space between the distal end of the needle 6 of the irradiation insertion section 3B and the distal end of the needle 6 of the air/water supply insertion section 3C in the array directions is 2 mm or more to 10 mm or less. That is, the insertion sections 3A to 3D only consist of the single standard observation insertion section 3A (first insertion section), and a plurality of insertion sections 3B to 3D (second insertion sections). The insertion sections 3B to 3D (second insertion sections) only consist of the insertion sections 3B and 3D (near position insertion sections) each of which has the distal end of the needle 6 located a dimension of 2 mm or more and 10 mm or less apart from the distal end of the needle 6 of the observation insertion section 3A in the array directions, and the insertion section 3C (far position insertion section) having the distal end of the needle 6 located a dimension of more than 10 mm apart from the distal end of the needle 6 of the observation insertion section 3A in the array directions. The distal end of the needle 6 of the insertion section 3C (far position insertion section) is located a dimension of 2 mm or more and 10 mm or less apart from the distal end of the needle 6 of the insertion section 3B (near position insertion section) in the array directions. Here, the insertion sections 3B and 3D serve as adjacent insertion sections adjacent to the standard insertion section 3A in the array directions.

Figure 26:
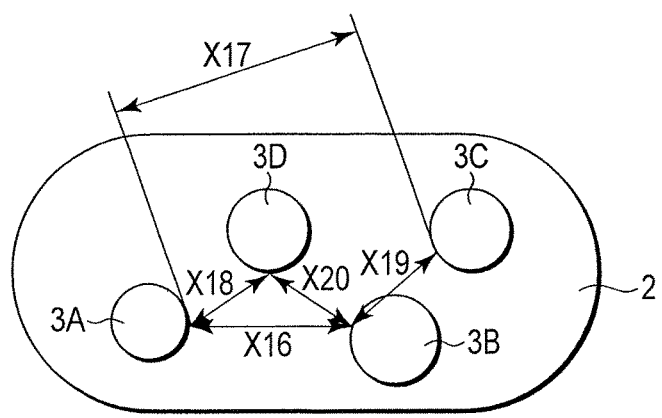
FIG. 26 is a schematic view showing the rigid endoscope according to the modifications of the ninth embodiment and the tenth embodiment from the distal direction.

Furthermore, as a modification, four insertion sections 3A to 3D may be arranged zigzag as shown in FIG. 26. In the present modification, a dimension x16 of a space between the distal end of the needle 6 of the observation insertion section 3A and the distal end of the needle 6 of the irradiation insertion section 3B in the directions perpendicular to the longitudinal directions is more than 10 mm. A dimension x17 of a space between the distal end of the needle 6 of the observation insertion section 3A and the distal end of the needle 6 of the air/water supply insertion section 3C in the directions perpendicular to the longitudinal directions is more than 10 mm. A dimension x18 of a space between the distal end of the needle 6 of the observation insertion section 3A and the distal end of the needle 6 of the cleaning insertion section 3D in the directions perpendicular to the longitudinal directions is 2 mm or more to 10 mm or less. A dimension x19 of a space between the distal end of the needle 6 of the irradiation insertion section 3B and the distal end of the needle 6 of the air/water supply insertion section 3C in the directions perpendicular to the longitudinal directions is 2 mm or more to 10 mm or less. A dimension x20 of a space between the distal end of the needle 6 of the irradiation insertion section 3B and the distal end of the needle 6 of the cleaning insertion section 3D in the directions perpendicular to the longitudinal directions is 2 mm or more to 10 mm or less. That is, the insertion sections 3A to 3D only consist of the single standard observation insertion section 3A (first insertion section), and a plurality of insertion sections 3B to 3D (second insertion sections). The insertion sections 3B to 3D (second insertion sections) only consist of the insertion section 3D (near position insertion section) having the distal end of the needle 6 located a dimension of 2 mm or more and 10 mm or less apart from the distal end of the needle 6 of the observation insertion section 3A in the directions perpendicular to the longitudinal directions, and the insertion sections 3B and 3C (far position insertion sections) each of which has the distal end of the needle 6 located a dimension of more than 10 mm apart from the distal end of the needle 6 of the observation insertion section 3A in the directions perpendicular to the longitudinal directions. The distal end of the needle 6 of the insertion section 3B (far position insertion section) is located a dimension of 2 mm or more and 10 mm or less apart from the distal end of the needle 6 of the insertion section 3D (near position insertion section) in the directions perpendicular to the longitudinal directions. The distal end of the needle 6 of the insertion section 3B (far position insertion section) is located a dimension of 2 mm or more and 10 mm or less apart from the distal end of the needle 6 of the insertion section 3C (far position insertion section) in the directions perpendicular to the longitudinal directions.

Eleventh Embodiment

Figure 27:
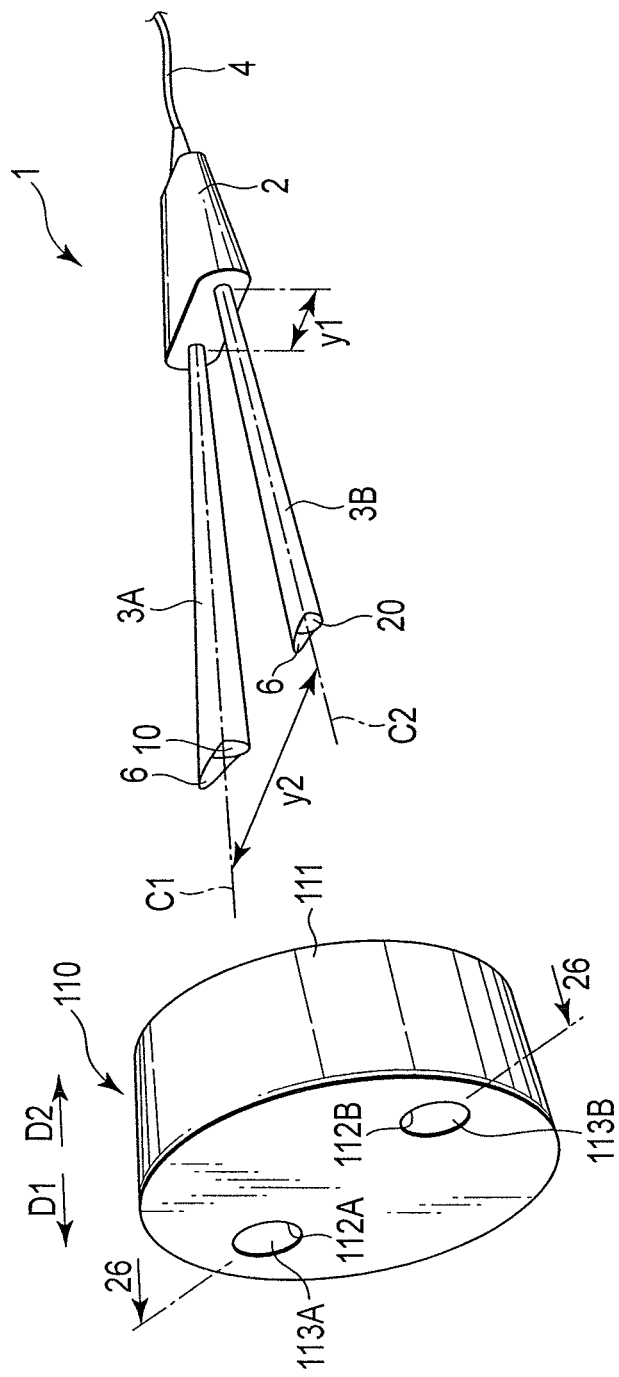
FIG. 27 is a perspective view schematically showing a rigid endoscope and a sticking assist instrument according to an eleventh embodiment of the present invention.

Now, an eleventh embodiment of the present invention will be described with reference to FIG. 27 and FIG. 28. FIG. 27 is a diagram showing a rigid endoscope 1 having substantially the configuration as that according to the first embodiment, and a sticking assist instrument 110 used to insert insertion sections 3A and 3B of the rigid endoscope 1 into a body cavity that is a void. As shown in FIG. 27, the rigid endoscope 1 includes a body 2, and a plurality of (two in the present embodiment) insertion sections 3A and 3B each extending from the body 2 toward the distal direction in the longitudinal directions as in the first embodiment. A needle 6 configured to be stuck into a body wall which is a wall part is provided at the distal end portion of each of the insertion sections 3A and 3B. The insertion section 3A is an observation insertion section 3A including an observation section 10, and the insertion section 3B is an irradiation insertion section 3B including an illumination section 20. In FIG. 27, the direction of an arrow D1 is an insertion direction toward which the insertion sections 3A and 3B are inserted, and the direction of an arrow D2 is a removal direction toward which the insertion sections 3A and 3B are removed.

Here, a distance between an axis C1 of the observation insertion section 3A and an axis C2 of the irradiation insertion section 3B at proximal ends of the insertion sections 3A and 3B is y1. A distance between the axis C1 of the observation insertion section 3A and the axis C2 of the irradiation insertion section 3B at distal ends of the insertion sections 3A and 3B is y2. As each of the insertion sections 3A and 3B extends from the body 2 toward the distal direction, each of the insertion sections 3A and 3B deflects. Therefore, from the proximal ends of the insertion sections 3A and 3B having zero deflecting amounts toward the distal direction, the distance between the axis C1 of the insertion section 3A and the axis C2 of the insertion section 3B increases, and the distance y2 becomes greater than the distance y1. Thus, the insertion sections 3A and 3B are not parallel to each other.

As shown in FIG. 27, the sticking assist instrument 110 includes an instrument body 111, and a plurality of (two in the present embodiment) inner peripheral surfaces 112A and 112B provided in the instrument body 111 along the insertion/removal directions of the insertion sections 3A and 3B. A space 113A through which the observation insertion section 3A passes is defined by the first inner peripheral surface 112A. A space 113B through which the irradiation insertion section 3B passes is defined by the second inner peripheral surface 112B. That is, each of the inner peripheral surfaces 112A and 112B defines the space through which corresponding one of the insertion sections 3A and 3B passes when the insertion sections 3A and 3B are inserted into the body cavity.

FIG. 28 is diagram showing the internal structure of the instrument body 111. As shown in FIG. 28, the first inner peripheral surface 112A has an axis E1, and the second inner peripheral surface 112B has an axis E2. The distance between the axis E1 of the first inner peripheral surface 112A and the axis E2 of the second inner peripheral surface 112B is z1, and the axis E1 and the axis E2 are parallel to each other. That is, the inner peripheral surfaces 112A and 112B are provided in a state that their axes E1 and E2 are parallel to each other. The distance z1 is the same as the distance y1 between the axis C1 of the observation insertion section 3A and the axis C2 of the irradiation insertion section 3B at the proximal ends of the insertion sections 3A and 3B. That is, the distance z1 between the axis E1 of the first inner peripheral surface 112A and the axis E2 of the second inner peripheral surface 112B is the same as the distance y1, at the proximal ends of the insertion sections 3A and 3B, between the axis C1 of the observation insertion section 3A which is an insertion section corresponding to the first inner peripheral surface 112A and the axis C2 of the irradiation insertion section 3B which is an insertion section corresponding to the second inner peripheral surface 112B.

The first inner peripheral surface 112A includes a first diametrical dimension portion 115 provided in a Part on an insertion direction side, a second diametrical dimension portion 117 provided in a part on a removal direction side, and a diametrical dimension changeable portion 119 provided between the first diametrical dimension portion 115 and the second diametrical dimension portion 117. The second diametrical dimension portion 117 is larger in diametrical dimension than the first diametrical dimension portion 115. The diametrical dimension changeable portion 119 decreases in diameter from the second diametrical dimension portion 117 toward the first diametrical dimension portion 115. Similarly to the first inner peripheral surface 112A, the second inner peripheral surface 112B is also provided with first diametrical dimension portion 115, a second diametrical dimension portion 117, and a diametrical dimension changeable portion 119.

The diametrical dimension of the first diametrical dimension portion 115 of the first inner peripheral surface 112A is formed to be substantially the same as the outside diameter of the observation insertion section 3A. The diametrical dimension of the first diametrical dimension portion 115 of the second inner peripheral surface 112B is formed to be substantially the same as the outside diameter of the irradiation insertion section 3B. That is, the diametrical dimension of the first diametrical dimension portion 115 of each of the inner peripheral surfaces 112A and 112B is formed substantially the same as the outside diameter of the insertion section corresponding to each of the inner peripheral surfaces 112A and 112B. However, the diametrical dimension of the first diametrical dimension portion 115 of each of the inner peripheral surfaces 112A and 112B is actually set to take dimensional errors and the dimensional errors of the distance y1 into consideration. Thus, the diametrical dimension first diametrical dimension portion 115 of the first inner peripheral surface 112A is set to be slightly larger than the outside diameter of the insertion section 3A, and the diametrical dimension of the first diametrical dimension portion 115 of the second inner peripheral surface 112E is set to be slightly larger than the outside diameter of the insertion section 3B. As a result, the insertion section 3A can pass through a part to an inner peripheral side of the first diametrical dimension portion 115 of the first inner peripheral surface 112A simultaneously with the passage of the insertion section 3B through a part to an inner peripheral side of the first diametrical dimension portion 115 of the second inner peripheral surface 112B.

Furthermore, the diametrical dimension of the second diametrical dimension portion 117 of each of the inner peripheral surfaces 112A and 112B is set to take into consideration the dimensional errors of the outside diameters of the insertion sections 3A and 3B, the dimensional errors of the distance y1, and the deflecting amounts of the insertion sections 3A and 3B. Therefore, even when the insertion sections 3A and 3B are deflected, it is possible to simultaneously insert the insertion section 3A into a part to the inner peripheral side of the second diametrical dimension portion 117 of the first inner peripheral surface 112A and insert the insertion section 3B into a part to the inner peripheral side of the second diametrical dimension portion 117 of the second inner peripheral surface 112B.

Now, the action of the sticking assist instrument 110 according to the present embodiment is described. As described above, the insertion sections 3A and 3B deflect, so that the distance between the axis C1 of the insertion section 3A and the axis C2 of the insertion section 3B increases toward the distal side. Therefore, when the needles 6 of the insertion sections 3A and 3B are stuck into the body wall without the use of the action of the sticking assist instrument 110, the insertion sections 3A and 3B that are not parallel to each other are stuck into the body wall. In this case, as the insertion sections 3A and 3B that are not parallel to each other are stuck into the body wall, the amount of sticking power is increased. Moreover, as the insertion sections 3A and 3B that are not parallel to each other are stuck into the body wall, the insertion sections 3A and 3B that are not parallel to each other are inserted into the body cavity. As a result, there may be a difference between the observation direction of the observation section 10 of the observation insertion section 3A and the illumination direction of the illumination section 20 of the irradiation insertion section 3B.

Accordingly, in the present embodiment, the sticking assist instrument 110 is used when the insertion sections 3A and 3B are inserted into the body cavity. The insertion section 3A is stuck into the body wall after passing through the space 113A defined by the first inner peripheral surface 112A, and the insertion section 3B is stuck into the body wall after passing through the space 113B defined by the second inner peripheral surface 112B.

When inserted in the space 113A, the insertion section 3A is guided toward a part to the inner peripheral side of the first diametrical dimension portion 115 through a part to the inner peripheral side of the second diametrical dimension portion 117 and a part to the inner peripheral side of the diametrical dimension changeable portion 119. When passing through the part to the inner peripheral side of the first diametrical dimension portion 115, the insertion section 3A bumps into the first diametrical dimension portion 115 of the first inner peripheral surface 112A. Similarly, when passing through a part to the inner peripheral side of the first diametrical dimension portion 115, the insertion section 3B bumps into the first diametrical dimension portion 115 of the second inner peripheral surface 112B. As described above, the diametrical dimension of the first diametrical dimension portion 115 of each of the inner peripheral surfaces 112A and 112B is formed to be substantially the same as the outside diameter of the insertion section corresponding to each of the inner peripheral surfaces 112A and 112B. The distance z1 between the axis E1 of the first inner peripheral surface 112A and the axis E2 of the second inner peripheral surface 112B is the same as the distance y1 between the axis C1 of the insertion section 3A and the axis C2 of the insertion section 3B at the proximal ends of the insertion sections 3A and 3B. Therefore, the insertion section 3A bumps into the first diametrical dimension portion 115 of the first inner peripheral surface 112A, and the insertion section 3B bumps into the first diametrical dimension portion 115 of the second inner peripheral surface 112B, so that the deflecting of the insertion sections 3A and 3B is prevented. Thus, the distance between the axis C1 of the insertion section 3A and the axis C2 of the insertion section 3B is y1 (z1) over the entire length of the insertion sections 3A and 3B in the longitudinal directions when the insertion section 3A passes through the part to the inner peripheral side of the first diametrical dimension portion 115 of the first inner peripheral surface 112A and at the same time, the insertion section 3B passes through the part to the inner peripheral side of the first diametrical dimension portion 115 of the second inner peripheral surface 112B. That is, the insertion sections 3A and 3B are parallel to each other. The insertion sections 3A and 3B that are parallel to each other are then stuck into the body wall, and inserted into the body cavity.

Accordingly, the sticking assist instrument 110 having the configuration described above provides the following advantageous effects. That is, in the sticking assist instrument 110 according to the present embodiment, the insertion section 3A of the rigid endoscope 1 bumps into the first diametrical dimension portion 115 when passing through the space 113A defined by the first inner peripheral surface 112A. Similarly, the insertion section 3B bumps into the first diametrical dimension portion 115 when passing through the space 113B defined by the second inner peripheral surface 112B. The diametrical dimension of the first diametrical dimension portion 115 of each of the inner peripheral surfaces 112A and 112B is formed to b substantially the same as the outside diameter of the insertion section corresponding to each of the inner peripheral surfaces 112A and 112B. The distance z1 between the axis E1 of the first inner peripheral surface 112A and the axis E2 of the second inner peripheral surface 112B is the same as the distance y1 between the axis C1 of the insertion section 3A and the axis C2 of the insertion section 3B at the proximal ends of the insertion sections 3A and 3B. Therefore, the insertion section 3A bumps into the first diametrical dimension portion 115 of the first inner peripheral surface 112A, and the insertion section 3B bumps into the first diametrical dimension portion 115 of the second inner peripheral surface 112B, so that the deflecting of the insertion sections 3A and 3B is Prevented. Thus, the distance between the axis C1 of the insertion section 3A and the axis C2 of the insertion section 3B is y1 (z1) over the entire length of the insertion sections 3A and 3B in the longitudinal directions when the insertion section 3A passes through the part to the inner peripheral side of the first diametrical dimension portion 115 of the first inner peripheral surface 112A and at the same time, the insertion section 3B passes through the part to the inner peripheral side of the first diametrical dimension portion 115 of the second inner peripheral surface 112B. That is, the insertion sections 3A and 3B are parallel to each other. The insertion sections 3A and 3B that are parallel to each other are stuck into the body wall, so that the amount of sticking power can be reduced. As the observation insertion section 3A including the observation section 10 and the irradiation insertion section 3B including the illumination section 20 that are parallel to each other are inserted into the body cavity, the difference between the observation direction of the observation section 10 and the illumination direction of the illumination section 20 can be prevented.

Modification of Eleventh Embodiment

Although the two inner peripheral surfaces 112A and 112B are provided in the eleventh embodiment, the present invention is not limited thereto. That is, plurality of inner peripheral surfaces (the inner peripheral surfaces 112A and 112B in the eleventh embodiment) have only to be provided in the instrument body so that their axes are parallel to each other along the insertion/removal directions of the insertion section. Then each of the inner peripheral surfaces has only to define the space through which corresponding one of the insertion sections passes when the insertion sections are inserted into the body cavity. Here, in the eleventh embodiment, the insertion section corresponding to the first inner peripheral surface 112A is the observation insertion section 3A, and the insertion section corresponding to the second inner peripheral surface 112B is the irradiation insertion section 3B.

Twelfth Embodiment

Now, a twelfth embodiment of the present invention will be described with reference to FIG. 29 and FIG. 30. In the twelfth embodiment, the configuration according to the eleventh embodiment is modified as follows. The same components as those in the eleventh embodiment are provided with the same reference signs and are not described.

FIG. 29 and FIG. 30 are diagrams showing a sticking assist instrument 110 according to the present embodiment. As shown in FIG. 29 and FIG. 30, the sticking assist instrument 110 includes instrument needles 121A and 121B protruding from an instrument body 111 toward the insertion direction. A first inner peripheral surface 112A is a coaxial inner peripheral surface which is formed coaxially with the first instrument needle 121A. The diametrical dimension of a first diametrical dimension portion 115 of the first inner peripheral surface 112A is formed to be the same as an inside diameter of the first instrument needle 121A. The inside of the first instrument needle 121A is in communication with a space 113A defined by the first inner peripheral surface 112A. Similarly, the second inner peripheral surface 112B is a coaxial inner peripheral surface which is formed coaxially with the second instrument needle 121B. The diametrical dimension of a first diametrical dimension portion 115 of the inner peripheral surface 112B is formed to be the same as the inside diameter of the second instrument needle 121B. The inside of the tool instrument 121B is in communication with a space 113B defined by the second inner peripheral surface 112B.

When insertion sections 3A and 3B are inserted into a body cavity, the instrument needles 121A and 121B are stuck into a body wall. While the instrument needles 121A and 121B are stuck in the body wall at sticking points, the insertion section 3A is inserted into the space 113A, and the insertion section 3B is inserted into the space 113B. The insertion section 3A is inserted into the body cavity from the sticking point of the first instrument needle 121A through the space 113A and inside of the first instrument needle 121A. Similarly, the insertion section 3B is inserted into the body cavity from the sticking point of the second tool needle 121B through the space 113B and inside of the second instrument needle 121B.

Accordingly, the sticking assist instrument 110 having the configuration described above provides the following advantageous effects in addition to the advantageous effects similar to those according to the eleventh embodiment. That is, in the sticking assist instrument 110, the instrument needles 121A and 121B protrude from the instrument body 111 toward the insertion direction. When the insertion sections 3A and 3B are inserted into a body cavity, the instrument needles 121A and 121B are stuck into a body wall. The insertion section 3A is then inserted into the body cavity from the sticking point of the first instrument needle 121A through the space 113A and inside the instrument needle 121A. Similarly, the insertion section 3B is inserted into the body cavity from the sticking point of the second instrument needle 121B through the space 113B and inside the second instrument needle 121B. Therefore, for example, in contrast with the case where the needles 6 are provided at the distal end portions of the insertion sections 3A to 3C of the rigid endoscope 1 in the first embodiment, it is not necessary to provide needles 6 at the distal end portions of the insertion sections 3A and 3B of the rigid endoscope 1. Accordingly, it is not necessary to provide the rigid endoscope 1 with a protection cover configured to protect functional sections (10, 20, 30, 40, and 80) from the needles 6. For example, it is possible to prevent damage to an image pickup unit 12 of an observation section 10 without providing the protection cover. This allows the insertion sections 3A and 3B of the rigid endoscope 1 to be simpler in configuration and to be reduced in size.

Modification of Twelfth Embodiment

Although the two instrument needles 121A and 121B are provided in the twelfth embodiment, the present invention is not limited thereto. That is, at least one instrument needle (the instrument needles 121A and 121B in the twelfth embodiment) has only to protrude from the instrument body 111 toward the insertion direction. In this case, the instrument needle is formed coaxially with one of the inner peripheral surfaces (the inner peripheral surfaces 112A and 112B in the twelfth embodiment).

Thirteenth Embodiment

Now thirteenth embodiment of the present invention will be described with reference to FIG. 31. In the thirteenth embodiment, the configuration according the twelfth embodiment is modified follows. The same components as those in the twelfth embodiment are provided with the same reference signs and are not described.

FIG. 31 is a diagram showing a sticking assist instrument 110 according to the present embodiment. As shown in FIG. 31, the sticking assist instrument 110 includes an instrument body 111, inner peripheral surfaces 112A and 112B, and instrument needles 121A and 121B, as in the twelfth embodiment. The protruding length of the first instrument needle 121A from the instrument body 111 is greater than that of the second instrument needle 121B.

An O-ring 123 is provided in a first diametrical dimension portion 115 of the first inner peripheral surface 112A coaxial with the tool needle 121A. An airtight lid 125 is provided in a second diametrical dimension portion 117 of the inner peripheral surface 112A. The airtight lid 125 is urged in a direction of an arrow F in FIG. 31. The instrument body 111 is provided with protrusions 126. Each airtight lid 125 bumps into the protrusion 126, and the movement of each airtight lid 125 beyond the protrusion 126 in the direction of the arrow F is thereby regulated. As a result, when no force is applied to the airtight lid 125 from the removal direction, an insertion hole 127 into a space 113A is shut by the airtight lid 125. Similarly to the first inner peripheral surface 112A, the second inner peripheral surface 112B coaxial with the second instrument needle 121B is provided with an O-ring 123 and an airtight lid 125.

When insertion sections 3A and 3B are inserted into a body cavity, the instrument needles 121A and 121B are stuck into a body wall. In this case, the first instrument needle 121A having a greater protruding length from the instrument body 111 is first stuck into the body wall, and then the second instrument needle 121B having a smaller protruding length from the instrument body 111 is stuck into the body wall. When the insertion sections 3A and 3B are not inserted in the body cavity, no force is applied to the airtight lid 125 from the removal direction. Thus, the insertion hole 127 into each of the spaces 113A and 113B is shut by the airtight lid 125. This prevents the outflow of air from the spaces 113A and 113B to an outside. That is, when the insertion sections 3A and 3B are not inserted in the body cavity, the airtight lid 125 serves as a first outflow prevention portion which is configured to prevent the outflow of air from the space 113A defined by the first inner peripheral surface 112A and the space 113B defined by the second inner peripheral surface 112B to the outside.

While the instrument needles 121A and 121B are being stuck in the body wall at sticking points, the insertion section 3A is inserted into the space 113A from the insertion hole 127, and the insertion section 3B is inserted into the space 113B from the insertion hole 127. At the same time, the airtight lids 125 of the respective inner peripheral surfaces 112A and 112B are pressed by the insertion sections 3A and 3B from the removal direction. Thus, each airtight lid 125 moves to a position indicated by a dotted line in FIG. 31 in a direction opposite to the arrow F against the urging force.

The insertion section 3A is then inserted into the body cavity from the sticking point of the instrument needle 121A through the space 113A and inside of the instrument needle 121A. When the insertion section 3A passes through a part to the inner peripheral side of the first diametrical dimension portion 115, the O-ring 123 is jammed between the outer peripheral surface of the insertion section 3A and the first diametrical dimension portion 115. As a result, the part between the insertion section 3A and the first diametrical dimension portion 115 is airtight, and the outflow of air from the space 113A toward the removal direction is prevented. Similarly, the O-ring 123 of the second inner peripheral surface 112B is jammed, so that the part between the insertion section 3B and the first diametrical dimension portion 115 is airtight. This prevents the outflow of air from the space 113B toward the removal direction. That is, when the insertion sections 3A and 3B are inserted in the body cavity, the O-ring 123 serves as a second outflow prevention portion which is configured to prevent the outflow of air from the space 113A defined by the first inner peripheral surface 112A and the space 113B defined by the second inner peripheral surface 112B to the outside.

Accordingly, the sticking assist instrument 110 having the configuration described above provides the following advantageous effects in addition to the advantageous effects similar to those according to the twelfth embodiment. That is, in the sticking assist instrument 110, the protruding length of the first instrument needle 121A from the instrument body 111 is greater than the protruding length of the second instrument needle 121B. Therefore, when the instrument needles 121A and 121B are stuck into the body wall, the first instrument needle 121A having a greater protruding length from the instrument body 111 is first stuck into the body wall, and then the second instrument needle 121B having a smaller protruding length from the instrument body 111 is stuck into the body wall. Thus, as compared with the case where the two instrument needles 121A and 121B are simultaneously stuck into the body wall, the amount of sticking power can be reduced.

Furthermore, in the sticking assist instrument 110, the outflow of air from the spaces 113A and 113B to the outside is prevented by the airtight lids 125 when the insertion sections 3A and 3B are not inserted in the body cavity. When the insertion sections 3A and 3B are inserted in the body cavity, the outflow of air from the spaces 113A and 113B to the outside is prevented by the O-rings 123. Consequently, pneumoperitoneum pressure can be maintained both when the insertion sections 3A and 3B are not inserted in the body cavity and when the insertion sections 3A and 3B are inserted in the body cavity.

Modification of Thirteenth Embodiment

Although the two instrument needles 121A and 121B are provided, the present invention is not limited thereto. That is, it is only necessary to provide a plurality of needles including a first instrument needle (the instrument needle 121A in the thirteenth embodiment), and a second instrument needle (the instrument needle 121B in the thirteenth embodiment) different from the first instrument needle in the protruding length from the instrument body 111.

In the thirteenth embodiment, the outflow of air from the spaces 113A and 113B to the outside is prevented by the airtight lids 125 the insertion sections 3A and 3B are not inserted in the body cavity. When the insertion sections 3A and 3B are inserted in the body cavity, the outflow of air from the spaces 113A and 113B to the outside is prevented by the O-rings 123. However, the configuration to prevent the outflow of air from the spaces 113A and 113B is not limited to the above-mentioned configuration. For example, an airtight lid similar to the airtight lid 125 according to the thirteenth embodiment may be provided inside of each of the instrument needles 121A and 121B. That is, the first outflow prevention portion (the airtight lid 125 in the thirteenth embodiment) which is configured to prevent the outflow of air from the space (the spaces 113A and 113B in the thirteenth embodiment) defined by the inner peripheral surface (the inner peripheral surfaces 112A and 112B in the thirteenth embodiment) when the insertion section (the insertion sections 3A and 3B in the thirteenth embodiment) is not inserted in the body cavity has only to be provided in the inner peripheral surface or inside of the instrument needle (the instrument needles 121A and 121B in the thirteenth embodiment). Similarly, the second outflow prevention portion (the O-ring 123 in the thirteenth embodiment) which is configured to prevent the outflow of air from the space defined by the inner peripheral surface when the insertion section is inserted in the body cavity has only to be provided in the inner peripheral surface or inside of the instrument needle.

Fourteenth Embodiment

Now, a fourteenth embodiment of the present invention will be described with reference to FIG. 32. In the fourteenth embodiment, the configuration according to the twelfth embodiment is modified as follows. The same components as those in the twelfth embodiment are provided with the same reference signs and are not described.

FIG. 32 is a diagram showing a sticking assist instrument 110 according to the present embodiment. As shown in FIG. 32, an instrument body 111 of the sticking instrument tool 110 includes a fixing portion 131 fixed to a body surface (the surface of a wall part) during use, a first movable portion 133A in which an instrument needle 121A extends toward the insertion direction from an end on the insertion direction side, and a second movable portion 133B in which an instrument needle 121B extends toward the insertion direction from an end on the insertion direction side. Bore-like portions 132A and 132B are formed in the fixing portion 131 along the insertion/removal directions of insertion sections 3A and 3B of a rigid endoscope 1. The first movable portion 133A is movable in the bore-like portion 132A relative to the fixing portion 131 in the insertion/removal directions of the insertion sections 3A and 3B. The first movable portion 133A moves integrally with the instrument needle 121A. The second movable portion 133B is movable in the bore-like portion 132B relative to the fixing portion 131 in the insertion/removal directions of the insertion sections 3A and 3B. The second movable portion 133B moves integrally with the instrument needle 121B.

A first inner peripheral surface 112A coaxial with the instrument needle 121A is provided in the first movable portion 133A along the insertion/removal directions of the insertion sections 3A and 3B. Similarly, a second inner peripheral surface 112B coaxial with the instrument needle 121B is provided in the second movable portion 133B along the insertion/removal directions of the insertion sections 3A and 3B.

The first movable portion 133A includes a first cylindrical portion 135 having the same outside diameter as the instrument needle 121A, and a second cylindrical portion 136 which is provided to the removal direction side of the first cylindrical portion 135 and which is greater in outside diameter than the first cylindrical portion 135. A second diametrical dimension portion 117 and a diametrical dimension changeable portion 119 of the first inner peripheral surface 112A are formed inside of the second cylindrical portion 136. A first diametrical dimension portion 115 of the first inner peripheral surface 112A is formed inside of the first cylindrical portion 135.

In the second cylindrical portion 136 of the first movable portion 133A, a press portion 138 is provided at an end on the removal direction side. When the press portion 138 is pressed to the insertion direction, the movable portion 133A and the instrument needle 121A move relative to the fixing portion 131. In the movable portion 133A, a step 139 is formed between the first cylindrical portion 135 and the second cylindrical portion 136. The step 139 bumps into an end face on the removal direction side of the fixing portion 131, and the movement of the first movable portion 133A in the insertion direction is thereby regulated.

A cam groove 141 is spirally provided in the outer peripheral surface of the movable portion 133A. A cam pin 142 which engages with the cam groove 141 of the movable portion 133A is provided in the bore-like portion 132A of the fixing portion 131. The cam groove 141 and the cam pin 142 are provided so that the movable portion 133A moves in the insertion/removal directions of the insertion sections 3A and 3B to rotate around an axis E1 of the inner peripheral surface 112A. That is, the cam groove 141 and the cam pin 142 serve as a rotary unit which is configured to move the movable portion 133A in the insertion/removal directions of the insertion sections 3A and 3B so that the movable portion 133A rotates around the axis E1 of the first inner peripheral surface 112A. As a result, when the instrument needle 121A is stuck into a body wall, the instrument needle 121A is stuck into the body wall so that the instrument needle 121A rotates integrally with the movable portion 133A around the axis E1 of the first inner peripheral surface 112A. The second movable portion 133B has the same configuration as the first movable portion 133A, and is therefore provided with reference signs and is not described.

Accordingly, the sticking assist instrument 110 having the configuration described above provides the following advantageous effects in addition to the advantageous effects similar to those according to the twelfth embodiment. That is, in the sticking assist instrument 110, the instrument body 111 includes the fixing portion 131, and movable portions 133A and 133B movable relative to the fixing portion 131 in the insertion/removal directions of the insertion sections 3A and 3B. The first movable portion 133A is movable integrally with the instrument needle 121A relative to the fixing portion 131 in the insertion/removal directions of the insertion sections 3A and 3B. Similarly, the second movable portion 133B is movable integrally with the instrument needle 121B relative to the fixing portion 131 in the insertion/removal directions of the insertion sections 3A and 3B. Thus, the instrument needles 121A and 121B can be stuck into the body wall not simultaneously but sequentially. Consequently, as compared with the case where both of the instrument needles 121A and 121B are simultaneously stuck into the body wall, the amount of sticking power can be reduced.

Furthermore, in the sticking assist instrument 110, the cam groove 141 is provided in each of the movable portions 133A and 133B. The bore-like portion 132A is provided with the cam pin 142 which engages with the cam groove 141 of the movable portion 133A. The bore-like portion 132B is provided with the cam pin 142 which engages with the cam groove 141 of the movable portion 133B. The cam groove 141 and the cam pin 142 are provided so that the movable portion 133A moves in the insertion/removal directions of the insertion sections 3A and 3B to rotate around an axis E1 of the first inner peripheral surface 112A. As a result, when the instrument needles 121A and 121B are stuck into a body wall, the instrument needle 121A is stuck into the body wall so that the instrument needle 121A rotates integrally with the movable portion 133A around the axis E1 of the first inner peripheral surface 112A. Similarly, the movable portion 133B moves in the insertion/removal directions of the insertion sections 3A and 3B to rotate around an axis E2 of the first inner peripheral surface 112A. As a result, when the instrument needles 121A and 121B are stuck into a body wall, the instrument needle 121B is stuck into the body wall so that the instrument needle 121B rotates integrally with the movable portion 133B around the axis E2 of the first inner peripheral surface 112B. Consequently, the amount of sticking power to stick the instrument needles 121A and 121B into the body wall can be reduced.

Modification of Fourteenth Embodiment

Although the two movable portions 133A and 133B are provided in the fourteenth embodiment, the present invention is not limited thereto. That is, the instrument body 111 has only to be provided with at least one movable portion (the movable portions 133A and 133B in the fourteenth embodiment) in which the instrument needle (the instrument needles 121A and 121B in the fourteenth embodiment) extends toward the insertion direction from the end on the insertion direction side, and which is movable integrally with the instrument needle relative to the fixing portion 131 in the insertion/removal directions of the insertion section (the insertion sections 3A and 3B in the fourteenth embodiment). Further, the inner peripheral surface (the inner peripheral surfaces 112A and 112B in the fourteenth embodiment) coaxial with the instrument needle has only to be provided in the movable portion along the insertion/removal directions of the insertion section.

In the thirteenth embodiment, the cam grooves 141 and the cam pins 142 are used to rotate the first movable portion 133A around the axis E1 of the first inner peripheral surface 112A and to rotate the movable portion 133B around the axis E2 of the first inner peripheral surface 112B. However, the present invention is not limited thereto. That is, it is only necessary to provide a rotary unit which is configured to move the movable portion (the movable portions 133A and 133B in the fourteenth embodiment) in the insertion/removal directions of the insertion section so that the movable portion rotates around the axis of the inner peripheral surface (112A and 112B in the fourteenth embodiment) coaxial with the instrument needle (the tool needles 121A and 121B in the fourteenth embodiment).

Fifteenth Embodiment

Now, a fifteenth embodiment of the present invention will be described with reference to FIG. 33 to FIG. 39.

FIG. 33 to FIG. 36 are diagrams showing the configuration of an exclusion forceps 150 according to the present embodiment. As shown in FIG. 33 and FIG. 34, the exclusion forceps 150 is brought into contact with an organ 151 which is a living tissue so that the organ 151 is contracted by pressure. Such a treatment is referred to as exclusion. For example, in surgery that uses a rigid endoscope (not shown), the field of view of the rigid endoscope is secured by the exclusion of the organ 151.

As shown in FIG. 33 to FIG. 36, the exclusion forceps 150 includes a plurality of insertion sections 152A to 152D extending in the longitudinal directions. Each of the insertion sections 152A to 152D has desired rigidity. Each of the insertion sections 152A to 152D is made of, for example, stainless steel or plastic, and has a diameter of 2 mm or less.

An exclusion section 153 configured to exclude the organ 151 is provided at a distal end portion of each of the insertion sections 152A to 152D. A holder 155 is provided to a proximal direction side of the insertion sections 152A to 152D. Proximal ends of the insertion sections 152A to 152D are removably attached to the holder 155. The insertion sections 152A to 152D are thereby held to the holder 155. A grip 156 configured to be gripped by a surgeon is fixed to the proximal direction side of the holder 155.

FIG. 37 and FIG. 38 are diagrams showing an attach/remove configuration between the insertion section 152A and the holder 155. Although the configuration to attach/remove the insertion section 152A to/from the holder 155 is only described below, the insertion sections 152B to 152D are attached to or removed from the holder 155 in the same manner as the insertion section 152A. As shown in FIG. 34, FIG. 37, and FIG. 38, the holder 155 is provided with a through-bore 158 into which the proximal end portion of the insertion section 152A is inserted. The number of the through-bores 158 provided is the same as the number of the insertion sections 152A to 152D or is more than the insertion sections 152A to 152D. A corresponding one of the insertion sections 152A to 152D is removably inserted into each of the through-bores 158. Here, an axis G1 of the through-bore 158 is parallel to the longitudinal directions.

The holder 155 is provided with the same number of communication bores 159 as the through-bores 158. Each of the communication bores 159 allows the corresponding through-bore 158 to be in communication with the outside of the holder 155. An axis G2 of the communication bore 159 intersects at right angles with the axis G1 of the through-bore 158.

A positioning unit 161 which is configured to position the insertion section 152A in the longitudinal directions is provided in an attach/remove portion between the holder 155 and the insertion section 152A. The positioning unit 161 includes a spherical ball 162, and a spring member 163 which is an urging member having one end connected to the ball 162. The other end of the spring member 163 is connected to the holder 155. The ball 162 is urged by the spring member 163 toward the through-bore 158 along the axis G2 of the communication bore 159. A depression 165 is provided in an outer peripheral portion of the proximal end portion of the insertion section 152A. When the proximal end portion of the insertion section 152A is inserted in the through-bore 158, the ball 162 is urged by the spring member 163 and thereby locked to the depression 165. As a result, the insertion section 152A is attached to the holder 155, and the insertion section 152A is held by the holder 155. Similarly, the insertion sections 152B to 152D are held by the holder 155.

FIG. 39 is a diagram showing the configuration of the distal end portion of the insertion section 152A. As shown in FIG. 37 to FIG. 39, a needle 167 is provided in an outer peripheral portion of the distal end portion of the insertion section 152A. When an insertion section 152A is inserted into a body cavity that is a void, the needle 167 is stuck into a body wall which is a wall part. In the insertion section 152A, the needle 167 is located in a part on the side of a first perpendicular direction (the direction of an arrow I1 in FIG. 39) perpendicular to the longitudinal directions.

The exclusion section 153 of the insertion section 152A is provided with a mounting surface 169 on which the organ (living tissue) 151, which is targeted in exclusion, is mounted. The mounting surface 169 extends in the outer peripheral portion of the insertion section 152A from the distal end portion of the insertion section 152A toward the proximal direction. The mounting surface 169 is located an opposite side of the needle 167 across an axis H of the insertion section 152A. That is, in the insertion section 152A, the mounting surface 169 is located in a part on the side of a second perpendicular direction (the direction of an arrow I2 in FIG. 39) opposite to the first perpendicular direction. In the configuration described above, the needle 167 and the mounting surface 169 are not continuous in the outer peripheral portion of the insertion section 152A in directions around the axis H of the insertion section 152A. That is, the needle 167 and the mounting surface 169 are provided apart from each other in the directions around the axis H of the insertion section 152A.

The mounting surface 169 includes an uneven portion 171 having an uneven surface. The uneven portion 171 is configured to prevent the organ (exclusion target) 151 mounted on the mounting surface 169 from sliding over the mounting surface 169. The uneven portion 171 is located the opposite side of the needle 167 across the axis H of the insertion section 152A.

When the insertion section 152A moves in the body cavity, the insertion section 152A may contact a living tissue other than the organ 151 targeted in exclusion. In this case, the uneven portion 171 is provided to decrease the area of contact between the insertion section 152A and the living tissue other than the organ 151. This suppresses the friction between the insertion section 152A and the living tissue other than the organ 151. In the same manner as the insertion section 152A, each of the insertion sections 152B to 152D is provided with a needle 167, a mounting surface 169, and an uneven portion 171.

As shown in FIG. 37 to FIG. 39, a substantially J-shaped curved portion 173 is provided at the distal end portion of the insertion section 152A. In the curved portion 173, the insertion section 152A is curved from the first perpendicular direction (the direction of the arrow I1 in FIG. 39) in which the needle 167 is located to the second perpendicular direction (the direction of the arrow I2 in FIG. 39) in which the mounting surface 169 is located. Parts of the mounting surface 169 and the uneven portion 171 located in the curved portion 173 are inclined relative to the longitudinal directions.

Now, the action of the exclusion forceps 150 according to the present embodiment is described. As shown in FIG. 33, FIG. 38, and FIG. 39, when the insertion sections 152A to 152D are attached to the holder 155, the proximal end portion of each of the insertion portions 152A to 152D is inserted into the corresponding through-bore 158. The ball 162 urged by the spring member 163 is locked by the depression 165 of each of the insertion sections 152A to 152D. As a result, the insertion sections 152A to 152D are attached to the holder 155, and the insertion sections 152A to 152D are held by the holder 155.

Regarding the number of the insertion sections 152A to 152D held by the holder 155 and whether to attach the insertion sections 152A to 152D to the respective through-bores 158 (the space between the insertion sections 152A to 152D), desired conditions are selected to suit to, for example, the size of the organ 151 to be excluded. The number of insertion sections 152A to 152D held by the holder 155 is more than one.

The needle 167 is stuck into the body wall while the grip 156 is being gripped, and the distal end portion of each of the insertion sections 152A to 152D is inserted into the body cavity. In this case, the needle 167 is located at the distal end portion of each of the insertion sections 152A to 152D, and each needle 167 can therefore be stuck into the body wall with a small amount of operation force.

After the distal end portion of each of the insertion sections 152A to 152D is inserted in the body cavity, the insertion sections 152A to 152D are located so that the organ 151 targeted in exclusion and the mounting surfaces 169 face each other. That is, the insertion sections 152A to 152D are located to the first perpendicular direction side of the organ 151. The organ 151 is then mounted on the mounting surface 169 of each of the insertion sections 152A to 152D. In each of the insertion sections 152A to 152D, the mounting surface 169 is located on the opposite side of the needle 167 across the axis H of each of the insertion sections 152A to 152D. Thus, when the organ 151 is mounted on the mounting surface 169, it is possible to effectively prevent the organ 151 from being damaged by the needle 167. The uneven portion 171 of the mounting surface 169 also prevents the organ 151 from sliding over the mounting surface 169. The organ 151 is contracted by the pressure from the mounting surfaces of the insertion sections 152A to 152D, and is excluded.

Meanwhile, Jpn. Pat. Appln. KOKAI Publication No. 6-154152, Jpn. Pat. Appln. KOKAI Publication 2000-116663, and Jpn. Pat. Appln. KOKAI Publication No. 2005-279010 disclose exclusion forcipes (retractors) which is used in abdominal operation under endoscopic observation. The exclusion forceps according to Jpn. Pat. Appln. KOKAI Publication No. 2000-116663 only applies force to a desired part of a heart and thereby suppresses the heartbeat. This reduces the burden on the heart and decreases the degree of invasion of a patient. The exclusion forceps according to Jpn. Pat. Appln. KOKAI Publication No. 2005-279010 is provided with an exclusion section having a secured dimension in directions (width directions) perpendicular to the longitudinal directions. Thus, even a soft living tissue such as the intestines requiring a large exclusion area is properly excluded.

However, the exclusion forcipes according to Jpn. Pat. Appln. KOKAI Publication No. 6-154152, Jpn. Pat. Appln. KOKAI Publication No 2000-116663, and Jpn. Pat. Appln. KOKAI Publication No. 2005-279010 have complex configurations. The rigidity of the exclusion forcipes may not be sufficiently secured during exclusion depending on the kind of an organ targeted in exclusion. In this case, the exclusion of the organ is difficult.

Accordingly, in the exclusion forceps 150 according to the present embodiment, a plurality of insertion sections 152A to 152D are held by the holder 155. Therefore, rigidity is higher during the exclusion of the organ 151, which is targeted in exclusion, than in the case of a single insertion section (152A). As the rigidity during exclusion is easily secured (with a simple configuration), the exclusion of the organ 151 is facilitated.

The insertion sections 152A to 152D are then taken out of the body cavity. Each of the insertion sections 152A to 152D is removed from the corresponding through-bore 158 so that the ball 162 is unlocked from the depression 165. As a result, each of the insertion sections 152A to 152D is detached from the corresponding through-bore 158. The insertion sections 152A to 152D are then cleaned.

Accordingly, the exclusion forceps 150 having the configuration described above provides the following advantageous effects. That is, in the exclusion forceps 150 according to the present embodiment, each of the insertion sections 152A to 152D has desired rigidity. A plurality of insertion sections 152A to 152D are held by the holder 155. Therefore, the rigidity is higher during the exclusion of the organ 151, targeted in exclusion, than in the case of a single insertion section (152A). As the rigidity during exclusion is easily secured, the exclusion of the organ 151 is facilitated.

In the exclusion forceps 150, each of the insertion sections 152A to 152D is removable from holder 155 (the corresponding through-bore 158). Therefore, the number of the insertion sections 152A to 152D can be selected to suit to, for example, the size of the organ 151, and each of the insertion sections 152A to 152D can be disposed at a proper position. Consequently, the organ 151 can be properly excluded to suit to, for example, the size of the organ 151.

In each of the insertion sections 152A to 152D of the exclusion forceps 150, the mounting surface 169 is located on the opposite side of the needle 167 across the axis H of each of the insertion sections 152A to 152D. Thus, when the organ 151 is mounted on the mounting surface 169, it is possible to effectively prevent the organ 151 from being damaged by the needle 167. The needle 167 of each of the insertion sections 152A to 152D can therefore be stuck into a body wall (wall part) with a small amount of operation force, and operation time can be reduced.

In the exclusion forceps 150, the uneven portion 171 of the mounting surface 169 configured to prevent the organ 151 from sliding over the mounting surface 169. This facilitates the exclusion of the organ 151.

The number of the insertion sections 152A to 152D, the number of the through-bores 158, the number of the communication bores 159, the space between the through-bores 158, the space between the insertion sections 152A to 152D, the longitudinal dimension of the mounting surface 169, and the dimension of the uneven portion 171 in the longitudinal directions are not particularly limited to the configuration according to the present embodiment.

Sixteenth Embodiment

Now, a sixteenth embodiment of the present invention will be described with reference to FIG. 40 to FIG. 43. In the sixteenth embodiment, the configuration according to the fifteenth embodiment is modified as follows. The same components as those in the fifteenth embodiment are provided with the same reference signs and are not described.

FIG. 40 is a diagram showing the configuration of an exclusion forceps 150 according to the present embodiment. As shown in FIG. 40, the exclusion forceps 150 includes a parallel link unit 175 which rotatably attaches insertion sections 152A and 152D to a holder 155. FIG. 41 and FIG. 42 are diagrams showing a configuration to attach/remove the insertion section 152A to/from and the holder 155. Although the configuration to attach/remove the insertion section 152A to/from and the holder 155 is only described below, the insertion section 152D is attached to and removed from the holder 155 in the same manner as the insertion portion 152A.

As shown in FIG. 41 and FIG. 42, the parallel link unit 175 includes a rotary member 177 provided rotatably relative to the holder 155. The insertion section 152A is attached to the rotary member 177. In the present embodiment, the rotary member 177 is provided with a through-bore 158. The rotary member 177 is also provided with a communication bore 159 which allows the through-bore 158 to be in communication with an outside of the rotary member 177. The proximal end portion of the insertion section 152A is inserted into the through-bore 158 so that the insertion section 152A is attached to the rotary member 177 by a positioning unit 161. As a result, the insertion section 152A is held by the holder 155.

The same number of the rotary members 177 as the insertion sections 152A and 152D are provided. That is, a plurality of rotary members 177 are provided. The proximal end portion of a corresponding one of the insertion sections 152A and 152D is attached to each rotary member 177. Each rotary member 177 rotates relative to the holder 155 integrally with the corresponding one of the insertion sections 152A and 152D. As a result, a plurality of insertion sections 152A and 152D are held by the holder 155.

The holder 155 is also provided with a convex portion 178 projecting toward the rotary member 177. The rotary member 177 is provided with a recess 179 in which the convex portion 178 is inserted. When the convex portion 178 is inserted in the recess 179, the rotary member 177 is rotatable relative to the holder 155 around a rotation axis K. The rotation axis K of the rotary member 177 passes through the convex portion 178 and the recess 179. The rotary member 177 rotates relative to the holder 155 in response to the rotation of the recess 179 relative to the convex portion 178. In this case, rotation directions of the rotary member 177 correspond to left-and-right directions of FIG. 40, and correspond to directions perpendicular to the plane of FIG. 42. Consequently, the corresponding one of the insertion sections 152A and 152D rotates integrally with each of the rotary members 177, and the insertion sections 152A and 152D are inclined relative to the longitudinal directions (a state indicated by dotted lines in FIG. 40).

In the present embodiment, the convex portion 178 is provided in the holder 155, and the recess 179 is provided in the rotary member 177. However, the present invention is not limited thereto. For example, a recess may be provided in the holder 155, and a convex portion configured to be inserted into the recess may be provided in the rotary member 177.

The parallel link unit 175 also includes a link 181 which is a link member to link the rotary members 177. The rotary members 177 are linked by the link 181 so that a plurality of rotary members 177 rotate in the same direction. FIG. 43 is a diagram showing the configuration of a grip 156. As shown in FIG. 40 and FIG. 43, the grip 156 is provided with a through-bore 183. The link 181 passes through the through-bore 183 of the grip 156, and links the rotary members 177.

Now, the action of the exclusion forceps 150 according to the present embodiment is described. As shown in FIG. 41 and FIG. 42, the convex portion 178 of the holder 155 is attached to the recess 179 of the rotary member 177, and the rotary member 177 is thereby attached to the holder 155. The rotary members 177 are linked by the link 181.

Each of the insertion sections 152A to 152D is attached to the corresponding rotary member 177 by the positioning unit 161 as in the first embodiment. As a result, the insertion sections 152A to 152D are held by the holder 155. As in the first embodiment, regarding the number of the insertion sections 152A and 152D attached to the rotary members 177 and whether to attach the insertion sections 152A and 152D to the respective through-bores 158 (the space between the insertion sections 152A and 152D), desired conditions are selected to suit to, for example, the size of the organ 151 to be excluded. The number of insertion sections 152A and 152D held by the holder 155 is more than one.

When the insertion sections 152A and 152D are inserted in a body cavity, the needles 167 are stuck into a body wall as indicated by solid lines in FIG. 40. As a result, the distal end portions of the insertion sections 152A and 152D are inserted in the body cavity. The organ 151 is then mounted on the mounting surface 169. Further, the organ 151 is excluded.

According to the present embodiment, the insertion sections 152A and 152D can be inclined relative to the longitudinal directions by the parallel link unit 175 after the needle 167 is stuck into the body wall. Accordingly, as indicated by dotted lines in FIG. 40, each rotary member 177 rotates relative to the holder 155 around the rotation axis K. In this case, the holder 155 and the grip 156 slide in directions (left-and-right directions of FIG. 40) perpendicular to the longitudinal directions.

As described above, in the exclusion forceps 150 according to the present embodiment, the parallel link unit 175 enables the holder 155 and the grip 156 to slide in the directions perpendicular to the longitudinal directions after the needle 167 is stuck into the body wall. This permits the mounting position of the organ 151 in the mounting surface 169 to be adjusted even after the needle 167 is stuck into the body wall. Consequently, the operability of the exclusion forceps 150 can be improved.

Seventeenth Embodiment

Now, a seventeenth embodiment of the present invention will be described with reference to FIG. 44 to FIG. 48. In the seventeenth embodiment, the configuration according to the fifteenth embodiment is modified as follows. The same components as those in the fifteenth embodiment are provided with the same reference signs and are not described. In FIG. 44 to FIG. 48, some components are not shown for simplicity.

Figure 44:
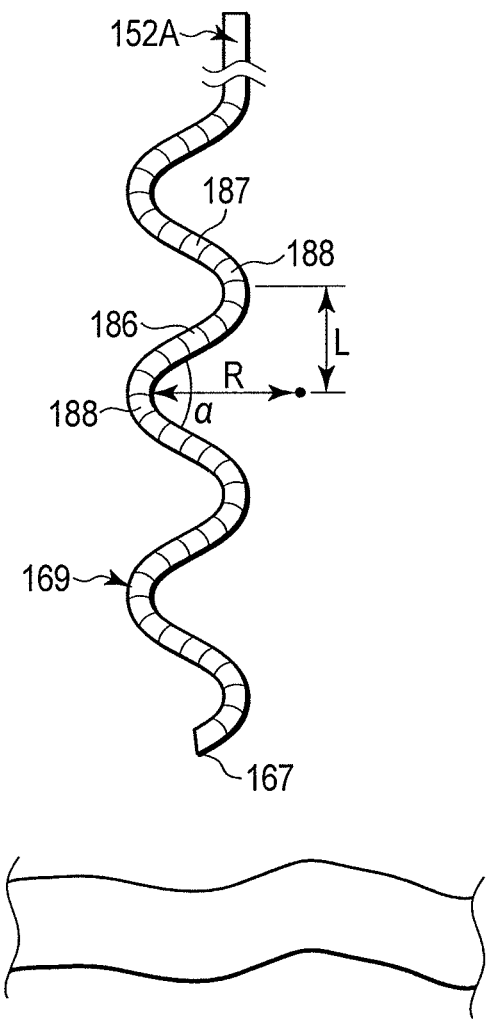
FIG. 44 is a schematic view showing a state before one insertion section of an exclusion forceps according to a seventeenth embodiment of the present invention is inserted into a body cavity.

FIG. 44 to FIG. 46 are diagrams showing the configuration of one insertion section 152A. As shown in FIG. 44 to FIG. 46, a zigzag portion 185 is provided at the distal end portion of the insertion section 152A including a needle 167 and a mounting surface 169. As shown in FIG. 45, the zigzag portion 185 is stuck into a body wall. As shown in FIG. 46, the zigzag portion 185 is then inserted into a body cavity, and excludes an organ 151. Therefore, the zigzag portion 185 includes the needle 167 and the mounting surface 169.

The zigzag portion 185 includes a plurality of first extensions 186 extending in such a manner as to be inclined relative to the longitudinal directions, and a plurality of second extensions 187 extending in such a manner as to be inclined relative to the longitudinal directions toward a direction opposite to the first extensions 186. The first extensions 186 and the second extensions 187 are alternately arranged in the longitudinal directions. A top 188 is provided between the first extension 186 and the second extension 187. In the zigzag portion 185, the distance L between the tops 188 in the longitudinal directions is, for example, 50 mm or less. The angle α between the first extension 186 and the second extension 187 at the top 188 is, for example, 90° or more. The inside radius R at the top 188 is, for example, 30 mm or less.

Now, the action of the exclusion forceps 150 according to the present embodiment is described. When one insertion section 152A is inserted into a body cavity, the needle 167 of the insertion section 152A is inserted into a body wall as shown in FIG. 45. The zigzag portion 185 is then inserted into the body cavity so that the first extensions 186 and the second extensions 187 are alternately inclined relative to the body wall (laid on the body wall). The zigzag portion 185 is then inserted into the body cavity as shown in FIG. 46. In this case, the part to the proximal direction side of the zigzag portion 185 in the insertion section 152A is perpendicular to the body wall. As a result, the distal end portion of the insertion section 152A is inserted into the body cavity. That is, the zigzag portion 185 including the needle 167 and the mounting surface 169 is inserted into the body cavity. The proximal end portion of the insertion section 152A is exposed to the outside of the body.

Figure 47:
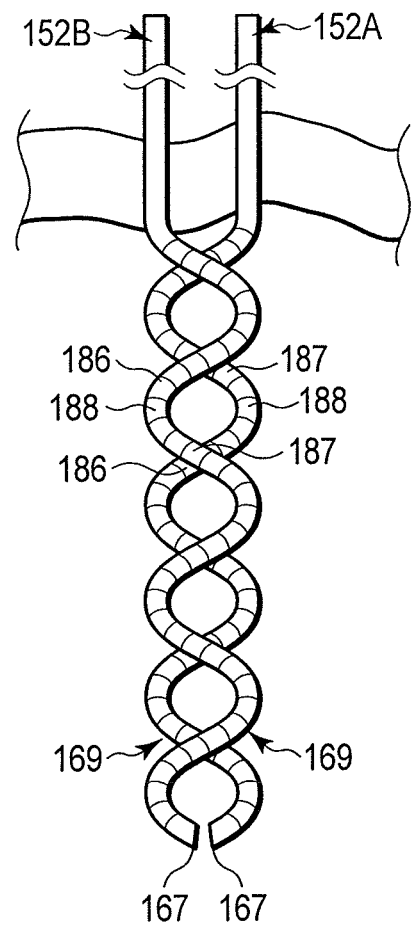
FIG. 47 is schematic view which zigzag portions of two insertion sections of the exclusion forceps according to the seventeenth embodiment are inserted into a body cavity.
Figure 50:
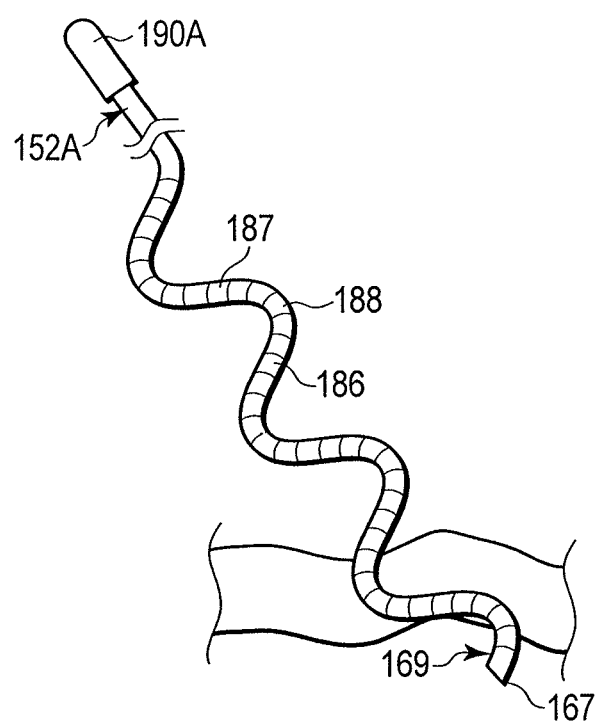
FIG. 50 is a schematic view showing a state in which a needle of one insertion section of the exclusion forceps according to the modification of the seventeenth embodiment is stuck into a body wall.
Figure 52:
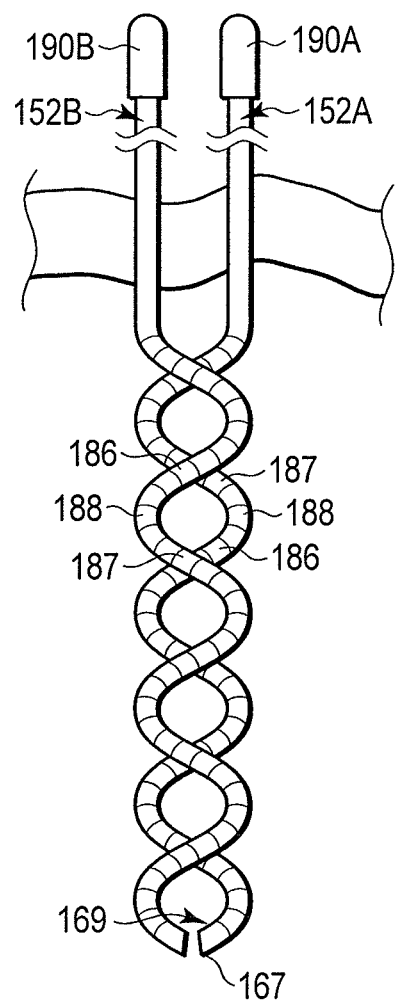
FIG. 52 is a schematic view showing a state in which zigzag portions of two insertion sections of the exclusion forceps according to the modification of the seventeenth embodiment are inserted into a body cavity.

As shown in FIG. 47, the needle 167 of an insertion section 152B different from the insertion section 152A is stuck into the body wall in the same manner as the insertion section 152A. In this case, the zigzag portion 185 is inserted into the body cavity so that the first extensions 186 and the second extensions 187 are alternately inclined relative to the body wall (laid on the body wall). When the zigzag portion 185 is inserted in the body cavity, the part to the proximal direction side of the zigzag portion 185 in the insertion section 152B is perpendicular to the body wall. In this case, the first extension 186 of the insertion section 152B intersects with the second extension 187 of the insertion section 152A, and the second extension 187 of the insertion section 152B intersects with the first extension 186 of the insertion section 152A. The proximal end portion of the insertion section 152B is exposed to the outside of the body.

The proximal end portions of the insertion sections 152A and 152B are inserted into through-bores 158 of a holder 155. As shown in FIG. 48, the insertion sections 152A and 152B are held by the holder 155 as in the first embodiment.

As described above, in the exclusion forceps 150 according to the present embodiment, the rigidity of the insertion sections 152A and 152B during exclusion is further increased by the provision of the zigzag portions 185. Thus, during exclusion, the deflecting of the insertion sections 152A and 152B can be effectively prevented, and the operability of the exclusion forceps 150 can be improved.

Modification of Seventeenth Embodiment

Although the insertion sections 152A and 152B are held by one holder 155 in the seventeenth embodiment, the present invention is not limited thereto. For example, as a modification, the insertion section 152A may be held by a holder 190A, and the insertion section 152B may be held by a holder 190B different from the holder 190A, as shown in FIG. 49 to FIG. 52. A holder (155, 190A, 190B) to which the proximal end portion of at least one of a plurality of insertion portions (152A and 152B) is removably attached has only to be provided.

Eighteenth Embodiment

Now, an eighteenth embodiment of the present invention will be described with reference to FIG. 53 to FIG. 58. In the eighteenth embodiment, the configuration according to the fifteenth embodiment is modified as follows. The same components as those in the fifteenth embodiment are provided with the same reference signs and are not described. In FIG. 53 to FIG. 58, some components are not shown for simplicity.

Figure 57:
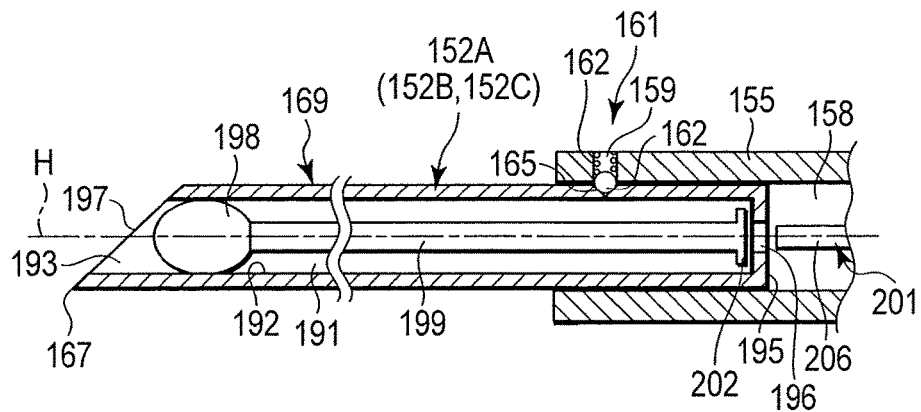
FIG. 57 is a sectional view schematically showing a state in which the insertion section of the exclusion forceps according to the eighteenth embodiment is attached to the holder and the cover member is deflated in the bore-like portion of the insertion section.
Figure 58:
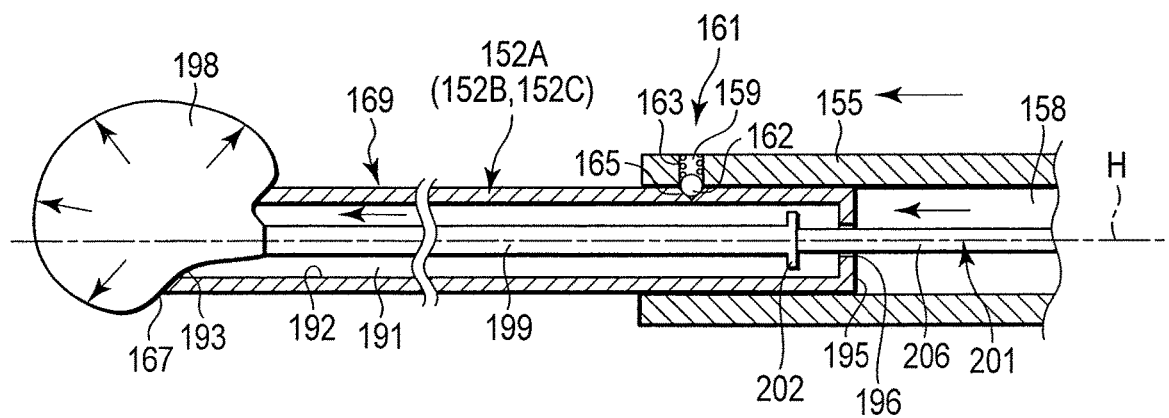
FIG. 58 is a sectional view schematically showing a state in which the insertion section of the exclusion forceps according to the eighteenth embodiment is attached to the holder and the cover member is inflated at the distal end portion of the insertion section.
Figure 59:
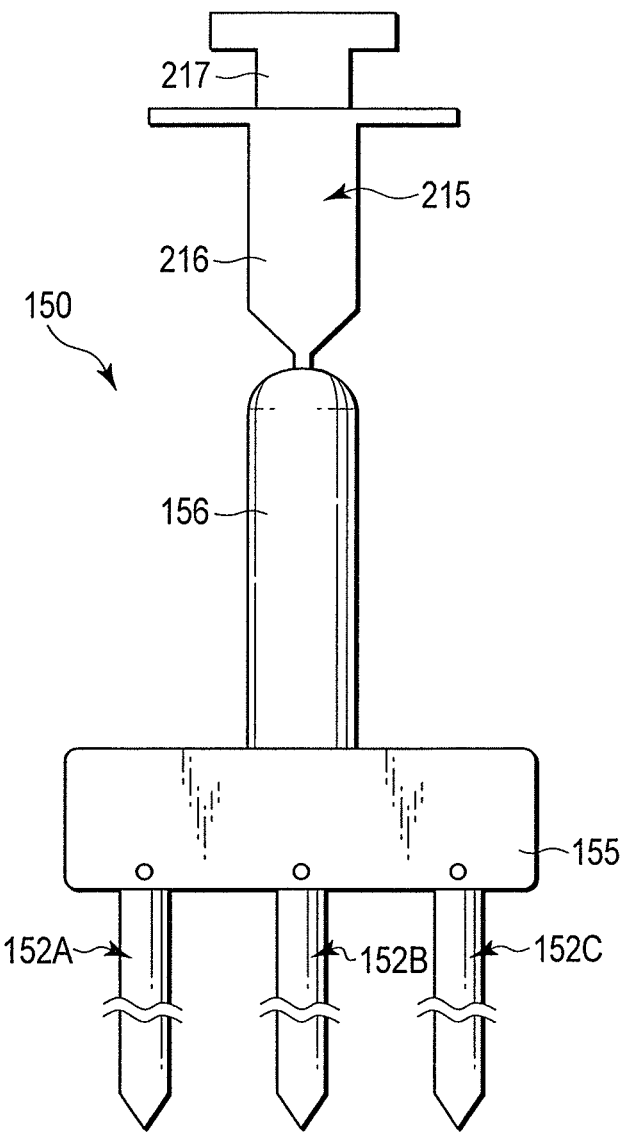
FIG. 59 is a plan view schematically showing the exclusion forceps according to a modification of the eighteenth embodiment.
Figure 60:
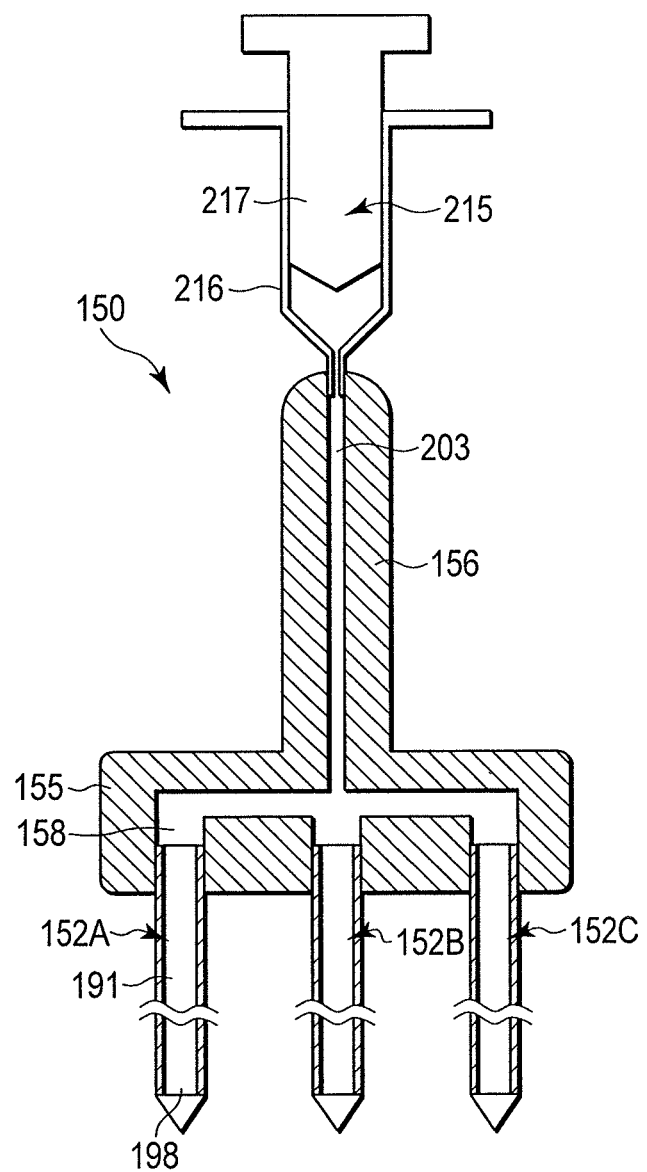
FIG. 60 is a sectional view schematically showing a state in which a cover member of an exclusion forceps according to the modification of the eighteenth embodiment is deflated in a bore-like portion of a corresponding insertion section.

FIG. 53 to FIG. 55 are diagrams showing the configuration of an exclusion forceps 150 according to the present embodiment. FIG. 56 to FIG. 58 are diagrams showing the configuration of an insertion section 152A. Although the configuration of the insertion section 152A is only described below, insertion sections 152B and 152C also have the same configuration as the insertion section 152A.

As shown in FIG. 56, the insertion section 152A includes a bore defining portion 192 which forms the insertion section 152A into a cylindrical shape and which defines a bore-like portion 191 inside of the insertion section 152A. The bore-like portion 191 extends in the longitudinal directions, and is open in an opening 193 at the distal end portion of the insertion section 152A. A wall surface 195 is provided at the proximal end portion of the insertion section 152A. An opening bore 196 which is in communication with the bore-like portion 191 is formed in the wall surface 195.

A distal surface 197 of the insertion section 152A is inclined relative to the longitudinal directions. The opening 193 is provided in the distal surface 197 of the insertion section 152A. Therefore, the opening 193 is formed to be inclined relative to the longitudinal directions. The distal face 197 positions on the proximal direction side as it goes from a first perpendicular direction (the direction of an arrow I1 in FIG. 56) to a second perpendicular direction (the direction of an arrow I2 in FIG. 56). A needle 167 is provided in a part of the outer edge of the distal surface 197 on the first perpendicular direction side. A mounting surface 169 extends from the outer edge of the distal surface 197 toward the proximal direction. The mounting surface 169 is located in a part of the outer peripheral portion of the insertion section 152A on the second perpendicular direction side.

As shown in FIG. 57 and FIG. 58, a cover member 198, configured to cover the entire distal surface 197 including the needle 167 and the opening 193, is provided at the distal end portion of the insertion section 152A. The cover member 198 covers the entire distal surface 197 so that the contact between an organ 151 and the needle 167 is prevented.

A movable member 199 is provided in the bore-like portion 191 of the insertion section 152A along an axis H of the insertion section 152A. The distal end portion of the movable member 199 is coupled to the cover member 198. A pressed portion 202 configured to be pressed by a distal end portion of a later-described press member 201 is provided at a proximal end portion of the movable member 199. The pressed portion 202 has a larger diameter than other parts of the movable member 199, and is integral with the movable member 199. The diameter of the pressed portion 202 is larger than the diameter of the opening bore 196. This prevents the movement of the movable member 199 to the proximal direction side of the opening bore 196. The movable member 199 is movable between a first movement position shown in FIG. 57 and a second movement position shown in FIG. 58 along the axis H of the insertion section 152A.

As shown in FIG. 57, when the movable member 199 is located at the first movement position, the cover member 198 is deflated to be disposed in the bore-like portion 191 of the insertion section 152A. As shown in FIG. 58, when the movable member 199 is located at the second movement position, the cover member 198 protrudes toward the distal direction from the opening 193 at the distal end of the bore-like portion 191. As a result, the cover member 198 is inflated, and covers the entire distal surface 197 including the needle 167. The contact between the organ 151 and the needle 167 is thereby effectively prevented. Here, the cover member 198 is a deflatable and inflatable elastic member such as a sponge.

As shown in FIG. 53 to FIG. 55, a holder 155 and a grip 156 are integrally formed in the present embodiment. A space 203 is provided in the holder 155 and the grip 156. The bore-like portion 191 of each of the insertion sections 152A to 152C is in communication with the space 203 via the corresponding opening bore 196.

The press member 201 is provided in the space 203. The movable member 199 is moved from the first movement position to the second movement position by the press member 201, and the cover member 198 protrudes toward the distal direction from the opening 193 of the bore-like portion 191. The press member 201 is movable in the space 203 along the longitudinal directions. The press member 201 includes a substantially T-shaped member body 205, and a plurality of protrusions 206 protruding from the member body 205 toward the distal direction. The number of the protrusions 206 provided is the same as the number of the through-bores 158, that is, the number of the insertion sections 152A to 152C. Each of the protrusions 206 is disposed in the corresponding through-bore 158.

The press member 201 moves along the longitudinal directions so that each of the protrusions 206 of the press member 201 passes through the corresponding opening bore 196 and presses the pressed portion 202 of the movable member 199 provided in the bore-like portion 191 of a corresponding one of the insertion sections 152A and 152C. In this case, the pressed portions 202 of the insertion sections 152A and 152C are simultaneously pressed. As a result, in the respective insertion sections 152A 152C, the movable members 199 move to the second movement position, and the cover members 198 simultaneously protrude toward the distal direction from the openings 193 of the bore-like portions 191. Here, each protrusion 206 of the press member 201 passes through the corresponding opening bore 196 and is formed into a proper dimension to press the pressed portion 202.

An operation section 207, which is a lever, configured to operate the press member 201 is attached to the press member 201. As shown in FIG. 53, a long bore 208 is formed in the grip 156 along the longitudinal directions. The operation section 207 extends to the outside of the grip 156 from the space 203 through the long bore 208. The long bore 208 is provided so that the operation section 207 is movable relative to the grip 156 in the longitudinal directions.

Now, the action of the exclusion forceps 150 according to the present embodiment is described. As shown in FIG. 56 and FIG. 57, the insertion sections 152A to 152C are inserted into the corresponding through-bores 158 as in the first embodiment. As in the first embodiment, a ball 162 urged by a spring member 163 is locked by a depression 165, and each of the insertion sections 152A to 152C is thereby attached to the holder 155. Thus, the insertion sections 152A and 152C are held by the holder 155 in a positioned state. In this case, each of the protrusions 206 of the press member 201 is out of contact with the corresponding movable member 199.

As shown in FIG. 54 and FIG. 55, the operation section 207 is moved along the long bore 208 in the longitudinal directions. Accordingly, the press member 201 moves in the space 203 in the longitudinal directions. As shown in FIG. 58, each of the protrusions 206 of the press member 201 passes through the corresponding opening bore 196 and presses the pressed portion 202 of the movable member 199 of the corresponding one of the insertion sections 152A and 152C. As a result, the movable member 199 moves to the second movement position from the first movement position along the axis H of the corresponding one of the insertion sections 152A and 152C. Accordingly, the cover member 198 of each of the insertion sections 152A to 152C simultaneously protrudes from the opening 193 of the corresponding bore-like portion 191. Each cover member 198 is then inflated, and covers the entire distal surface 197 including the needle 167. This prevents the contact between the organ 151 and the needle 167, and more effectively prevents damage to the organ 151.

As described above, in the exclusion forceps 150 according to the present embodiment, the movable member 199 is pressed by the press member 201, and the cover member 198 protrudes toward the distal direction from the opening 193 accordingly. As a result, the cover member 198 covering the needle 167 is inflated. This can prevent the contact between the organ 151 and the needle 167, and more effectively prevent damage to the organ 151.

In the exclusion forceps 150, the number of the protrusions 206 provided in the press member 201 is the same as the number of the insertion sections 152A to 152C. Thus, the pressed portions 202 of the movable members 199 of the respective insertion sections 152A to 152C are simultaneously pressed. Accordingly, the cover members 198 of the insertion sections 152A to 152C simultaneously protrude from the openings 193. Therefore, the needles 167 of the respective insertion sections 152A to 152C can be simultaneously covered by the corresponding cover members 198.

The cover member 198 is configured to cover the entire distal surface 197, but is not limited thereto. That is, the contact between the organ 151 and the needle 167 has only to be prevented. Therefore, the cover member 198 has only to be configured to cover at least the needle 167.

Modification of Eighteenth Embodiment

An exclusion forceps 150 shown in FIG. 59 to FIG. 64 is a modification of the eighteenth embodiment. The same components as those in the eighteenth embodiment are provided with the same reference signs and are not described.

Figure 63:
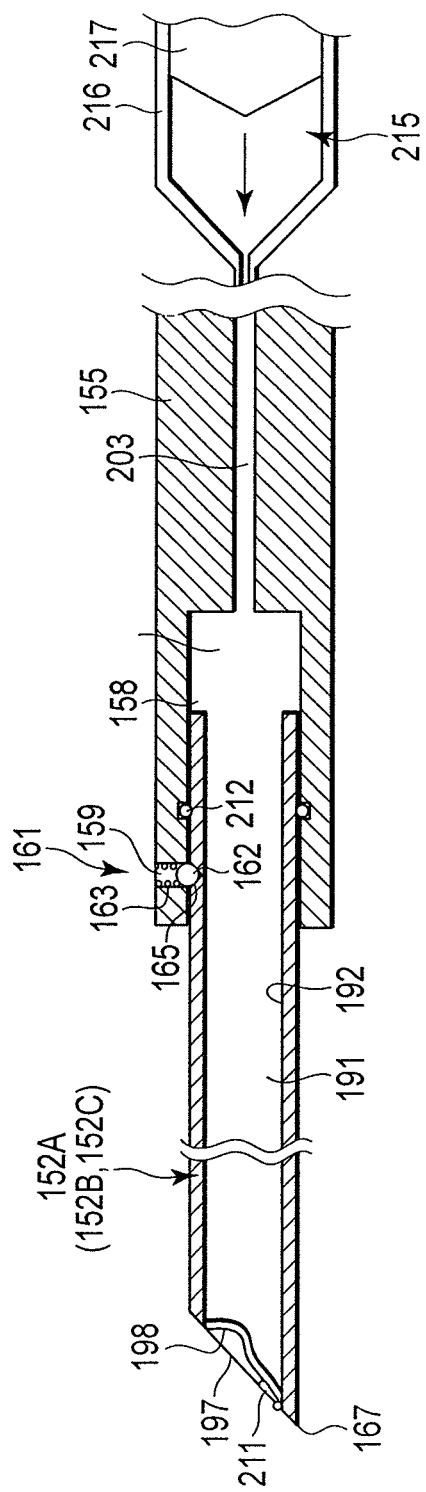
FIG. 63 is a sectional view schematically showing a state in which the insertion section of the exclusion forceps according to the modification of the eighteenth embodiment is attached to the holder and the cover member is deflated in the bore-like portion of the insertion section.
Figure 64:
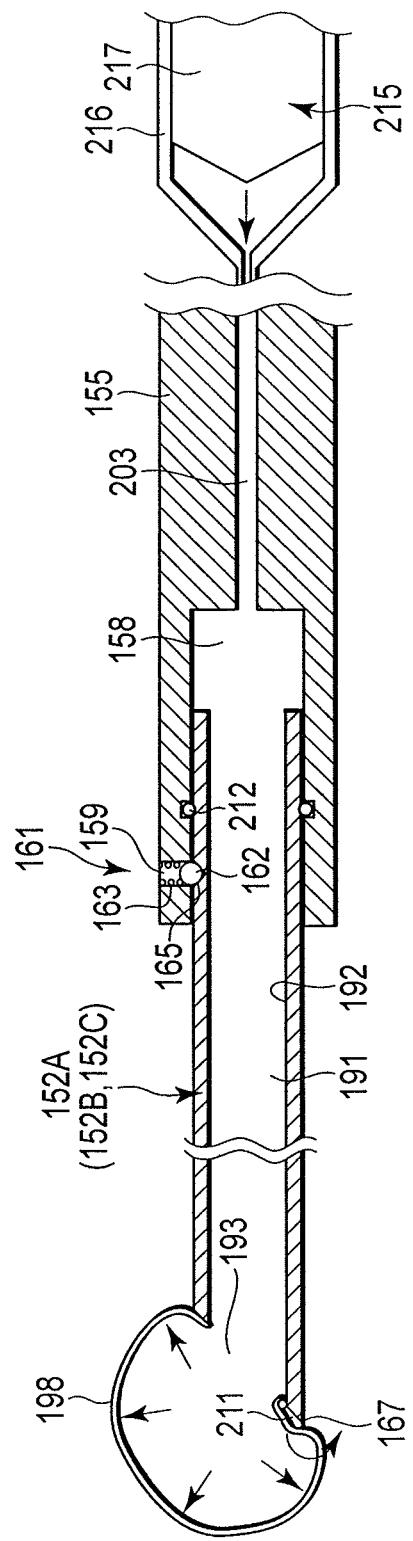
FIG. 64 is a sectional view schematically showing a state in which the insertion section of the exclusion forceps according to the modification of the eighteenth embodiment is attached to the holder and the cover member is inflated at the distal end portion of the insertion section.

As shown in FIG. 62 to FIG. 64, a cover member 198 is adhesively bonded to a distal surface 197 in the present modification. A opening 193 at the distal end of a bore-like portion 191 is closed. The cover member 198 is supplied with air via the bore-like portion 191, and is thereby inflated. As a result, the entire distal surface 197, including a needle 167 and the opening 193, is covered by the cover member 198. This prevents the contact between an organ 151 and the needle 167. Here, the cover member 198 is, for example, a balloon.

Each of the insertion sections 152A to 152C is provided with a contact prevention member 211. The contact prevention member 211 is attached to the distal surface 197 of each of the insertion sections 152A to 152C to a side where the needle 167 is located. The contact prevention member 211 is rotatable around the position where this contact prevention member 211 is attached to the distal surface 197.

As shown in FIG. 63, when the cover member 198 is deflated, the contact prevention member 211 is located in the opening 193. In this case, the contact prevention member 211 is located to the distal direction side of the cover member 198. As shown in FIG. 64, in response to the inflation of the cover member 198, the contact prevention member 211 rotates around the position where this contact prevention member 211 is attached to the distal surface 197. As a result, the contact prevention member 211 is disposed between the needle 167 and the cover member 198. Thus, the contact between the cover member 198 and the needle 167 is prevented by the contact prevention member 211, and the bursting of the cover member 198 caused by the needle 167 is prevented.

In a through-bore 158, an elastic member 212 such as an O-ring is provided between each of the insertion sections 152A to 152C and a holder 155. This keeps the space between the holder 155 and each of the insertion sections 152A to 152C airtight. In the present modification, no wall surface 195 is provided at the proximal end of each of the insertion sections 152A to 152C.

Air is supplied to each through-bore 158 via a space 203 in the holder 155 and a grip 156. That is, the space 203, the through-bore 158, and the bore-like portion 191 serve as an air supply passage configured to supply a gas to inflate the cover member 198.

An air supply unit 215 is attached to the grip 156. The air supply unit 215 includes a syringe 216 filled with an amount of a gas to inflate the cover member 198. An inside of the syringe 216 is in communication with the space 203. The air supply unit 215 includes a piston 217 configured to supply the gas filling the syringe 216 to the space 203. An amount of the gas to inflate the cover member 198 is supplied to the cover member 198 by the syringe 216 and the piston 217. Here, the piston 217 moves toward the distal direction relative to the syringe 216, and the gas is thereby supplied to the space 203 from the syringe 216.

As described above, the present modification can provide the advantageous effects similar to those according to the eighteenth embodiment. The contact prevention member 211 can prevent the cover member 198 from being burst by the needle 167. Moreover, for example, the movable member 199 according to the eighteenth embodiment is not provided, so that the configuration of each of the insertion sections 152A to 152C is simpler. Thus, the manufacturing costs of the exclusion forceps 150 can be lower.

Other characteristic technical matters according to the present invention are additionally set forth below.

Notes (Additional Note 1)

A sticking assist instrument used to insert a plurality of insertion sections into a body cavity through a body wall during an use of a rigid endoscope, the rigid endoscope including a body, and the insertion sections which are arranged apart from one another in directions perpendicular to longitudinal directions and which extend from the body toward a distal direction, the sticking assist instrument comprising:

an instrument body; and a plurality of inner peripheral surfaces which is provided in the instrument body so that axes thereof are parallel to one another along insertion/removal directions of the insertion sections, the inner peripheral surfaces each defining a space through which a corresponding one of the insertion sections passes during an insertion of the insertion sections into the body cavity, wherein each of the inner peripheral surfaces includes a first diametrical dimension portion provided in a part on an insertion direction side, a second diametrical dimension portion which is provided in a part on a removal direction side and which is larger in diametrical dimension than the first diametrical dimension portion, and a diametrical dimension changeable portion which is provided between the first diametrical dimension portion and the second diametrical dimension portion and in which diameter is decreases as it goes from the second diametrical dimension portion toward the first diametrical dimension portion.

(Additional note 2)

The sticking assist instrument according to Additional note 1, wherein the inner peripheral surfaces include a first inner peripheral surface and a second inner peripheral surface, and a distance between an axis of the first inner peripheral surface and an axis of the second inner peripheral surface is the same as a distance between an axis of a first insertion section which is the insertion section corresponding to the first inner peripheral surface and an axis of a second insertion section which is the insertion section corresponding to the second inner peripheral surface at a proximal ends of the insertion sections.

(Additional Note 3)

The sticking assist instrument according to Additional note 1, wherein the inner peripheral surfaces includes a first inner peripheral surface and a second inner peripheral surface, the first inner peripheral surface defining a space through which an observation insertion sections including an observation section configured to observe a subject among the insertion sections is passed, and the second inner peripheral surface defining a space through which an irradiation insertion section including an illumination section configured to apply light to the subject among the insertion sections is passed.

(Additional Note 4)

The sticking assist instrument according to Additional note 1, further comprising: a cylindrical instrument needle which protrudes from the instrument body toward the insertion direction, and which is configured to stick into the body wall during the insertion of the insertion sections into the body cavity, wherein the inner peripheral surfaces include a coaxial inner peripheral surface which is formed coaxially with the instrument needle, and which is formed so that the diametrical dimension of the first diametrical dimension portion is the same as an inside diameter of the instrument needle, the defined space being in communication with an inside of the instrument needle in the coaxial inner peripheral surface.

(Additional Note 5)

The sticking assist instrument according to Additional note 4, wherein the instrument needle includes a first instrument needle, and a second instrument needle different from the first instrument needle in a protruding length from the instrument body.

(Additional Note 6)

The sticking assist instrument according to Additional note 4, further comprising: a first outflow prevention portion which is provided to the coaxial inner peripheral surface or inside of the instrument needle, and which is configured to prevent the outflow of air from the space defined by the coaxial inner peripheral surface to an outside when the insertion sections are not inserted in the body cavity, a second outflow prevention portion which is provided to the coaxial inner peripheral surface or inside of the instrument needle, and which is configured to prevent the outflow of air from the space defined by the coaxial inner peripheral surface to the outside when the insertion sections are inserted in the body cavity.

(Additional Note 7)

The sticking assist instrument according to Additional note 4, wherein the instrument body includes a fixing portion configured to be fixed to a body surface during use, and a movable portion in which the instrument needle extends toward the insertion direction from an end on the insertion direction side thereof, and which is movable integrally with the instrument needle relative to the fixing portion in the insertion/removal directions of the insertion sections, the coaxial inner peripheral surface being provided along the insertion/removal directions of the insertion sections in the movable portion.

(Additional Note 8)

The sticking assist instrument according to Additional note 7, further comprising: a rotary unit which is configured to move the movable portion in the insertion/removal directions of the insertion sections so that the movable portion rotates around the axis of the coaxial inner peripheral surface.

(Additional Note 9)

An exclusion forceps comprising:

a plurality of insertion sections each of which includes an exclusion section provided at a distal end portion of the insertion section and configured to exclude a living tissue, and each of which extends in longitudinal directions, the insertion sections being configured to increase rigidity during the exclusion of the living tissue as compared with a single insertion section, wherein each of the insertion sections includes a needle which is provided at the distal end portion of the insertion section, and which is configured to be stuck into a body wall during an insertion of the insertion sections into a body cavity.

(Additional Note 10)

The exclusion forceps according to Additional note 9, further comprising:

a holder to which a proximal end portion of at least one of the insertion sections is removably attached, and which is configured to hold the insertion portions.

(Additional Note 11)

The exclusion forceps according to Additional note 10, wherein each of the exclusion sections includes a mounting surface which extends from the distal end portion of the corresponding insertion section toward the proximal direction, and which is located on an opposite side of the needle across the axis of the corresponding insertion section, the living tissue to be excluded being configured to be mounted on the mounting surface.

(Additional Note 12)

The exclusion forceps according to Additional note 11, wherein the mounting surface includes an uneven portion which has an uneven surface, and which is configured to prevent the living tissue mounted on the mounting surface from sliding over the mounting surface.

(Additional Note 13)

The exclusion forceps according to Additional note 11, wherein each of the insertion sections includes a curved portion which is provided at the distal end portion of the insertion section, and which is curved from a first perpendicular direction where the needle is located to a second perpendicular direction where the mounting surface is located.

(Additional Note 14)

The exclusion forceps according to Additional note 10, further comprising: a parallel link unit which rotatably attaches the insertion sections to the holder, wherein the parallel link unit includes:

a plurality of rotary members, the number of the rotary members provided being the same as the insertion sections, the corresponding one of the insertion sections being attached to each of the rotary members, and each of the rotary members being configured to rotate relative to the holder around a rotation axis integrally with the corresponding insertion portion; and a link member which links the rotary members so that the rotary members rotate in the same direction.

(Additional Note 15)

The exclusion forceps according to Additional note 10, wherein each of the insertion sections includes a zigzag portion provided zigzag at the distal end portion including the needle, and the zigzag portion includes a plurality of first extensions extending in such a manner as to be inclined relative to the longitudinal directions, a plurality of second extensions extending in such a manner as to be inclined relative to the longitudinal directions toward a direction opposite to the first extensions, and a top provided between the first extension and the second extension.

(Additional Note 16)

The exclusion forceps according to Additional note 10, wherein each of the insertion sections includes:

a bore defining portion which forms the insertion section into a cylindrical shape, and which defines, inside of the insertion section, a bore-like portion that is open in an opening at the distal end portion of the insertion section, and a cover member which is provided at the distal end portion of the insertion section in a state that the cover is able to cover the needle, and which is configured to prevent the contact between the living tissue and the needle when covering the needle.

(Additional Note 17)

The exclusion forceps according to Additional note 16, wherein each of the insertion sections includes a movable member which is movable in the bore-like portion between a first movement position and a second movement position along the axis of the insertion section, and the cover member is configured to be deflated in a state that the cover is disposed in the bore-like portion of the insertion section when the movable member is located at the first movement position, and configured to protrude toward the distal direction from the opening and be inflated in a state that the cover covers the needle when the movable member is located at the second movement position.

(Additional Note 18)

The exclusion forceps according to Additional note 16, further comprising: an air supply unit which is configured to supply air via the bore-like portion, the cover member is inflated in a state that the cover covers the needle when air is supplied thereto from the air supply unit.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A rigid endoscope having a plurality of functions, the rigid endoscope comprising:

a first insertion section extending along longitudinal directions;

a first lumen defining portion which is formed in the first insertion section along the longitudinal directions, and which defines a first lumen that is open in a first opening at a distal end portion of the first insertion section;

a first needle which defines an outer edge of the first opening, and which is sharpened from a proximal direction toward a distal direction;

a first functional section which is provided in a vicinity of the first opening of the first lumen, and which is configured to perform some part of the functions;

a second insertion section which extends along the longitudinal directions, and which is spaced apart from the first insertion section in directions perpendicular to the longitudinal directions;

a second lumen defining portion which is formed in the second insertion section along the longitudinal directions, and which defines a second lumen that is open in a second opening at a distal end portion of the second insertion section;

a second needle which defines an outer edge of the second opening, and which is sharpened from the proximal direction toward the distal direction;

a second functional section which is provided in a vicinity of the second opening of the second lumen, and which is configured to perform some part of the functions different from the functions performed by the first functional section; and a gripped body from which the first insertion section and the second insertion section extend toward the distal direction, and which integrally supports a proximal end portion of the first insertion section and a proximal end portion of the second insertion section in a state that the first insertion section and the second insertion section are apart from each other in directions perpendicular to the longitudinal directions, wherein the first insertion section and the second insertion section are configured to move integrally with the gripped body by moving of the gripped body while a distance between the first insertion section and the second insertion section in the directions perpendicular to the longitudinal directions is maintained, the first insertion section includes an observation insertion section which includes, as the first functional section, an observation section configured to observe a subject, the first needle and the second needle are configured to be stuck into a body wall during using so that the first insertion section and the second insertion section are inserted into a body cavity which exists inside the body wall, the gripped body is configured to be gripped outside the body during using when the first insertion section and the second insertion section are inserted simultaneously into the body cavity, and the first insertion section and the second insertion section are configured to simultaneously enter the body cavity and to move integrally with the gripped body by moving the gripped body outside the body wall during using.

2. The rigid endoscope according to claim 1, further comprising:

a link unit which removably links at least one of the first insertion section and the second insertion section to the body.

3. The rigid endoscope according to claim 1, wherein the observation section includes an objective lens configured to form a subject image, and an image pickup unit which is provided to the proximal direction side of the objective lens, and which is configured to pick up the subject image formed by the objective lens.

4. The rigid endoscope according to claim 1, further comprising a body provided to the proximal direction side of the first insertion section and the second insertion section, wherein the body includes an image pickup unit configured to pick up a subject image, and the observation section includes an objective lens configured to form the subject image picked up by the image pickup unit, and a relay lens unit configured to guide the subject image formed by the objective lens to the image pickup unit.

5. The rigid endoscope according to claim 1, further comprising a body provided to the proximal direction side of the first insertion section and the second insertion section, wherein at least one of the first insertion section and the second insertion section includes a rotary insertion section rotatable in directions around an axis relative to the body.

6. The rigid endoscope according to claim 5, wherein the rotary insertion section includes the observation insertion section, and an irradiation insertion section which is the second insertion section including, as the second functional section, an illumination section configured to apply light to the subject.

7. The rigid endoscope according to claim 6, further comprising a direction adjustment portion which is configured to rotate the irradiation insertion section in the directions around the axis in the same direction and in the same amount as the observation insertion section in response to the rotation of the observation insertion section in the directions around the axis, and which is configured to make an adjustment so that an observation direction of the observation section corresponds to an illumination direction of the illumination section.

8. The rigid endoscope according to claim 1, further comprising a body which includes a first formation, and a second formation removably attached to the first formation, and which is provided to the proximal direction side of the first insertion section and the second insertion section, wherein the first insertion section includes a reuse insertion section which extends from the first formation toward the distal direction, and which is configured to be reused by cleaning and sterilization after use, and the second insertion section includes a disposable insertion section which extends from the second formation toward the distal direction, and which is configured to be disposed of after use.

9. The rigid endoscope according to claim 8, wherein the reuse insertion section includes the observation insertion section, and an irradiation insertion section which is located apart from the observation insertion section in the directions perpendicular to the longitudinal directions, and which includes, as the first functional section, an illumination section configured to apply light to the subject, and the disposable insertion section includes an air/water supply insertion section which includes, as the second functional section, an air/water supply section configured to supply air/water.

10. The rigid endoscope according to claim 1, wherein at least one of the first insertion section and the second insertion section includes a shape changeable insertion section which is configured to change a shape of its distal end when force is applied thereto from the distal direction, and the shape changeable insertion section includes: a movable member which stores the first functional section or the second functional section, and which is movable in the longitudinal directions integrally with the first functional section or the second functional section, the movable member being configured to move between a first position where a distal end of the movable member is located to the distal direction side of a distal end of the first needle or the second needle and a second position where the distal end of the movable member is located to the proximal direction side of the distal end of the first needle or the second needle;

and an urging member which is configured to urge the movable member toward the distal direction to be located at the first position when no force is applied from the distal direction.

11. The rigid endoscope according to claim 10, wherein the shape changeable insertion section includes a plurality of array insertion sections which are the second insertion sections, the array insertion sections being arranged apart from one another in the directions perpendicular to the longitudinal directions, the array insertion sections being arrayed around the observation insertion section in directions around an axis of the observation insertion section, and a distal end of the movable member of each of the array insertion sections being located to the distal direction side of the distal end of the first needle of the observation insertion section when no force is applied from the distal direction.

12. The rigid endoscope according to claim 1, further comprising a plurality of insertion sections which only consist of the single first insertion section, and the at least one second insertion section, wherein in the second insertion section, a distal end of each of the second needles is located a dimension of 2 mm or more and 10 mm or less apart from a distal end of the first needle of the first insertion section in the directions perpendicular to the longitudinal directions.

13. The rigid endoscope according to claim 1, further comprising a plurality of insertion sections which only consists of the single first insertion section, and the second insertion sections, wherein the second insertion sections only consists of at least one near position insertion section in which a distal end of each of the second needles is located a dimension of 2 mm or more and 10 mm or less apart from a distal end of the first needle of the first insertion section in the directions perpendicular to the longitudinal directions, and at least one far position insertion section in which the distal end of each of the second needles is located a dimension of more than 10 mm apart from the distal end of the first needle of the first insertion section in the directions perpendicular to the longitudinal directions, and in the far position insertion section, the distal end of each of the second needles is located a dimension of 2 mm or more and 10 mm or less apart from the distal end of the at least one second needle of the other second insertion sections in the directions perpendicular to the longitudinal directions.

14. The rigid endoscope according to claim 13, further comprising a body provided to the proximal direction side of the insertion sections, wherein the insertion sections are arrayed in circumferential directions of the body, and the near position insertion section includes an adjacent insertion section adjacent to the first insertion section in the circumferential directions of the body.

15. The rigid endoscope according to claim 13, wherein the insertion sections are arrayed in array directions which are specified directions perpendicular to the longitudinal directions, and the near position insertion section includes an adjacent insertion section adjacent to the first insertion section in the array directions.

* * * * *